（12） United States Patent
Lau et al.

(10) Patent No.: US 8,148,413 B2
(45) Date of Patent: Apr. 3, 2012

(54) N-HETEROARYL INDOLE CARBOXAMIDES AND ANALOGUES THEREOF, FOR USE AS GLUCOKINASE ACTIVATORS IN THE TREATMENT OF DIABETES

(75) Inventors: Jesper Lau, Farum (DK); Per Vedsø, Vaerløse (DK); János Tibor Kodra, Copenhagen (DK); Anthony Murray, Hellerup (DK); Lone Jeppesen, Virum (DK); Michael Ankersen, Stenløse (DK); Govindan Subramanian, High Point, NC (US); Adnan M. M. Mjalli, Jamestown, NC (US); Robert Carl Andrews, Jamestown, NC (US); Dharma Rao Polisetti, High Point, NC (US); Daniel Peter Christen, High Point, NC (US)

(73) Assignee: TransTech Pharma, Inc., High Point, NC (US)

( * ) Notice: Subject to any disclaimer, the term of this patent is extended or adjusted under 35 U.S.C. 154(b) by 0 days.

(21) Appl. No.: 12/895,761

(22) Filed: Sep. 30, 2010

(65) Prior Publication Data

US 2011/0082144 A1 Apr. 7, 2011

Related U.S. Application Data

(60) Division of application No. 11/439,820, filed on May 24, 2006, now Pat. No. 7,812,043, which is a continuation of application No. PCT/DK2004/000814, filed on Nov. 24, 2004.

(60) Provisional application No. 60/525,101, filed on Nov. 25, 2003.

(30) Foreign Application Priority Data

Nov. 24, 2003 (EP) .................................... 03388079

(51) Int. Cl.
*A61K 31/427* (2006.01)
*C07D 417/12* (2006.01)
(52) U.S. Cl. ........................................ 514/371; 548/181
(58) Field of Classification Search .................. 514/371; 548/181
See application file for complete search history.

(56) References Cited

U.S. PATENT DOCUMENTS 6,365,748 B1 4/2002 Radisson
6,881,844 B2 4/2005 Corbett

FOREIGN PATENT DOCUMENTS

| WO | WO 98/51686 A1 | 11/1998 |
| WO | WO 01/64639 A2 | 9/2001 |
| WO | WO 03/035621 A1 | 5/2003 |
| WO | WO 03/091213 A1 | 6/2003 |

OTHER PUBLICATIONS

"Health Implications of Obesity" NIH, Ann Intern Med., 1985, vol. 103, pp. 147-151.
Boger et al. "Total Synthesis of Distamycin A and 2640 Analogues: A solution-Phase Combinatorial Approach to the Discovery of New, Bioactive DNA Binding Agents and Development of a Rapid, High-Throughput Screen for Determining Relative DNA Binding Affinity or DNA Binding Sequence Selectivity," J. Am. Chem. Soc., 2000, vol. 122, pp. 6382-6394.
Duflos et al. "N-Pyridinyl-indole-3-(alkyl)carboxamides and derivatives as potential systemic and topical inflammation inhibitors," Eur. J. Med. Chem., 2001, vol. 36, pp. 545-553.
International Search Report mailed on Jan. 26, 2005 for PCT Application No. PCT/DK2004/000814.
Mann, "The Influence of Obesity on Health (Second of Two Parts)," The New England Journal of Medicine, 1974, pp. 226-232.
Ölgen et al. "Syntheses and biological evaluation of indole-2 and 3-carboxamides: new selective cyclooxygenase-2 inhibitors," Pharmazie, 2002, vol. 57, pp. 238-242.
Ölgen et al. "Synthesis and Antioxidant Properties of Novel N-Substituted Indole-2-carboxamide and Indole-3-acetamide Derivatives," Arch. Pharm. Med. Chem., 2002, vol. 7, pp. 331-338.
Palmer et al. "Tyrosine Kinase Inhibitors. 4. Structure-Activity Relationships among N- and 3-Substituted 2,2-Dithiobis (1H-indoles) for in vitro Inhibition of Receptor and Nonreceptor Protein Tyrosine Kinases," J. Med. Chem., 1995, vol. 38, pp. 58-67.
Robert et al. "Non-carboxylic antiinflammatory compounds. III. N-(4,6-Dimethylpyridin-2-yl)arylcarboxamides and arylthiocarboxamides acting as brain edema inhibitors," Eur J Med Chem, 1995, vol. 30, pp. 915-924.
Unangst et al. "Novel Indolecarboxamidotetrazoles as Potential Antiallergy Agents," J. Med. Chem., 1989, vol. 32, pp. 1360-1366.

*Primary Examiner* — Charanjit Aulakh
(74) *Attorney, Agent, or Firm* — Kilpatrick Townsend & Stockton LLP

(57) ABSTRACT

This invention relates to compounds that are activators of glucokinase and thus may be useful for the management, treatment, control, or adjunct treatment of diseases, where increasing glucokinase activity is beneficial. The compounds are of the general formula (I)

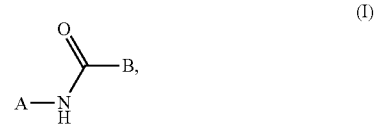

wherein A and B are further defined in the application.

8 Claims, No Drawings

N-HETEROARYL INDOLE CARBOXAMIDES AND ANALOGUES THEREOF, FOR USE AS GLUCOKINASE ACTIVATORS IN THE TREATMENT OF DIABETES

CROSS-REFERENCE TO RELATED APPLICATIONS

This application is a continuation of International Application Number: PCT/DK2004/000814, filed Nov. 24, 2004, which claims priority to European Patent Application Number EP 03388079.0, filed Nov. 24, 2003, and U.S. Provisional Application No. 60/525,101, filed Nov. 25, 2003, the contents of each of which is incorporated herein in its entirety.

FIELD OF THE INVENTION

This invention relates to compounds that are activators of glucokinase and thus may be useful for the management, treatment, control, or adjunct treatment of diseases, where increasing glucokinase activity is beneficial.

BACKGROUND OF THE INVENTION

Diabetes is characterised by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulphonylureas that stimulate β-cell function or with agents that enhance the tissue sensitivity of the patients towards insulin or with insulin. Among the agents applied to enhance tissue sensitivity towards insulin metformin is a representative example.

Even though sulphonylureas are widely used in the treatment of NIDDM this therapy is, in most instances, not satisfactory: In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

In normal subjects as well as in diabetic subjects, the liver produces glucose in order to avoid hypoglycaemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production. Similarly, hepatic glucose production will be increased in type 1 diabetes, if the disease is not properly controlled by insulin treatment.

Since existing forms of therapy of diabetes does not lead to sufficient glycaemic control and therefore are unsatisfactory, there is a great demand for novel therapeutic approaches.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which occurs in the human population as a secondary symptom to various other disorders such as renal artery stenosis, pheochromocytoma, or endocrine disorders. However, hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain haemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain haemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension.

Cardiac hypertrophy is a significant risk factor in the development of sudden death, myocardial infarction, and congestive heart failure. Theses cardiac events are due, at least in part, to increased susceptibility to myocardial injury after ischemia and reperfusion, which can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20-25% in some series. In addition, of the 400,000 patients undergoing coronary bypass surgery annually, perioperative myocardial infarction is estimated to occur in 5% and death in 1-2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exists. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann G V N. Engl. J. Med 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity.

The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal-induced gastric distension is another possible inhibitory factor. Additionally the hypothalamic centres are sensitive to catecholamines, and beta-adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

SUMMARY OF THE INVENTION

One aspect of the present invention is to provide compounds that are activators of glucokinase and thus may be useful for the management, treatment, control, or adjunct treatment of diseases where increasing glucokinase activity is beneficial.

It is another aspect of the present invention to provide a pharmaceutical composition comprising, as an active ingredient, at least one compound according to the present invention together with one or more pharmaceutically acceptable carriers or excipients.

It is another aspect of the present invention to provide use of a compound represented by the general formula (II)

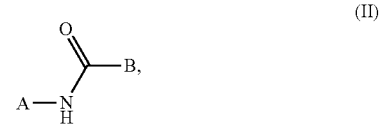

wherein A and B are defined below,
as well as any salt hereof with a pharmaceutically acceptable acid or base, or any optical isomer or mixture of optical isomers, including a racemic mixture, or any tautomeric forms, for the preparation of a medicament for increasing the activity of glucokinase.

Furthermore it is an aspect of the invention to provide the use of a compound of the invention for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins.

These and further aspects of the invention will become apparent during the following detailed description.

DEFINITIONS

In the structural formulas given herein and throughout the present specification, the following terms have the indicated meaning:

The term "optionally substituted" as used herein means that the moiety which is optionally substituted is either unsubstituted or substituted with one or more of the substituents specified. When the moiety in question is substituted with more than one substituent, the substituent may be the same or different.

The term "adjacent" as used herein regards the relative positions of two atoms or variables, these two atoms or variables sharing a bond or one variable preceding or succeeding the other in a variable specification. By way of example, "atom A adjacent to atom B" means that the two atoms A and B share a bond.

The term "halogen" or "halo" means fluorine, chlorine, bromine or iodine.

The term "perhalomethyl" means trifluoromethyl, trichloromethyl, tribromomethyl, or triiodomethyl.

The use of prefixes of this structure: $C_{x-y}$-alkyl, $C_{x-y}$-alkenyl, $C_{x-y}$-alkynyl, $C_{x-y}$-cycloalyl or $C_{x-y}$-cycloalkyl-$C_{x-y}$-alkenyl-designates radical of the designated type having from x to y carbon atoms.

The term "alkyl" as used herein, alone or in combination, refers to a straight or branched chain saturated monovalent hydrocarbon radical having from one to ten carbon atoms, for example $C_{1-8}$-alkyl or $C_{1-6}$-alkyl. Typical $C_{1-8}$-alkyl groups and $C_{1-6}$-alkyl groups include, but are not limited to e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl. The term "$C_{1-6}$-alkyl" as used herein also includes secondary $C_{3-6}$-alkyl and tertiary $C_{4-6}$-alkyl.

The term "alkylene" as used herein, alone or in combination, refers to a straight or branched chain saturated divalent hydrocarbon radical having from one to ten carbon atoms, for example $C_{1-8}$-alkylene or $C_{1-6}$-alkylene. Examples of "alkylene" as used herein include, but are not limited to, methylene, ethylene, and the like.

The term "alkenyl" as used herein, alone or in combination, refers to a straight or branched chain monovalent hydrocarbon radical containing from two to ten carbon atoms and at least one carbon-carbon double bond, for example $C_{2-8}$-alkenyl or $C_{2-6}$-alkenyl. Typical $C_{2-8}$-alkenyl groups and $C_{2-6}$-alkenyl groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "alkenylene" as used herein, alone or in combination, refers to a straight or branched chain divalent hydrocarbon radical having from two to ten carbon atoms and at least one carbon-carbon double bond, for example $C_{2-8}$-alkenylene or $C_{2-6}$-alkenylene. Typical $C_{2-8}$-alkenylene groups and $C_{2-6}$-alkenylene groups include, but are not limited to, ethene-1,2-diyl, propene-1,3-diyl, methylene-1,1-diyl, and the like.

The term "alkynyl" as used herein alone or in combination, refers to a straight or branched monovalent hydrocarbon radical containing from two to ten carbon atoms and at least one triple carbon-carbon bond, for example $C_{2-8}$-alkynyl or $C_{2-6}$-alkynyl. Typical $C_{2-8}$-alkynyl groups and $C_{2-6}$-alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "alkynylene" as used herein alone or in combination, refers to a straight or branched chain divalent hydrocarbon radical having from two to ten carbon atoms and at least one carbon-carbon triple bond, for example $C_{2-8}$-alkynylene or $C_{2-6}$-alkynylene. Typical $C_{2-8}$-alkynylene groups and $C_{2-6}$-alkynylene groups include, but are not limited to, ethyne-1,2-diyl, propyne-1,3-diyl, and the like.

The term "cycloalkyl" as used herein, alone or in combination, refers to a non-aromatic monovalent hydrocarbon radical having from three to twelve carbon atoms, and optionally with one or more degrees of unsaturation, for example $C_{3-8}$-cycloalkyl. Such a ring may be optionally fused to one or more benzene rings or to one or more of other cycloalkyl ring(s). Typical $C_{3-8}$-cycloalkyl groups include, but are not limited to, cyclopropyl, cyclobutyl, cyclopentyl, cyclohexyl, cyclohexenyl, cycloheptyl, cycloheptenyl, cyclooctyl and the like.

The term "cycloalkylene" as used herein, alone or in combination, refers to a non-aromatic carbocyclic divalent hydrocarbon radical having from three to twelve carbon atoms and optionally possessing one or more degrees of unsaturation, for example $C_{3-8}$-cycloalkylene. Such a ring may be optionally fused to one or more benzene rings or to one or more of other cycloalkyl ring(s). Typical $C_{3-8}$-cycloalkylene groups include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

The term "heterocyclic" or the term "heterocyclyl" as used herein, alone or in combination, refers to a three to twelve membered heterocyclic ring having one or more degrees of unsaturation containing one or more heteroatomic substitutions selected from S, SO, $SO_2$, O, or N, for example $C_{3-8}$-heterocyclyl. Such a ring may be optionally fused to one or more of another "heterocyclic" ring(s) or cycloalkyl ring(s). Typical $C_{3-8}$-heterocyclyl groups include, but are not limited to, tetrahydrofuran, 1,4-dioxane, 1,3-dioxane, piperidine, pyrrolidine, morpholine, piperazine, and the like.

The term "heterocyclylene" as used herein, alone or in combination, refers to a three to twelve-membered heterocyclic ring diradical optionally having one or more degrees of unsaturation containing one or more heteroatoms selected from S, SO, SO₂, O, or N. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

The term "alkoxy" as used herein, alone or in combination, refers to the monovalent radical $R^aO$—, where $R^a$ is alkyl as defined above, for example $C_{1-8}$-alkyl giving $C_{1-8}$-alkoxy. Typical $C_{1-8}$-alkoxy groups include, but are not limited to, methoxy, ethoxy, n-propoxy, isopropoxy, butoxy, sec-butoxy, tert-butoxy, pentoxy, isopentoxy, hexoxy, isohexoxy and the like.

The term "alkylthio" as used herein, alone or in combination, refers to a straight or branched monovalent radical comprising an alkyl group as described above linked through a divalent sulphur atom having its free valence bond from the sulphur atom, for example $C_{1-8}$-alkylthio. Typical $C_{1-8}$-alkylthio groups include, but are not limited to, methylthio, ethylthio, propylthio, butylthio, pentylthio, hexylthio and the like.

The term "alkoxycarbonyl" as used herein refers to the monovalent radical $R^aOC(O)$—, where $R^a$ is alkyl as described above, for example $C_{1-8}$-alkoxycarbonyl. Typical $C_{1-8}$-alkoxycarbonyl groups include, but are not limited to, methoxycarbonyl, ethoxycarbonyl, propoxycarbonyl, isopropoxycarbonyl, n-butoxycarbonyl, sec-butoxycarbonyl, tertbutoxycarbonyl, 3-methylbutoxycarbonyl, n-hexoxycarbonyl and the like.

The term "carbamoyl" as used herein refers to $NH_2C(O)$—.

The term "aryl" as used herein refers to a carbocyclic aromatic ring radical or to a aromatic ring system radical. Aryl is also intended to include the partially hydrogenated derivatives of the carbocyclic systems.

The term "heteroaryl", as used herein, alone or in combination, refers to an aromatic ring radical with for instance 5 to 7 member atoms, or to a aromatic ring system radical with for instance from 7 to 18 member atoms, containing one or more heteroatoms selected from nitrogen, oxygen, or sulfur heteroatoms, wherein N-oxides and sulfur monoxides and sulfur dioxides are permissible heteroaromatic substitutions; such as e.g. furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like. Heteroaryl is also intended to include the partially hydrogenated derivatives of the heterocyclic systems enumerated below.

Examples of "aryl" and "heteroaryl" includes, but are not limited to phenyl, biphenyl, indene, fluorene, naphthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl-1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxazo-5-yl), isothiazolyl (isothiazo-3-yl, isothiazo-4-yl, isothiaz-5-yl) thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydro-benzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl(2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), purinyl, and tetrazolyl (5-tetrazolyl, N-tetrazolyl).

The present invention also relates to partly or fully saturated analogues of the ring systems mentioned above.

When two such terms are used in combination, such as in aryl-alkyl, heteroaryl-alkyl, cycloalkyl-$C_{1-6}$-alkyl and the like, it is to be understood that the first mentioned radical is a substituent on the latter mentioned radical, where the point of substitution, i.e. the point of attachment to another part of the molecule, is on the latter of the radicals, for example aryl-alkyl-:

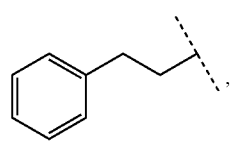

, cycloalkyl-alkyl-:

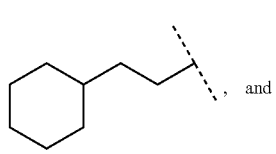

, and aryl-alkoxy-:

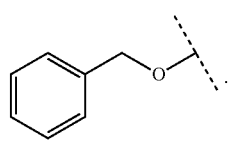

The term "arylene", as used herein, alone or in combination, refers to carbocyclic aromatic ring diradical or to a aromatic ring system diradical. Examples of "arylene" include, but are not limited to, benzene-1,4-diyl, naphthalene-1,8-diyl, and the like. The term "arylene" alone or in combination also include other divalent radicals of the monovalent radicals mentioned in the definition of aryl.

The term "heteroarylene", as used herein, alone or in combination, refers to a five to seven membered aromatic ring diradical, or to a aromatic ring system diradical, containing one or more heteroatoms selected from nitrogen, oxygen, or sulfur heteroatoms, wherein N-oxides and sulfur monoxides and sulfur dioxides are permissible heteroaromatic substitutions. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like. The term "heteroarylene" alone or in combination also include other divalent radicals of the monovalent radicals mentioned in the definition of heteroaryl.

The term "alkylsulfanyl", as used herein, refers to the group $R^aS$—, where $R^a$ is alkyl as described above.

The term "alkylsulfenyl", as used herein, refers to the group $R^aS(O)$—, where $R^a$ is alkyl as described above.

The term "alkylsulfonyl", as used herein, refers to the group $R^aSO_2$—, where $R^a$ is alkyl as described above.

The term "acyl", as used herein, refers to the group $R^aC(O)$—, where $R^a$ is alkyl, alkenyl, alkynyl, cycloalkyl, cycloalkenyl, or heterocyclyl as described above.

The term "aroyl", as used herein, refers to the group $R^aC(O)$—, where $R^a$ is aryl as described above.

The term "heteroaroyl", as used herein, refers to the group $R_aC(O)$—, where $R^a$ is heteroaryl as described above.

The term "aryloxycarbonyl", as used herein, refers to the group $R^a$—O—C(O)—, where $R^a$ is aryl as described above.

The term "acyloxy", as used herein, refers to the group $R^aC(O)O$—, where $R^a$ is alkyl, alkenyl, alkynyl, cycloalkyl, cycloalkenyl, or heterocyclyl as described above.

The term "aryloxy", as used herein refers to the group $R^a$—O—, where $R^a$ is aryl as described above.

The term "aroyloxy", as used herein, refers to the group $R^aC(O)O$—, where $R^a$ is aryl as described above.

The term "heteroaroyloxy", as used herein, refers to the group $R^aC(O)O$—, where $R^a$ is heteroaryl as described above.

Whenever the terms "alkyl", "cycloalkyl", "aryl", "heteroaryl" or the like or either of their prefix roots appear in a name of a substituent (e.g. arylalkoxyaryloxy) they shall be interpreted as including those limitations given above for "alkyl" and "aryl".

As used herein, the term "oxo" shall refer to the substituent =O.

As used herein, the term "mercapto" shall refer to the substituent —SH.

As used herein, the term "carboxy" shall refer to the substituent —COON.

As used herein, the term "cyano" shall refer to the substituent —CN.

As used herein, the term "aminosulfonyl" shall refer to the substituent —$SO_2NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

As used herein, the term "direct bond", where part of a structural variable specification, refers to the direct joining of the substituents flanking (preceding and succeeding) the variable taken as a "direct bond".

The term "lower", as used herein, refers to an group having between one and six carbons, and may be indicated with the prefix $C_{x-6}$—. Lower alkyl may thus be indicated as $C_{1-6}$-alkyl, while lower alkylene may be indicated as $C_{2-6}$-alkylene.

A radical such as $C_{x-y}$-cycloalkyl-$C_{a-b}$-alkenyl shall designate that the radical's point of attachment is in part of the radical mentioned last.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "attached" or "—" (e.g. —$COR^{11}$ which indicates the carbonyl attachment point to the scaffold) signifies a stable covalent bond.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

Certain of the above defined terms may occur more than once in the structural formulae, and upon such occurrence each term shall be defined independently of the other.

As used herein, the term "solvate" is a complex of variable stoichiometry formed by a solute of a compound of the present invention and a solvent. Such solvents for the purpose of the present invention may not interfere with the biological activity of the solute. Solvents may be, by way of example, water, ethanol, or acetic acid.

As used herein, the term "biohydrolyzable ester" is an ester of a drug substance of a compound of the present invention which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to a compound of the present invention in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance of a compound of the present invention which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to a compound of the present invention in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of the present invention and b) compounds which may be oxidized or reduced biologically at a given functional group to yield drug substances of the present invention. Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" or shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" and "treating" as used herein means the management and care of a patient for the purpose of combating a disease, disorder or condition. The term is intended to include the full spectrum of treatments for a given disorder from which the patient is suffering, such as the delaying of the progression of the disease, disorder or condition, the alleviation or relief of symptoms and complications, the prevention of the disease and/or the cure or elimination of the disease, disorder or condition. The patient to be treated is preferably a mammal, in particular a human being.

The term "human insulin" as used herein refers to naturally produced insulin or recombinantly produced insulin. Recombinant human insulin may be produced in any suitable host cell, for example the host cells may be bacterial, fungal (including yeast), insect, animal or plant cells.

The expression "insulin derivative" as used herein (and related expressions) refers to human insulin or an analogue thereof in which at least one organic substituent is bound to one or more of the amino acids.

By "analogue of human insulin" as used herein (and related expressions) is meant human insulin in which one or more amino acids have been deleted and/or replaced by other amino acids, including non-codeable amino acids, or human insulin comprising additional amino acids, i.e. more than 51 amino acids, such that the resulting analogue possesses insulin activity.

The term "acid-stabilised insulin" as used herein refers to an insulin analogue that does not deamidate or dimerize at pH values below 7. Specifically, the analogue cannot have Asn or Asp as a C-terminal residue.

DESCRIPTION OF THE INVENTION

Glucokinase (GK) plays an essential role in blood glucose homeostasis. GK catalyses glucose phosphorylation, and is the rate-limiting reaction for glycolysis in hepatocytes and pancreatic β-cells. In liver GK determine the rates of both glucose uptake and glycogen synthesis, and it is also thought to be essential for the regulation of various glucose-responsive genes (Girard, J. et al., Annu Rev Nutr 17, 325-352 (1997)). In the β-cells, GK determines glucose utilization and thus is necessary for glucose-stimulated insulin secretion. GK is also expressed in a population of neurones in the hypothalamus where it might be involved in feeding behaviour, and in the gut where it might contribute to the secretion of enteroincretins.

GK has two main distinctive characteristics: its expression, which is limited to tissues that require glucose-sensing (mainly liver and pancreatic β-cells), and its $S_{0.5}$ for glucose, which is much higher (8-12 mM) than that of the other members of the hexokinase family. Due to these kinetic characteristics, changes in serum glucose levels are paralleled by changes in glucose metabolism in liver which in turn regulate the balance between hepatic glucose output and glucose consumption.

Activators of glucokinase may thus be useful for treating diseases where increasing the activity of glucokinase is beneficial. Thus, there is a need for agents which activate glucokinase and increase glucokinase enzymatic activity. Such agents would be useful for the treatment of type I diabetes and type II diabetes.

Activators of glucokinase may also play a role in sensing low glucose levels and generating neurohumoral responses to hypoglycemia and may thus be useful for treating those patients with type 1 diabetes, which have a higher tendency to suffer from hypoglycemia.

Type I diabetes mellitus is a complex disease characterized by an elevated blood glucose concentration and polyuria. Secondary to the persistent elevation in blood glucose, patients develop devastating complications such as retinopathy, nephropathy, neuropathy, and cardiovascular disease. A major goal to improve the diabetic phenotype is to reduce fasting and postprandial hyperglycemia and, thus, avoid or delay the onset of diabetic complications. The Diabetes Control and Complications Trial has indicated that tight glycemic control through administration of daily multiple insulin injections delays the onset of complications. However, such intensive therapy is associated with an increase in body weight and higher risk for development of hypoglycaemic events. Alternative treatments to achieve glucose control without these side effects are, therefore, being developed. The combination of GK overexpression in the liver and subcutaneous insulin injections provides better glycemic control in type 1 diabetic animals than treatment with insulin alone (Morral, N., et al. Human Gene Therapy 13, 1561-1570 (2002)). Moreover, overexpression of hepatic GK can compensate, in part, for the metabolic disorders developed by insulin receptor-deficient mice (Jackerott, M. et al. Diabetologia 45, 1292-1297 (2002)).

The present invention also relates to the use of a GK activator for the combined treatment of diabetes and obesity. GK, the GK regulatory protein and the KATP channel are expressed in neurones of the hypothalamus, a region of the brain that is important in the regulation of energy balance and the control of food intake. These neurones have been shown to express orectic and anorectic neuropeptides and have been assumed to be the glucose-sensing neurones within the hypothalamus that are either inhibited or excited by changes in ambient glucose concentrations (Mobbs, C. V. et al, American Journal of Physiology, Endocrinology & Metabolism 281, E649-54 (2001)). The ability of these neurones to sense changes in glucose levels is defective in a variety of genetic and experimentally induced models of obesity (Spanswick, D. et al, Nature Neuroscience 3, 757-8 (2000), Levin, B. E. et al, Brain Research 808, 317-9 (1998)). Intracerebroventricular (icy) infusion of glucose analogues, which are competitive inhibitors of glucokinase, stimulate food intake in lean rats (Kurata, K. et al, Metabolism: Clinical & Experimental 38, 46-51 (1989)). In contrast, icy infusion of glucose suppresses feeding (Kurata, K. et al, Physiology & Behavior 37, 615-20 (1986)). Small molecule activators of GK may thus decrease food intake and weight gain through central effects on GK. Therefore, GK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of type 2 diabetes. Thus the GK/GK regulatory protein system can be described as a potential target of benefit in both diabetes and obesity.

The amplitude of glucose-induce insulin release is highly dependent on the action of the gastrointestinal hormones GLP-1 (glucogen-like peptide 1) and GIP. Unlike sulfonylureas, which stimulate insulin release at low as well as high glucose levels, the action of GLP-1 on β-cells is glucose dependent (Gromada, J. et al., Pflügers Arch 435, 583-594 (1998)). GLP-1 receptor agonist and drugs that slow the degradation of active GLP-1 are therefore under development as a novel treatments for type 2 diabetes. An alternative strategy would be to enhance endogenous GLP-1 levels. Of potential interest is the possibility that the release of GLP-1 and GIP might be regulated by glucokinase-expressing endocrine cells (Jetton, T. L. et al., J. Biol. Chem. 269, 3641-3654 (1994)) and glucose-responsive neurons (Liu, M. et al., J. Neurosci. 19, 10305-10317 (1999)). It has been reported that the release of GIP by intestinal K-cells is directly controlled by glucose (Kieffer, T. J. et al., Am J Physiol 267, E489-E496 (1994)), and GLP-1 secretion from GLUTag cells is triggered by glucose through a mechanism similar to that found in β-cells for insulin secretion (Reimann, F. et al, Diabetes 51, 2757-2763 (2002)). Small molecule activators of glucokinase may thus be used to increase GLP-1 and/or GIP secretion and thus for treatment, modulation, inhibition, decreasion, reduction, arrest or prevention of beta cell degeneration, such as necrosis or apoptosis of β-cells.

The invention is further exemplified by the following embodiments:

Embodiment 1

A compound represented by the general formula (I),

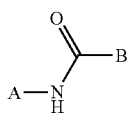

wherein B is

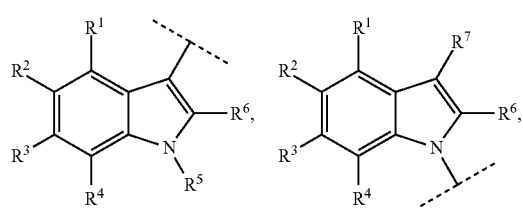

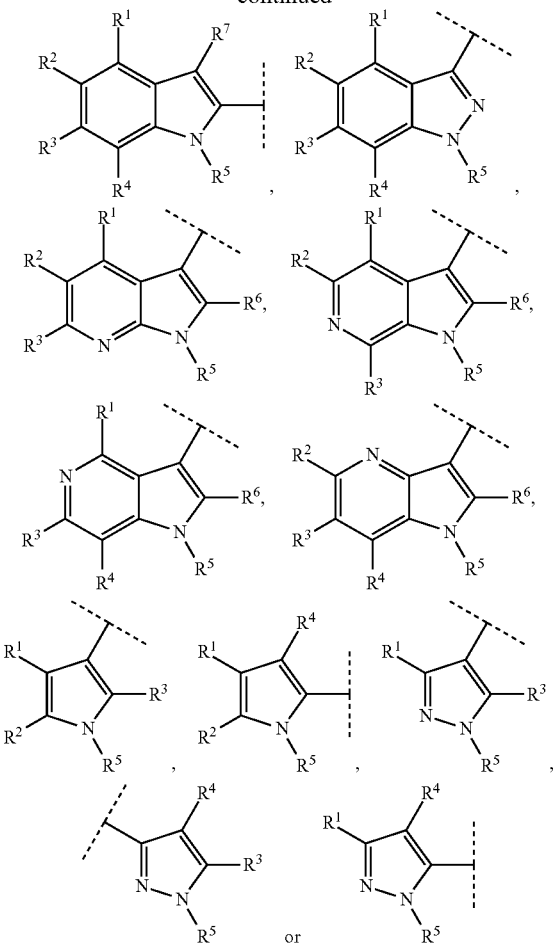

$R^1, R^2, R^3, R^4, R^6$, and $R^7$ are independently selected from the group consisting of hydrogen, halogen, nitro, cyano, hydroxy, carboxy, —$CF_3$; or —$NR^{10}R^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, heteroaryl-$C_{1-6}$-alkyl, $C_{1-6}$-alkoxy, aryl-$C_{1-6}$-alkoxy, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, $C_{1-6}$-alkylsulfonyl, $C_{1-6}$-alkylsulfinyl, arylsulfonyl, heteroarylsulfonyl, aryl, heteroaryl, $C_{1-6}$-alkyl-carbonyl, —C(O)—O—$C_{1-6}$-alkyl, carboxy-$C_{1-6}$-alkyl, hydroxy-$C_{1-6}$-alkyl, carboxy-$C_{1-6}$-alkyloxy, amino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or

—CO—$NR^{13}R^{14}$;

$R^{10}$ and $R^{11}$ independently represent hydrogen, $C_{1-6}$-alkyl, —C(O)—$C_{1-6}$-alkyl, carboxy-$C_{1-6}$-alkyl, —C(O)—$C_{1-6}$-alkyl-C(O)OH, —S(O)$_2$CH$_3$, or aryl;

$R^{12}$ is halogen, cyano, hydroxy, carboxy, —$CF_3$, $C_{1-6}$-alkyl, —S(O)$_2$CH$_3$, or —S(O)$_2$NH$_2$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a heterocycle such as piperazine, homopiperazine or morpholine;

$R^{15}$ is halogen, cyano, hydroxy, carboxy, —$CF_3$, $C_{1-6}$-alkyl, —$S(O)_2CH_3$, or —$S(O)_2NH_2$;

$R^5$ is selected from
- $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, $C_{1-6}$-alkylcarbamoyl-$C_{1-6}$-alkyl, di-($C_{1-6}$-alkyl)carbamoyl-$C_{1-6}$-alkyl, each of which is optionally substituted with one or more substituents independently selected from $R^{32}$; or
- aryl-$C_{1-6}$-alkyl, aryl-C(O)—$C_{1-6}$-alkyl, aryl-O—$C_{1-6}$-alkyl, or aryl-S—$C_{1-6}$-alkyl, wherein the aryl group may be substituted with one or more substituents independently selected from $R^{20}$; or
- heteroaryl-$C_{1-6}$-alkyl, wherein the heteroaryl group may be substituted with one or more substituents independently selected from $R^{26}$; or
- —$C_{1-6}$-alkyl-C(O)—$NR^{28}R^{29}$ or —$C_{1-6}$-alkyl-$NR^{28}R^{29}$; wherein the alkyl part may be substituted with one or more substituents independently selected from $R^{33}$; or
- —C(O)$NR^{30}R^{31}$;

$R^{32}$ and $R^{33}$ are independently halogen, cyano, hydroxy, carboxy, —$CF_3$, $C_{1-6}$-alkyl, —$S(O)_2CH_3$, or —$S(O)_2NH_2$ $R^{20}$ is
- hydrogen, halogen, nitro, cyano, $CF_3$, hydroxy, carboxy; or
- —C(O)—O—$C_{1-6}$-alkyl, $C_{1-6}$-alkoxy, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl each of which is optionally substituted with one or more substituents independently selected from $R^{21}$; or
- —$NR^{22}R^{23}$ or —$C_{1-6}$-alkyl-$NR^{22}R^{23}$ optionally substituted with one or more substituents independently selected from $R^{34}$; or
- —CON$R^{24}R^{25}$;

$R^{21}$ is halogen, nitro, cyano, $CF_3$, hydroxy, $C_{1-6}$-alkyl, —$S(O)_2CH_3$, —$S(O)_2NH_2$ or carboxy;

$R^{22}$ and $R^{23}$ are independently selected from hydrogen, —C(O)—$C_{1-6}$-alkyl or $C_{1-6}$-alkyl;

$R^{24}$ and $R^{25}$ are independently selected from the group consisting of hydrogen, $C_{1-6}$-alkyl, hydroxy-$C_{1-6}$-alkyl, carboxy-$C_{1-6}$-alkyl, aryl or heteroaryl, or $R^{24}$ and $R^{25}$ together with the nitrogen to which they are attached form a heterocycle such as piperazine, homopiperazine or morpholine;

$R^{26}$ is
- hydrogen, halogen, nitro, cyano, hydroxy, carboxy; or
- —C(O)—O—$C_{1-6}$-alkyl, $C_{1-6}$-alkoxy, $C_{1-6}$-alkyl, sulfonyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl, each of which is optionally substituted with one or more substituents independently selected from $R^{27}$;

$R^{27}$ is halogen, nitro, cyano, hydroxy, or carboxy;

$R^{28}$ and $R^{29}$ are independently selected from hydrogen, —C(O)—O—$C_{1-6}$-alkyl, —C(O)—$C_{1-6}$-alkyl or $C_{1-6}$-alkyl;

$R^{30}$ and $R^{31}$ are independently selected from the group consisting of hydrogen, $C_{1-6}$-alkyl, hydroxy-$C_{1-6}$-alkyl, carboxy-$C_{1-6}$-alkyl, aryl, heteroaryl, or $R^{30}$ and $R^{31}$ together with the nitrogen to which they are attached form a heterocycle such as piperazine, homopiperazine or morpholine;

$R^{34}$ is halogen, nitro, cyano, $CF_3$, hydroxy, $C_{1-6}$-alkyl, —$S(O)_2CH_3$, —$S(O)_2NH_2$ or carboxy;

A is heteroaryl which is optionally substituted with one or more substituents selected independently from $R^{40}$, $R^{41}$ and $R^{42}$ $R^{40}$, $R^{41}$ and $R^{42}$ are independently selected from
- halogen, carboxy, cyano, nitro, hydroxy, —$CF_3$, —SCN; or
- $C_{1-6}$-alkyl, $C_{1-6}$-alkoxy, $C_{1-6}$-alkylthio, $C_{1-6}$-alkylamino, di($C_{1-6}$-alkyl)amino, $C_{1-6}$-alkylsulfonyl, $C_{1-6}$-alkylsulfinyl, —C(O)—O—$C_{1-6}$-alkyl, —$NH_2$—C(O)—$C_{1-6}$-alkyl, carboxy-$C_{1-6}$-alkyl, di($C_{1-6}$-alkyl)amino-$C_{1-6}$-alkyl, $C_{1-6}$-alkylamino-$C_{1-6}$-alkyl or hydroxy-$C_{1-6}$-alkyl, each of which is optionally substituted with one or more substituents independently selected from $R^{43}$; or
- aryl, heteroaryl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, aryloxy, heteroaryloxy, arylthio, heteroarylthio, arylsulfonyl, heteroarylsulfonyl, aryl-$C_{1-6}$-alkylamino, each of which is optionally substituted on the aryl or heteroaryl part with one or more substituents independently selected from $R^{44}$; or
- $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{45}$; or
- —$NR^{46}R^{47}$, —$C_{1-6}$-alkyl-$NR^{46}R^{47}$, —$C_{1-6}$-alkyl-S—$R^{48}$—$C_{1-6}$-alkyl-S(O)—$R^{48}$, —$C_{1-6}$-alkyl-S(O)$_2$—$R^{48}$ wherein each alkyl part may be substituted with one or more substituents independently selected from $R^{52}$; or
- —CON$R^{49}R^{50}$, —$C_{1-6}$-alkyl-CON$R^{49}R^{50}$ optionally substituted with one or more substituents independently selected from $R^{53}$; or two of $R^{40}$, $R^{41}$ and $R^{42}$ can be taken together to form a $C_{2-5}$-alkylene bridge;

$R^{43}$, $R^{44}$, and $R^{45}$ are independently $C_{1-6}$-alkyl, halogen, nitro, cyano, hydroxy, carboxy, —$CF_3$, carboxy-$C_{1-6}$-alkyl, —$S(O)_2CH_3$, or —$S(O)_2NH_2$;

$R^{46}$ and $R^{47}$ independently represent hydrogen, $C_{1-6}$-alkyl, hydroxy-$C_{1-6}$-alkyl, carboxy-$C_{1-6}$-alkyl, aryl, heteroaryl or $R^{44}$ and $R^{45}$ together with the nitrogen to which they are attached form a heterocycle such as piperazine, homopiperazine or morpholine;

$R^{48}$ is selected from
- $C_{1-6}$-alkyl, carboxy-$C_{1-6}$-alkyl, $C_{1-6}$-alkylamino-$C_{1-6}$-alkyl or hydroxy-$C_{1-6}$-alkyl; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{51}$; or
- $C_{3-8}$-cycloalkyl, $C_{3-8}$-cycloalkenyl, $C_{3-8}$-cycloalkenyl-$C_{1-6}$-alkyl.

$R^{49}$ and $R^{50}$ are independently selected from hydrogen and $C_{1-6}$-alkyl.

$R^{51}$ is halogen, nitro, cyano, hydroxy, carboxy, —$CF_3$, $C_{1-6}$-alkyl, hydroxy-$C_{1-6}$-alkyl, or carboxy-$C_{1-6}$-alkyl.

$R^{52}$ and $R^{53}$ are independently $C_{1-6}$-alkyl, halogen, nitro, cyano, hydroxy, carboxy, —$CF_3$, —$S(O)_2CH_3$, or —$S(O)_2NH_2$ as well as any salt hereof with a pharmaceutically acceptable acid or base, or any optical isomer or mixture of optical isomers, including a racemic mixture, or any tautomeric forms, with the exception of the compounds
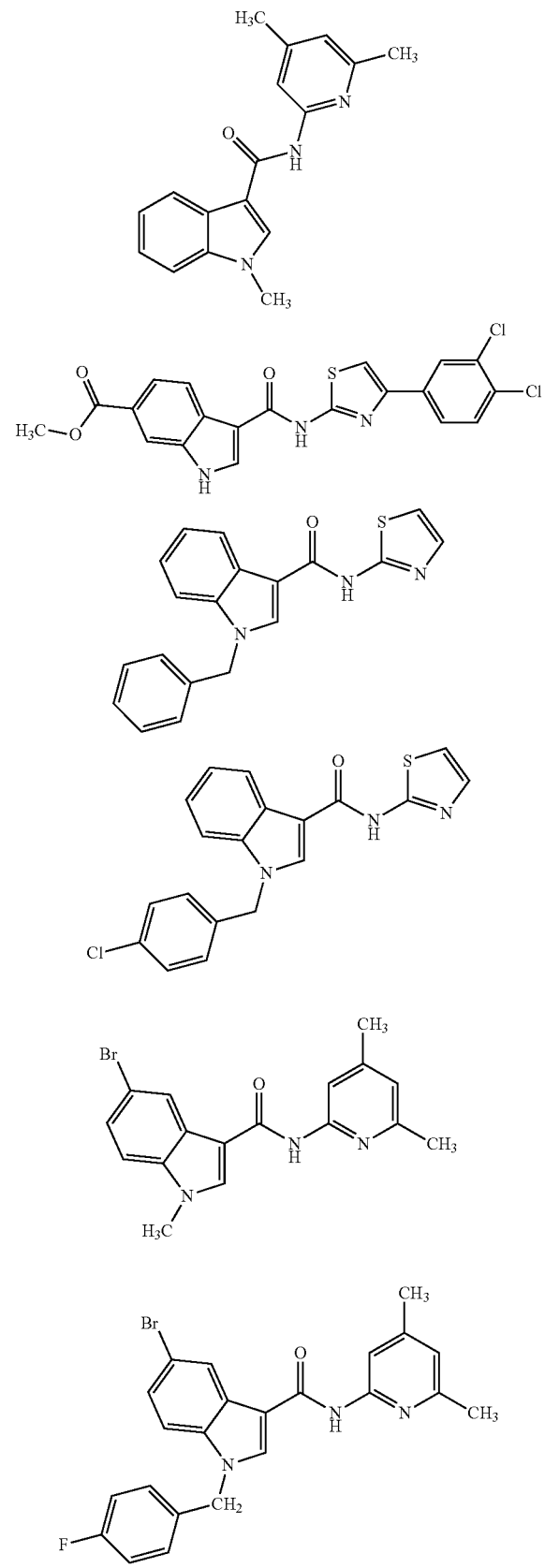
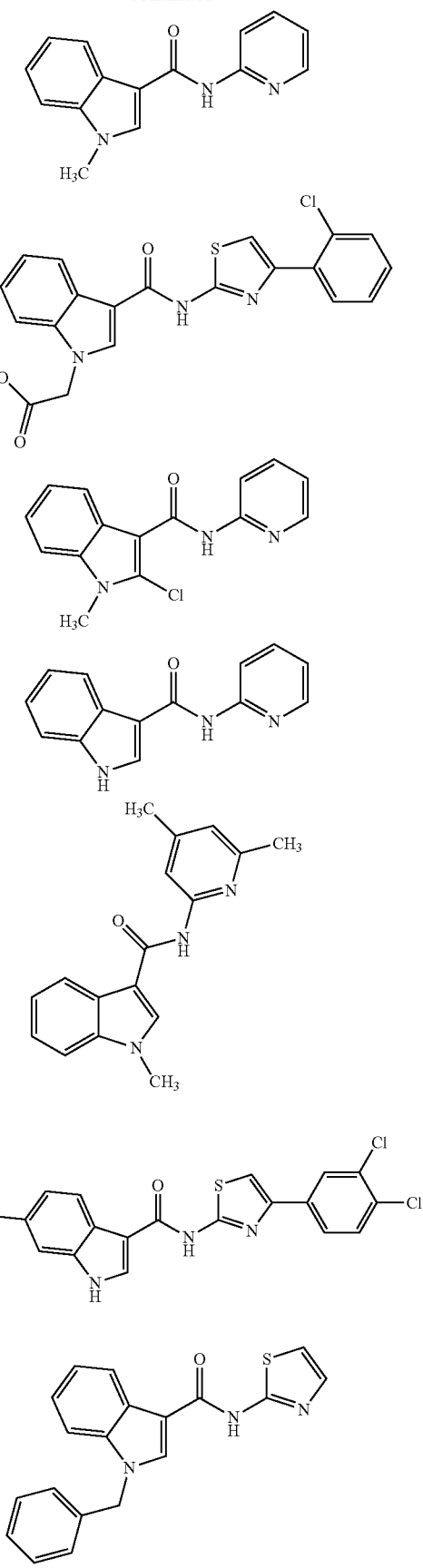

-continued

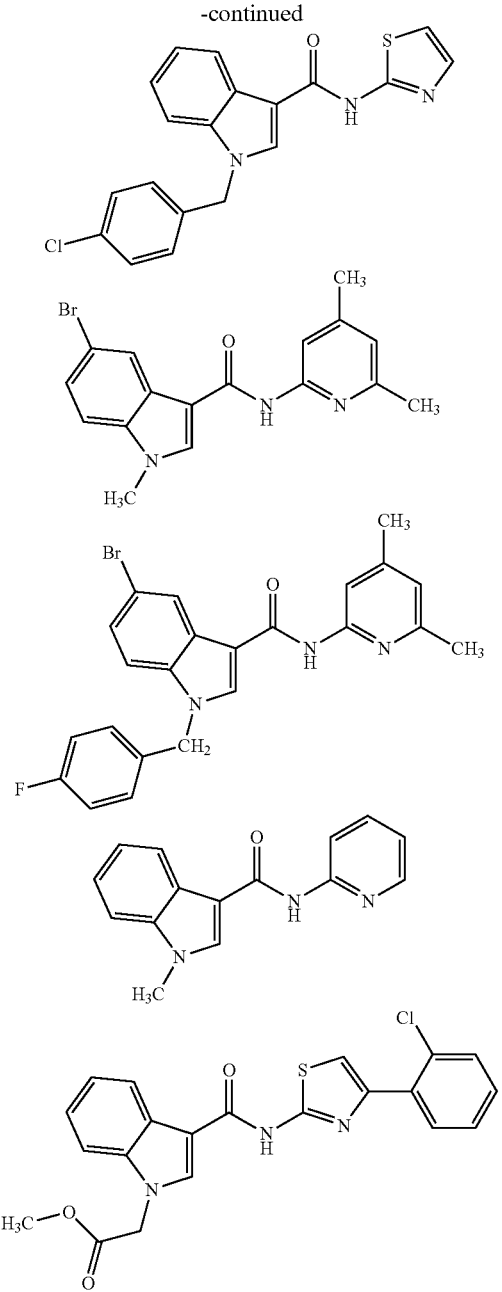

and with the proviso that if A is thiazolyl and B is indolyl, then A cannot be substituted in the 4-position with
  $C_{5-8}$-cycloalkyl optionally substituted with $C_{1-4}$-alkyl,
  aryl optionally substituted with one or more substituents selected from halogen, $C_{1-6}$-alkyl, $C_{1-3}$ alkoxy or $C_{1-3}$ thioalkoxy, nitro, $CF_3$,
  heteroaryl substituted with one or more substituents selected from $C_{1-3}$-alkyl or halogen
and with the proviso that if A is thiadiazolyl and B is unsubstituted indolyl or indolyl substituted on the nitrogen atom with
  —C(O)—$C_{1-4}$-alkyl,
  —$(CH_2)_n$C(O)R wherein n is 1 or 2 and R is $OR^{1'}$ or $NR^{1'}R^{2'}$, $R^{1'}R^{2'}$ being selected from H or $C_{1-4}$-alkyl,
  Hydroxy-$C_{1-4}$-alkyl,
  $C_{2-6}$ alkoxyalkyl,
  tetrahydropyranyl, then A cannot be substituted in the 3-position with
  phenyl, pyridine, or pyrimidine, each of which may optionally be substituted with up to four substituents selected from Cl, Br, $C_{1-3}$-alkyl, or $C_{1-3}$-alkoxy and $CF_3$,
  naphtyl optionally substituted with halogen, $C_{1-3}$-alkyl, or $C_{1-3}$-alkoxy.

Embodiment 2

A compound according to embodiment 1 wherein B is

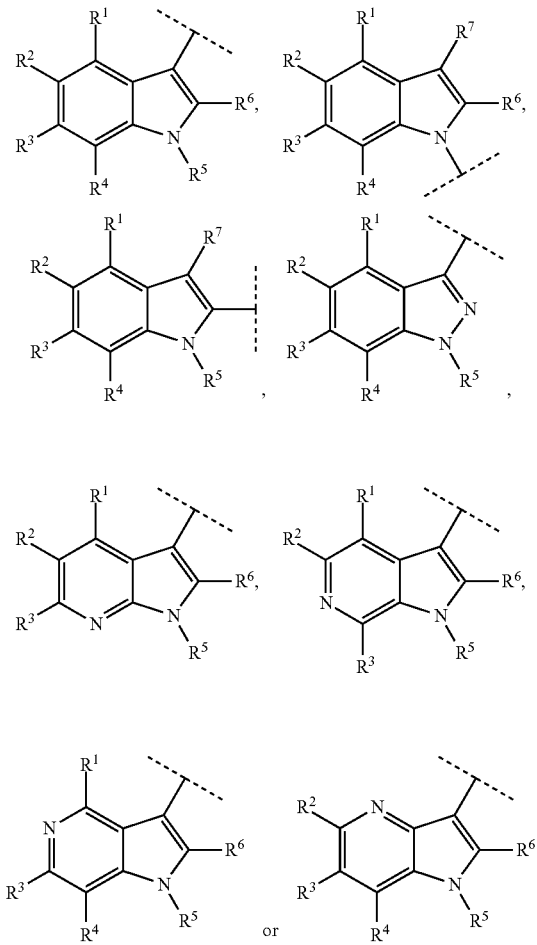

Embodiment 3

A compound according to embodiment 2 wherein B is

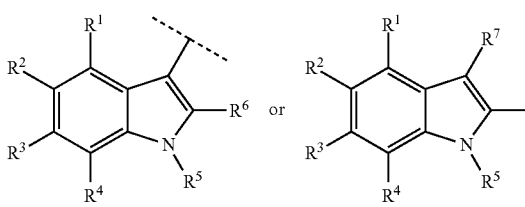

Embodiment 4

A compound according to embodiment 3 wherein B is

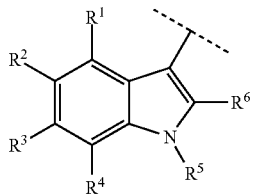

Embodiment 5

A compound according to embodiment 4 wherein B is

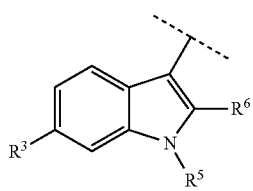

Embodiment 6

A compound according to embodiment 3 wherein B is

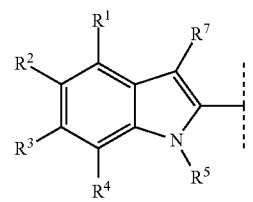

Embodiment 7

A compound according to embodiment 6 wherein B is

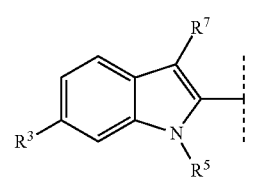

Embodiment 8

A compound according to any one of the embodiments 1 to 7 wherein at least one of the substituents $R^1$, $R^2$, $R^3$ and $R^4$ is different from H.

Embodiment 9

A compound according to embodiment 8 wherein $R^3$ is different from H.

Embodiment 10

A compound according to any one of the embodiments 1 to 9 wherein A is thiazolyl, oxazolyl, isoxazolyl, 1,3,4-thiadiazolyl-1,2,4-thiadiazolyl, 1,3,4-oxadiazolyl, 1,2,4-oxadiazolyl, pyrazolyl, 1,2,4-triazolyl, tetrazolyl, 3-oxo-pyrazolyl, 3-oxo-imidazolyl, 3-oxo-thiazolyl, thiazolidinyl, pyridyl, pyrimidinyl, pyrazinyl, 1,3,5-triazinyl, 1,2,4-triazinyl, benzimidazolyl, 4-oxo-pyrimidyl, pyridazinyl or 2-oxo-pyrimidyl, each of which may optionally be substituted with one or more substituents independently selected from $R^{40}$, $R^{41}$ and $R^{42}$.

Embodiment 11

A compound according to embodiment 10 wherein A is thiazolyl, 1,3,4-thiadiazolyl 1,2,4-thiadiazolyl, pyridyl, or pyrimidinyl, each of which may optionally be substituted with one or more substituents independently selected from $R^{40}$, $R^{41}$ and $R^{42}$.

Embodiment 12

A compound according to embodiment 11 wherein A is thiazolyl or 1,2,4-thiadiazolyl, each of which may optionally be substituted with one or more substituents independently selected from $R^{40}$, $R^{41}$ and $R^{42}$.

Embodiment 13

A compound according to embodiment 11 wherein A is

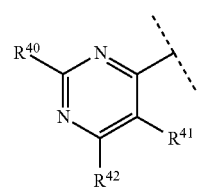

Embodiment 14

A compound according to embodiment 12 wherein A is

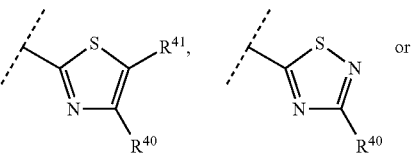

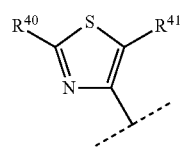

Embodiment 15

A compound according to embodiment 14 wherein A is

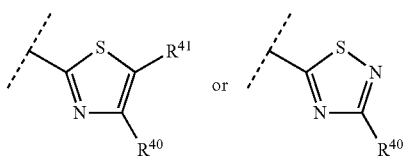

Embodiment 16

A compound according to embodiment 15 wherein A is

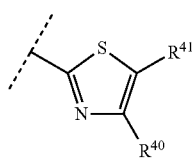

Embodiment 17

A compound according to embodiment 15 wherein A is

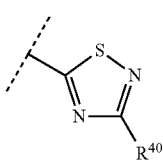

Embodiment 18

A compound according to any one of the embodiments 1 to 17 wherein $R^6$ and $R^7$ are hydrogen.

Embodiment 19

A compound according to any one of the embodiments 1 to 18 wherein $R^1$, $R^2$, $R^3$ and $R^4$ are independently selected from the group consisting of hydrogen, halogen, cyano, hydroxy, carboxy, —$CF_3$; or
—$NR^{10}R^{11}$; or
$C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, heteroaryl-$C_{1-6}$-alkyl, $C_{1-6}$-alkoxy, aryl-$C_{1-6}$-alkoxy, aryloxy, heteroaryloxy, $C_{1-6}$-alkylthio, $C_{1-6}$-alkylsulfonyl, $C_{1-6}$-alkylsulfinyl, aryl, heteroaryl, $C_{1-6}$-alkyl-carbonyl, carboxy-$C_{1-6}$-alkyl, hydroxy-$C_{1-6}$-alkyl, di($C_{1-6}$-alkyl)amino-$C_{1-6}$-alkyl, $C_{1-6}$-alkylamino-$C_{1-6}$-alkyl, or carboxy-$C_{1-6}$-alkyloxy, each of which is optionally substituted with one or more substituents independently selected from $R^{12}$; or
—CO—$NR^{13}R^{14}$.

Embodiment 20

A compound according to embodiment 19 wherein $R^1$, $R^2$, $R^3$ and $R^4$ are independently selected from the group consisting of hydrogen, halogen, cyano, hydroxy, carboxy, —$CF_3$; or
—$NR^{10}R^{11}$; or
$C_{1-6}$-alkyl, benzyl, $C_{1-6}$-alkoxy, benzyloxy, phenyl, $C_{1-6}$-alkyl-carbonyl, carboxy-$C_{1-6}$-alkyl, hydroxy-$C_{1-6}$-alkyl, di($C_{1-6}$-alkyl)amino-$C_{1-6}$-alkyl, $C_{1-6}$-alkylamino-$C_{1-6}$-alkyl or carboxy-$C_{1-6}$-alkyloxy, each of which is optionally substituted with one or more substituents independently selected from $R^{12}$; or
—CO—$NR^{13}R^{14}$.

Embodiment 21

A compound according to embodiment 20 wherein $R^1$, $R^2$, $R^3$ and $R^4$ are independently selected from the group consisting of hydrogen, halogen, hydroxy, carboxy, —$CF_3$; or
—$NR^{10}R^{11}$; or
$C_{1-6}$-alkyl, carboxy-$C_{1-6}$-alkyl, hydroxy-$C_{1-6}$-alkyl, di($C_{1-6}$-alkyl)amino-$C_{1-6}$-alkyl, $C_{1-6}$-alkylamino-$C_{1-6}$-alkyl or carboxy-$C_{1-6}$-alkyloxy, each of which is optionally substituted with one or more substituents independently selected from $R^{12}$; or
—CO—$NR^{13}R^{14}$.

Embodiment 22

A compound according to embodiment 21 wherein $R^1$, $R^2$, $R^3$ and $R^4$ are independently selected from the group consisting of hydrogen, F, Cl, Br, hydroxy, carboxy, —$CF_3$; or
—$NR^{10}R^{11}$; or
methyl, ethyl, propyl, —$CH_2$—C(O)OH, —$(CH_2)_2$—C(O)OH, —$CH_2$—OH, —$(CH_2)_2$—OH, —O—$CH_2$—C(O)OH, —$(CH_2)_2$—$N(CH_3)_2$, —O—$(CH_2)_2$—C(O)OH; or
CO—$NR^{13}R^{14}$.

Embodiment 23

A compound according to any one of the embodiments 1 to 22 wherein $R^{10}$ and $R^{11}$ independently represent hydrogen, methyl, —C(O)—$CH_3$, —C(O)—$CH_2CH_3$, —$CH_2$—C(O)OH, —$(CH_2)_2$—C(O)OH, —C(O)—$CH_2$—C(O)OH, or —$S(O)_2CH_3$.

Embodiment 24

A compound according to embodiment 23 wherein $R^{10}$ is H and $R^{11}$ is hydrogen, methyl, —C(O)—$CH_3$, —C(O)—$CH_2CH_3$, —$CH_2$—C(O)OH, —$(CH_2)_2$—C(O)OH, —C(O)—$CH_2$—C(O)OH, or —$S(O)_2CH_3$.

Embodiment 25

A compound according to any one of the embodiments 1 to 24 wherein $R^{12}$ is halogen.

Embodiment 26

A compound according to any one of the embodiments 1 to 25 wherein $R^{13}$ and $R^{14}$ are independently selected from the group consisting of hydrogen, methyl, ethyl, or propyl.

Embodiment 27

A compound according to embodiment 26 wherein both $R^{13}$ and $R^{14}$ are hydrogen, or both are methyl, or both are ethyl, or both are propyl.

Embodiment 28

A compound according to any one of the embodiments 1 to 25 wherein $R^{13}$ and $R^{14}$ together with the nitrogen to which they are attached form a morpholine ring.

Embodiment 29

A compound according to any one of the embodiments 1 to 28 wherein $R^{15}$ is halogen.

Embodiment 30

A compound according to any one of the embodiments 1 to 29 wherein $R^5$ is selected from
- $C_{1-6}$-alkyl, $C_{2-6}$-alkenyl, $C_{2-6}$-alkynyl, $C_{3-8}$-cycloalkyl-$C_{1-6}$-alkyl, $C_{3-8}$-cycloalkenyl-$C_{1-6}$-alkyl, cyanomethyl, carboxymethyl, $C_{1-6}$-alkylcarbamoyl-$C_{1-6}$-alkyl, di-($C_{1-6}$-alkyl)carbamoyl-$C_{1-6}$-alkyl; each of which may optionally be substituted with one or more substituents independently selected from $R^{32}$; or
- phenyl-$C_{1-6}$-alkyl, wherein the phenyl group may be substituted with one or more substituents independently selected from $R^{20}$; or
- Heteroaryl-$C_{1-6}$-alkyl, wherein the heteroaryl part is selected from furyl, thienyl, pyrrolyl, pyrazolyl, 3-oxopyrazolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl, thiazolidinyl, 2-thiooxothiazolidinyl, and the heteroaryl group may be substituted with one or more substituents independently selected from $R^{26}$; or
- —$C_{1-6}$-alkyl-$NR^{28}R^{29}$; or
- —$CONR^{39}R^{31}$.

Embodiment 31

A compound according to embodiment 30 wherein $R^5$ is selected from
- $C_{1-6}$-alkyl, $C_{2-6}$-alkenyl, $C_{2-6}$-alkynyl, $C_{3-8}$-cycloalkyl-$C_{1-6}$-alkyl, $C_{3-8}$-cycloalkenyl-$C_{1-6}$-alkyl, cyanomethyl, carboxymethyl, $C_{1-6}$-alkylcarbamoylmethyl, di-($C_{1-6}$-alkyl)carbamoylmethyl; each of which may optionally be substituted with one or more substituents independently selected from $R^{32}$; or
- Phenyl-$C_{1-6}$-alkyl, wherein the phenyl group may be substituted with one or more substituents independently selected from $R^{20}$; or
- Heteroaryl-$C_{1-6}$-alkyl, wherein the heteroaryl part is selected from furyl, thienyl, pyrrolyl, pyrazolyl, oxazolyl, thiazolyl, imidazolyl, 1,2,3-triazolyl, 1,2,4-triazolyl, pyranyl, pyridyl, pyrimidinyl, 1,2,3-thiadiazolyl, 1,2,4-thiadiazolyl, 1,2,5-thiadiazolyl, 1,3,4-thiadiazolyl, indolyl, isoindolyl, benzofuryl, benzothienyl, benzimidazolyl, benzoxazolyl, purinyl, quinolinyl, isoquinolinyl, or thiazolidinyl, and the heteroaryl group may be substituted with one or more substituents independently selected from $R^{26}$; or
- —$C_{1-6}$-alkyl-$NR^{28}R^{29}$; or
- —$CONR^{39}R^{31}$.

Embodiment 32

A compound according to embodiment 31 wherein $R^5$ is selected from
- $C_{1-6}$-alkyl, $C_{2-6}$-alkenyl, $C_{2-6}$-alkynyl, $C_{3-8}$-cycloalkenyl-$C_{1-6}$-alkyl, $C_{3-8}$-cycloalkenyl-$C_{1-6}$-alkyl, each of which may optionally be substituted with one or more substituents independently selected from $R^{32}$; or
- Phenyl-$C_{1-6}$-alkyl, wherein the phenyl group may be substituted with one or more substituents independently selected from $R^{20}$; or
- —$C_{1-6}$-alkyl-$NR^{28}R^{29}$; or
- —$CONR^{39}R^{31}$.

Embodiment 33

A compound according to embodiment 32 wherein $R^5$ is selected from
- $C_{1-6}$-alkyl, $C_{2-6}$-alkenyl, $C_{2-6}$-alkynyl, $C_{3-8}$-cycloalkenyl-$C_{1-6}$-alkyl, each of which may optionally be substituted with one or more substituents independently selected from $R^{32}$; or
- Phenyl-$C_{1-6}$-alkyl, wherein the phenyl group may be substituted with one or more substituents independently selected from $R^{20}$.

Embodiment 34

A compound according to embodiment 33 wherein $R^5$ is selected from
- methyl, ethyl, propyl, isopropyl, butyl, isobutyl, sec-butyl, tert-butyl, n-pentyl, isopentyl, neopentyl, tert-pentyl, wherein each alkyl is optionally substituted with one or more substituents independently selected from $R^{32}$, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, ethynyl, 1-propynyl, 2-propynyl, 1-butynyl, 2-butynyl, 3-butynyl, 1-pentynyl, 2-pentynyl, 3-pentynyl, 4-pentynyl,

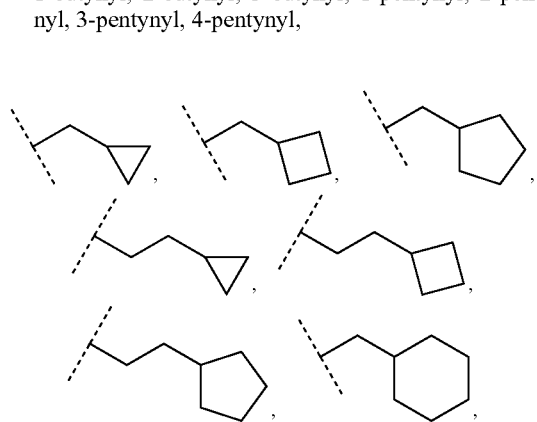

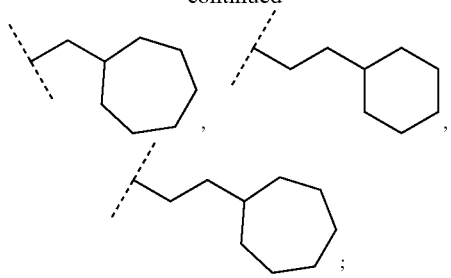

or

Phenyl-$C_{1-6}$-alkyl, wherein the phenyl group may be substituted with one or more substituents independently selected from $R^{20}$.

Embodiment 35

A compound according to embodiment 34 wherein $R^5$ is selected from
methyl, ethyl, propyl, isopropyl, butyl, isobutyl, sec-butyl, tert-butyl, wherein each alkyl is optionally substituted with one or more substituents independently selected from $R^{32}$, vinyl, 1-propenyl, 2-propenyl, iso-propenyl, 1,3-butadienyl, 1-butenyl, 2-butenyl, 3-butenyl, 2-methyl-1-propenyl, 3-methyl-2-butenyl,

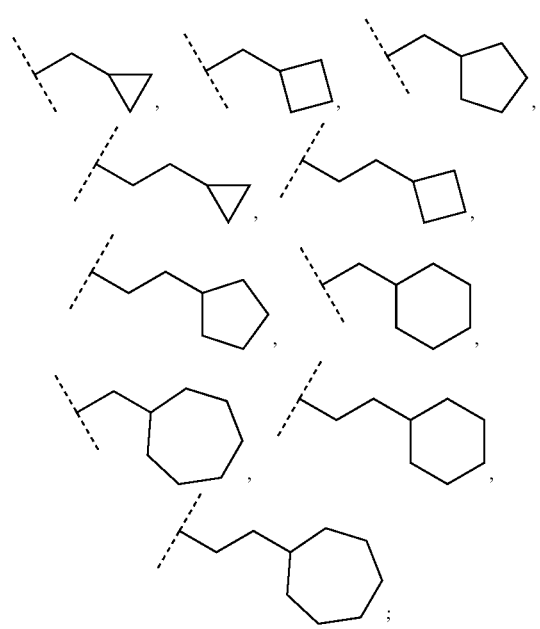

or

Phenyl-$C_{1-6}$-alkyl, wherein the phenyl group may be substituted with one or more substituents independently selected from $R^{20}$.

Embodiment 36

A compound according to embodiment 35 wherein $R^5$ is selected from
methyl, ethyl, propyl, wherein each alkyl is optionally substituted with one or more substituents independently selected from $R^{32}$, 1-propenyl, 2-propenyl, iso-propenyl, 2-methyl-1-propenyl, 3-methyl-2-butenyl,

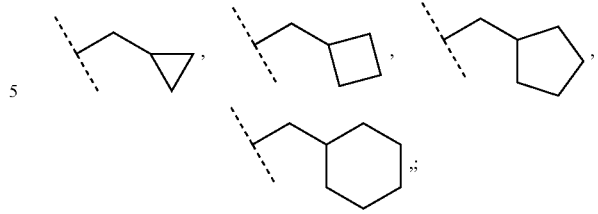

or

Benzyl, wherein the phenyl part may be substituted with one or more substituents independently selected from $R^{20}$.

Embodiment 37

A compound according to any one of the embodiments 1 to 36 wherein $R^{20}$ is
halogen, cyano, $CF_3$, hydroxy, carboxy; or
—C(O)—O—$C_{1-6}$-alkyl, $C_{1-6}$-alkoxy, $C_{1-6}$-alkyl, $C_{1-6}$-alkylthio, $C_{1-6}$-alkylsulfonyl, carboxy-$C_{1-6}$-alkyl, amino-$C_{1-6}$-alkyl, hydroxy-$C_{1-6}$-alkyl, each of which is optionally substituted with one or more substituents independently selected from $R^{21}$; or
—$NR^{22}R^{23}$, —$C_{1-6}$-alkyl-$NR^{22}R^{23}$; or
—$CONR^{24}R^{25}$.

Embodiment 38

A compound according to embodiment 37 wherein $R^{20}$ is
halogen, cyano, $CF_3$, hydroxy, carboxy; or
—C(O)—O—$C_{1-6}$-alkyl, $C_{1-6}$-alkoxy, $C_{1-6}$-alkyl, carboxy-$C_{1-6}$-alkyl, amino-$C_{1-6}$-alkyl, hydroxy-$C_{1-6}$-alkyl; or
—$NR^{22}R^{23}$ or
—$CONR^{24}R^{25}$.

Embodiment 39

A compound according to embodiment 38 wherein $R^{20}$ is
halogen, cyano, $CF_3$, hydroxy, carboxy; or
$C_{1-6}$-alkoxy, $C_{1-6}$-alkyl, carboxy-$C_{1-6}$-alkyl, amino-$C_{1-6}$-alkyl, hydroxy-$C_{1-6}$-alkyl.

Embodiment 40

A compound according to embodiment 39 wherein $R^{20}$ is halogen, cyano, $CF_3$, hydroxy, carboxy, —O—$CH_3$, —O—$(CH_3)_2$, methyl, ethyl, or propyl.

Embodiment 41

A compound according to any one of the embodiments 1 to 40 wherein $R^{21}$ is halogen.

Embodiment 42

A compound according to any one of the embodiments 1 to 41 wherein $R^{22}$ and $R^{23}$ are independently selected from hydrogen, —C(O)—$CH_2$, methyl, ethyl or propyl.

Embodiment 43

A compound according to any one of the embodiments 1 to 42 wherein $R^{24}$ and $R^{25}$ are independently selected from the group consisting of hydrogen, methyl, ethyl or propyl.

Embodiment 44

A compound according to any one of the embodiments 1 to 43 wherein $R^{26}$ is
halogen, nitro, cyano, hydroxy, carboxy; or
—C(O)—O—$C_{1-6}$-alkyl, $C_{1-6}$-alkoxy, $C_{1-6}$-alkyl, each of which is optionally substituted with one or more substituents independently selected from $R^{27}$.

Embodiment 45

A compound according to embodiment 44 wherein $R^{26}$ is halogen, cyano, hydroxy, carboxy, methoxy, ethoxy, methyl, ethyl or propyl.

Embodiment 46

A compound according to any one of the embodiments 1 to 45 wherein $R^{27}$ is halogen.

Embodiment 47

A compound according to any one of the embodiments 1 to 46 wherein $R^{28}$ and $R^{29}$ are independently selected from hydrogen or methyl.

Embodiment 48

A compound according to any one of the embodiments 1 to 47 wherein $R^{30}$ and $R^{31}$ are independently selected from hydrogen or methyl.

Embodiment 49

A compound according to any one of the embodiments 1 to 48 wherein $R^{32}$ is halogen or cyano.

Embodiment 50

A compound according to embodiment 49 wherein $R^{32}$ is halogen.

Embodiment 51

A compound according to any one of the embodiments 1 to 50 wherein $R^{40}$, $R^{41}$ and $R^{42}$ are independently selected from
halogen, carboxy, cyano, hydroxy, —$CF_3$, —SCN; or
$C_{1-6}$-alkyl, $C_{1-6}$-alkoxy, $C_{1-6}$-alkylthio, —C(O)—$C_{1-6}$-alkyl, —$C_{1-6}$-alkyl-O—$C_{1-6}$-alkyl, —$C_{1-6}$-alkyl-S—$C_{1-6}$-alkyl, carboxy-$C_{1-6}$-alkyl, di($C_{1-6}$-alkyl)amino-$C_{1-6}$-alkyl, $C_{1-6}$-alkylamino-$C_{1-6}$-alkyl, or hydroxy-$C_{1-6}$-alkyl, each of which is optionally substituted with one or more substituents independently selected from $R^{43}$; or
phenyl-$C_{1-6}$-alkyl, naphtyl-$C_{1-6}$-alkyl, heteroaryl-$C_{1-6}$-alkyl, phenyl-$C_{1-6}$-alkylthio, naphtyl-$C_{1-6}$-alkylthio, heteroaryl-$C_{1-6}$-alkylthio, heteroaryl-thio-$C_{1-6}$-alkyl, phenyloxy, heteroaryloxy, or heteroarylthio, wherein each heteroaryl part is selected from furyl, thienyl, pyrrolyl, pyrazolyl, oxazolyl, thiazolyl, imidazolyl, 1,2,3-triazolyl, 1,2,4-triazolyl, pyranyl, pyridyl, pyrimidinyl, 1,2,3-thiadiazolyl, 1,2,4-thiadiazolyl, 1,2,5-thiadiazolyl, 1,3,4-thiadiazolyl, indolyl, isoindolyl, benzofuryl, benzothienyl, benzimidazolyl, benzoxazolyl, purinyl, quinolinyl, isoquinolinyl, or thiazolidinyl, and wherein each aryl or heteroaryl part is optionally substituted with one or more substituents independently selected from $R^{44}$; or
$C_{3-8}$-cycloalkyl, $C_{3-8}$-cycloalkyl-$C_{1-6}$-alkyl, each of which is optionally substituted on the cycloalkyl part with one or more substituents independently selected from $R^{45}$; or
—$NR^{46}R^{47}$, —$C_{1-6}$-alkyl-$NR^{46}R^{47}$, —$C_{1-6}$-alkyl-S(O)—$R^{48}$, —$C_{1-6}$-alkyl-S(O)$_2$—$R^{48}$ wherein each alkyl part may be substituted with one or more substituents independently selected from $R^{52}$;
two of $R^{40}$, $R^{41}$ and $R^{42}$ can be taken together to form a $C_{2-5}$-alkylene bridge.

Embodiment 52

A compound according to embodiment 51 wherein $R^{40}$, $R^{41}$ and $R^{42}$ are independently selected from
halogen, cyano, —$CF_3$, —SCN; or
methyl, ethyl propyl, butyl, methoxy, ethoxy, —C(O)—$CH_3$, —C(O)—$CH_2CH_3$, —$CH_2OH$, —$CH_2CH_2OH$, —$(CH_2)_2$—$N(CH_3)_2$, —$CH_2$—O—$CH_2$, —$CH_2CH_2$—O—$CH_2$, —$CH_2$—S—$CH_2$, —$CH_2CH_2$—S—$CH_2$; or
phenyl-methyl, phenyl-ethyl, naphtyl-methyl, naphtyl-ethyl, heteroaryl-methyl, heteroaryl-ethyl, phenyl-methylthio, phenyl-ethylthio, heteroaryl-methylthio, heteroaryl-ethylthio, heteroaryl-thio-methyl, heteroaryl-thio-ethyl, each of which is optionally substituted on the aryl or heteroaryl part with one or more substituents independently selected from $R^{44}$ and wherein heteroaryl is selected from

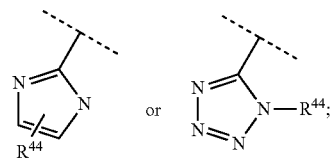

or
Cyclopropyl, cyclobutyl, cyclopentyl, cyclohexyl, cyclopropyl-methyl, cyclobutyl-methyl, cyclopentyl-methyl, cyclohexyl-methyl, cyclopropyl-ethyl, cyclobutyl-ethyl, cyclopentylethyl, cyclohexyl-ethyl, each of which is optionally substituted on the cycloalkyl part with one or more substituents independently selected from $R^{45}$; or
two of $R^{40}$, $R^{41}$ and $R^{42}$ can be taken together to form a $C_{2-5}$-alkylene bridge.

Embodiment 53

A compound according to embodiment 52 wherein $R^{40}$, $R^{41}$ and $R^{42}$ are independently selected from
halogen, cyano, —$CF_3$, —SCN; or
methyl, ethyl, —C(O)—$CH_3$, —$CH_2OH$, —$CH_2CH_2OH$, —$CH_2$—O—$CH_2$, —$CH_2CH_2$—O—$CH_2$, —$CH_2$—S—$CH_2$, —$CH_2CH_2$—S—$CH_2$; or
heteroaryl-methyl, heteroaryl-ethyl, phenyl-methylthio, phenyl-ethylthio, heteroaryl-thio-methyl, heteroaryl-thio-ethyl, each of which is optionally substituted on the aryl or heteroaryl part with one or more substituents independently selected from $R^{44}$ and wherein heteroaryl is selected from

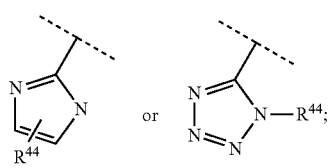

or
Cyclopropyl, cyclobutyl, cyclopentyl, cyclohexyl, cyclopropyl-methyl, cyclobutyl-methyl, cyclopentyl-methyl, cyclohexyl-methyl, cyclopropyl-ethyl, cyclobutyl-ethyl, cyclopentylethyl, cyclohexyl-ethyl, each of which is optionally substituted on the cycloalkyl part with one or more substituents independently selected from $R^{45}$; or two of $R^{40}$, $R^{41}$ and $R^{42}$ can be taken together to form a $C_{2-5}$-alkylene bridge.

Embodiment 54

A compound according to embodiment 53 wherein $R^{40}$, $R^{41}$ and $R^{42}$ are independently selected from
halogen, cyano, —$CF_3$, —SCN; or
methyl, ethyl, —C(O)—$CH_3$, —$CH_2OH$, —$CH_2CH_2OH$, —$CH_2$—O—$CH_2$, —$CH_2CH_2$—O—$CH_2$, —$CH_2$—S—$CH_2$, —$CH_2CH_2$—S—$CH_2$; or

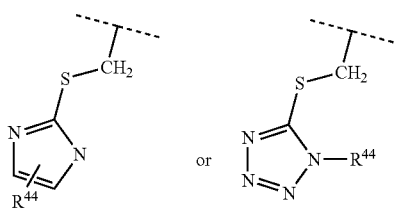

Embodiment 55

A compound according to any one of the embodiments 1 to 54 wherein $R^{43}$ is $C_{1-6}$-alkyl, halogen, cyano, hydroxy, carboxy, or —$CF_3$.

Embodiment 56

A compound according to embodiment 55 wherein $R^{43}$ is methyl, ethyl or halogen.

Embodiment 57

A compound according to any one of the embodiments 1 to 56 wherein $R^{44}$ is $C_{1-6}$-alkyl, halogen, nitro, cyano, hydroxy, carboxy, —$CF_3$, or carboxy-$C_{1-6}$-alkyl.

Embodiment 58

A compound according to embodiment 57 wherein $R^{44}$ is methyl, ethyl, halogen, —$CH_2$—COOH, or —$CH_2$—$CH_2$—COOH.

Embodiment 59

A compound according to any one of the embodiments 1 to 58 wherein $R^{45}$ is $C_{1-6}$-alkyl, halogen, nitro, cyano, hydroxy, carboxy, —$CF_3$, or carboxy-$C_{1-6}$-alkyl.

Embodiment 60

A compound according to embodiment 59 wherein $R^{45}$ is methyl, ethyl, halogen, —$CH_2$—COOH, or —$CH_2$—$CH_2$—COOH.

Embodiment 61

A compound according to any one of the embodiments 1 to 60 wherein $R^{46}$ and $R^{47}$ independently represent hydrogen, methyl, ethyl, hydroxy-methyl, hydroxy-methyl, carboxy-methyl, carboxy-ethyl, or phenyl, or $R^{44}$ and $R^{45}$ together with the nitrogen to which they are attached form a heterocycle selected from piperazine, homopiperazine or morpholine.

Embodiment 62

A compound according embodiment 61 wherein $R^{46}$ and $R^{47}$ independently represent hydrogen, methyl, ethyl, or phenyl, or $R^{44}$ and $R^{45}$ together with the nitrogen to which they are attached form a heterocycle selected from piperazine, homopiperazine or morpholine.

Embodiment 63

A compound according to any one of the embodiments 1 to 62 wherein $R^{48}$ is selected from
carboxy-methyl, carboxy-ethyl, hydroxy-methyl or hydroxy-ethyl; or
phenyl, naphtyl, heteroaryl, phenylmethyl, phenylethyl, heteroaryl-methyl or heteroaryl-methyl, wherein each heteroaryl part is selected from furyl, thienyl, pyrrolyl, pyrazolyl, oxazolyl, thiazolyl, imidazolyl, 1,2,3-triazolyl, 1,2,4-triazolyl, pyranyl, pyridyl, pyrimidinyl, 1,2,3-thiadiazolyl, 1,2,4-thiadiazolyl, 1,2,5-thiadiazolyl, 1,3,4-thiadiazolyl, indolyl, isoindolyl, benzofuryl, benzothienyl, benzimidazolyl, benzoxazolyl, purinyl, quinolinyl, isoquinolinyl, tetrazolyl, or thiazolidinyl, and wherein the aryl or heteroaryl part is optionally substituted with one or more substituents independently selected from $R^{51}$; or
$C_{3-8}$-cycloalkyl, $C_{3-8}$-cycloalkyl-methyl or $C_{3-8}$-cycloalkyl-ethyl.

Embodiment 64

A compound according to embodiment 63 wherein $R^{48}$ is selected from
carboxy-methyl, carboxy-ethyl, hydroxy-methyl or hydroxy-ethyl; or
phenyl, heteroaryl, phenylmethyl, phenylethyl, heteroaryl-methyl or heteroaryl-methyl, wherein each heteroaryl part is selected from imidazolyl, 1,2,3-triazolyl, 1,2,4-triazolyl, or tetrazolyl, and wherein the aryl or heteroaryl part is optionally substituted with one or more substituents independently selected from $R^{51}$; or
Cyclopropyl, cyclobutyl, cyclopentyl, cyclohexyl, cyclopropyl-methyl, cyclobutyl-methyl, cyclopentyl-methyl, cyclohexyl-methyl, cyclopropyl-ethyl, cyclobutyl-ethyl, cyclopentylethyl, or cyclohexyl-ethyl.

Embodiment 65

A compound according to embodiment 64 wherein $R^{48}$ is selected from
- carboxy-methyl, carboxy-ethyl, hydroxy-methyl or hydroxy-ethyl; or
- phenyl, heteroaryl, phenylmethyl, phenylethyl, heteroaryl-methyl or heteroaryl-methyl, wherein each heteroaryl part is selected from imidazolyl, 1,2,3-triazolyl, 1,2,4-triazolyl, or tetrazolyl, and wherein the aryl or heteroaryl part is optionally substituted with one or more substituents independently selected from $R^{51}$; or
- Cyclopropyl, cyclobutyl, or cyclopentyl.

Embodiment 66

A compound according to any one of the embodiments 1 to 65 wherein $R^{49}$ and $R^{50}$ are independently selected from hydrogen, methyl and ethyl.

Embodiment 67

A compound according to embodiment 66 wherein $R^{49}$ and $R^{50}$ are both hydrogen.

Embodiment 68

A compound according to any one of the embodiments 1 to 67 wherein $R^{51}$ is halogen, cyano, hydroxy, carboxy, —$CF_3$, methyl, ethyl, hydroxy-methyl, hydroxy-ethyl, carboxy-methyl or carboxy-ethyl.

Embodiment 69

A compound according to embodiment 68 wherein $R^{51}$ is methyl, ethyl, hydroxy-methyl, hydroxy-ethyl, carboxy-methyl or carboxy-ethyl.

Embodiment 70

A compound according to any one of the embodiments 1 to 69 wherein $R^{52}$ is halogen, cyano, hydroxy, carboxy, —$CF_3$, methyl, ethyl, hydroxy-methyl, hydroxy-ethyl, carboxy-methyl or carboxy-ethyl.

Embodiment 71

A compound according to any one of the embodiments 1 to 70 wherein $R^{53}$ is halogen, cyano, hydroxy, carboxy, —$CF_3$, methyl, ethyl, hydroxy-methyl, hydroxy-ethyl, carboxy-methyl or carboxy-ethyl.

Embodiment 72

A compound according to any one of the embodiments 1 to 71, which compound is an activator of glucokinase, when tested in the Glucokinase Activation Assay (I) disclosed herein at a glucose concentration of 2 mM.

Embodiment 73

A compound according to any one of the embodiments 1 to 72, which compound is an activator of glucokinase, when tested in the Glucokinase Activation Assay (I) disclosed herein at a glucose concentration of from 10 to 15 mM.

Embodiment 74

A compound according to any one of the embodiments 1 to 73, which compound, at a concentration of 30 µM, is capable of providing an at least 1.5, such as at least 1.7, for instance at least 2.0 fold activation of glucokinase in the Glucokinase Activation Assay (I) disclosed herein at a glucose concentration of 2 mM.

Embodiment 75

A compound according to any one of the embodiments 1 to 74, which compound, at a concentration of 30 µM, is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment 76

A compound according to any one of the embodiments 1 to 75, which at a concentration of 5 µM is capable of providing an at least 1.5, such as at least 1.7, for instance at least 2.0 fold activation of glucokinase in the Glucokinase Activation Assay (I) disclosed herein at a glucose concentration of 2 mM.

Embodiment 77

A compound according to any one of the embodiments 1 to 76, which at a concentration of 5 µM is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment 78

A compound according to any one of the embodiments 1 to 77, which compound provides an increase in glucokinase activity, where the increase in glucokinase activity provided by the compound increases with increasing concentrations of glucose.

Embodiment 79

A compound according to embodiment 77 or embodiment 78, which provides an increase in glucokinase activity in Glucokinase Activation Assay (I) disclosed herein at a glucose concentration of 15 mM, which increase is significantly higher than the increase in glucokinase activity provided by the compound in Glucokinase Activation Assay (I) disclosed herein at a glucose concentration of 5 mM.

Embodiment 80

A compound according to any one of the embodiments 77 to 79, which at a compound concentration of 10 µM provides an increase in glucokinase activity in Glucokinase Activation Assay (I) disclosed herein at a glucose concentration of 15 mM, which increase is significantly higher than the increase in glucokinase activity provided by the compound at a compound concentration of 10 µM in Glucokinase Activation Assay (I) disclosed herein at a glucose concentration of 5 mM.

Embodiment 81

A compound according to any one of the embodiments 77 to 80, which at a compound concentration of 10 µM provides an increase in glucokinase activity in Glucokinase Activation Assay (I) disclosed herein at a glucose concentration of 15 mM, which increase is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the increase in glucokinase activity provided by the compound at a compound concentration of 10 μM in Glucokinase Activation Assay (I) disclosed herein at a glucose concentration of 5 mM.

Embodiment 82

A compound according to any one of the embodiments 1 to 81, which compound increases glucose utilization in the liver without inducing any increase in insulin secretion in response to glucose.

Embodiment 83

A compound according to any one of the embodiments 1 to 81, which compound shows a significantly higher activity in isolated hepatocytes compared to the activity of the compound in Ins-1 cells.

Embodiment 84

A compound according to any one of the embodiments 82 to 83, which compound shows a significantly higher activity in isolated hepatocytes measured as described in the Glucokinase Activity Assay (II) compared to the activity of the compound in Ins-1 cells measured as described in the Glucokinase Activity Assay (III).

Embodiment 85

A compound according to embodiment 84, which compound shows an activity in isolated hepatocytes measured as described in the Glucokinase Activity Assay (II) which activity is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the compound in Ins-1 cells measured as described in the Glucokinase Activity Assay (III).

Embodiment 86

A compound according to embodiment 84, which compound shows no activity in the Ins-1 cells measured as described in the Glucokinase Activity Assay (III).

Embodiment 87

A compound according to any one of embodiments 1 to 86 for use as a medicament.

Embodiment 88

A compound according to any one of embodiments 1 to 86 for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

Embodiment 89

A pharmaceutical composition comprising, as an active ingredient, at least one compound according to any one of embodiments 1 to 88 together with one or more pharmaceutically acceptable carriers or excipients.

Embodiment 90

A pharmaceutical composition according to embodiment 89 in unit dosage form, comprising from about 0.05 mg to about 1000 mg, preferably from about 0.1 mg to about 500 mg and especially preferred from about 0.5 mg to about 200 mg of the compound according to any one of embodiments 1 to 88.

Embodiment 91

Use of a compound represented by the general formula (II)

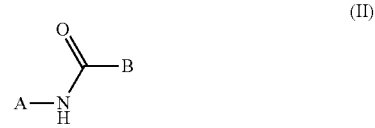

wherein B is heteroaryl optionally substituted with one or more substituents independently selected from $R^1$, $R^2$, $R^3$, $R^4$, $R^5$, $R^6$, and $R^7$;

$R^1$, $R^2$, $R^3$, $R^4$, $R^6$, and $R^7$ are independently selected from the group consisting of
  hydrogen, halogen, nitro, cyano, hydroxy, carboxy, —$CF_3$; or
  —$NR^{10}R^{11}$; or
  $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, heteroaryl-$C_{1-6}$-alkyl, $C_{1-6}$-alkoxy, aryl-$C_{1-6}$-alkoxy, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, $C_{1-6}$-alkylsulfonyl, $C_{1-6}$-alkylsulfinyl, arylsulfonyl, heteroarylsulfonyl, aryl, heteroaryl, $C_{1-6}$-alkyl-carbonyl, carboxy-$C_{1-6}$-alkyl, hydroxy-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or
  —CO—$NR^{13}R^{14}$;
$R^{10}$ and $R^{11}$ independently represent hydrogen, $C_{1-6}$-alkyl, —C(O)—$C_{1-6}$-alkyl, carboxy-$C_{1-6}$-alkyl, —C(O)—$C_{1-6}$-alkyl-C(O)OH, —$S(O)_2CH_3$, or aryl;
$R^{12}$ is halogen, cyano, hydroxy, carboxy, —$CF_3$, $C_{1-6}$-alkyl, —$S(O)_2CH_3$, or —$S(O)_2NH_2$;
$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a heterocycle such as piperazine, homopiperazine or morpholine;

$R^{15}$ is halogen, cyano, hydroxy, carboxy, —$CF_3$, $C_{1-6}$-alkyl, —$S(O)_2CH_3$, or —$S(O)_2NH_2$;

$R^5$ is selected from
- $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, $C_{1-6}$-alkylcarbamoyl-$C_{1-6}$-alkyl, di-($C_{1-6}$-alkyl)carbamoyl-$C_{1-6}$-alkyl, each of which is optionally substituted with one or more substituents independently selected from $R^{32}$; or
- aryl-$C_{1-6}$-alkyl, aryl-O—$C_{1-6}$-alkyl, or aryl-S—$C_{1-6}$-alkyl, wherein the aryl group may be substituted with one or more substituents independently selected from $R^{20}$; or
- heteroaryl-$C_{1-6}$-alkyl, wherein the heteroaryl group may be substituted with one or more substituents independently selected from $R^{26}$; or
- —$C_{1-6}$-alkyl-C(O)—$NR^{28}R^{29}$ or —$C_{1-6}$-alkyl-$NR^{28}R^{29}$; wherein the alkyl part may be substituted with one or more substituents independently selected from $R^{33}$; or
- —$C(O)NR^{30}R^{31}$;

$R^{32}$ and $R^{33}$ are independently halogen, cyano, hydroxy, carboxy, —$CF_3$, $C_{1-6}$-alkyl, —$S(O)_2CH_3$, or —$S(O)_2NH_2$ $R^{20}$ is
- hydrogen, halogen, nitro, cyano, $CF_3$, hydroxy, carboxy; or
- —C(O)—O—$C_{1-6}$-alkyl, $C_{1-6}$-alkoxy, $C_{1-6}$-alkyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl each of which is optionally substituted with one or more substituents independently selected from $R^{21}$; or
- —$NR^{22}R^{23}$ or —$C_{1-6}$-alkyl-$NR^{22}R^{23}$ optionally substituted with one or more substituents independently selected from $R^{34}$; or
- —$CONR^{24}R^{25}$;

$R^{21}$ is halogen, nitro, cyano, $CF_3$, hydroxy, $C_{1-6}$-alkyl, —$S(O)_2CH_3$, —$S(O)_2NH_2$ or carboxy;

$R^{22}$ and $R^{23}$ are independently selected from hydrogen, —C(O)—$C_{1-6}$-alkyl or $C_{1-6}$-alkyl;

$R^{24}$ and $R^{25}$ are independently selected from the group consisting of hydrogen, $C_{1-6}$-alkyl, hydroxy-$C_{1-6}$-alkyl, carboxy-$C_{1-6}$-alkyl, aryl or heteroaryl, or $R^{24}$ and $R^{25}$ together with the nitrogen to which they are attached form a heterocycle such as piperazine, homopiperazine or morpholine;

$R^{26}$ is
- hydrogen, halogen, nitro, cyano, hydroxy, carboxy; or
- —C(O)—O—$C_{1-6}$-alkyl, $C_{1-6}$-alkoxy, $C_{1-6}$-alkyl, sulfonyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl, each of which is optionally substituted with one or more substituents independently selected from $R^{27}$;

$R^{27}$ is halogen, nitro, cyano, hydroxy, or carboxy;

$R^{28}$ and $R^{29}$ are independently selected from hydrogen, —C(O)—O—$C_{1-6}$-alkyl, —C(O)—$C_{1-6}$-alkyl or $C_{1-6}$-alkyl;

$R^{30}$ and $R^{31}$ are independently selected from the group consisting of hydrogen, $C_{1-6}$-alkyl, hydroxy-$C_{1-6}$-alkyl, carboxy-$C_{1-6}$-alkyl, aryl, heteroaryl, or $R^{30}$ and $R^{31}$ together with the nitrogen to which they are attached form a heterocycle such as piperazine, homopiperazine or morpholine;

$R^{34}$ is halogen, nitro, cyano, $CF_3$, hydroxy, $C_{1-6}$-alkyl, —$S(O)_2CH_3$, —$S(O)_2NH_2$ or carboxy;

A is heteroaryl which is optionally substituted with one or more substituents selected independently from $R^{40}$, $R^{41}$ and $R^{42}$ $R^{40}$, $R^{41}$ and $R^{42}$ are independently selected from
- halogen, carboxy, cyano, nitro, hydroxy, —$CF_3$, —SCN; or
- $C_{1-6}$-alkyl, $C_{1-6}$-alkoxy, $C_{1-6}$-alkylthio, $C_{1-6}$-alkylamino, di($C_{1-6}$-alkyl)amino, $C_{1-6}$-alkylsulfonyl, $C_{1-6}$-alkylsulfinyl, —C(O)—$C_{1-6}$-alkyl, —$NH_2$—C(O)—$C_{1-6}$-alkyl, —$C_{1-6}$-alkyl-S—$C_{1-6}$-alkyl, carboxy-$C_{1-6}$-alkyl, $C_{1-6}$-alkylamino-$C_{1-6}$-alkyl or hydroxy-$C_{1-6}$-alkyl, each of which is optionally substituted with one or more substituents independently selected from $R^{43}$; or
- aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, aryloxy, heteroaryloxy, arylthio, heteroarylthio, arylsulfonyl, heteroarylsulfonyl, aryl-$C_{1-6}$-alkylamino, each of which is optionally substituted on the aryl or heteroaryl part with one or more substituents independently selected from $R^{44}$; or
- $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{45}$; or
- —$NR^{46}R^{47}$, —$C_{1-6}$-alkyl-$NR^{46}R^{47}$, —$C_{1-6}$-alkyl-S(O)—$R^{48}$, —$C_{1-6}$-alkyl-$S(O)_2$—$R^{48}$ wherein each alkyl part may be substituted with one or more substituents independently selected from $R^{52}$; or
- —$CONR^{49}R^{50}$, —$C_{1-6}$-alkyl-$CONR^{49}R^{50}$ optionally substituted with one or more substituents independently selected from $R^{53}$; or two of $R^{40}$, $R^{41}$ and $R^{42}$ can be taken together to form a $C_{2-5}$-alkylene bridge;

$R^{43}$, $R^{44}$, and $R^{45}$ are independently $C_{1-6}$-alkyl, halogen, nitro, cyano, hydroxy, carboxy, —$CF_3$, carboxy-$C_{1-6}$-alkyl, —$S(O)_2CH_3$, or —$S(O)_2NH_2$;

$R^{46}$ and $R^{47}$ independently represent hydrogen, $C_{1-6}$-alkyl, hydroxy-$C_{1-6}$-alkyl, carboxy-$C_{1-6}$-alkyl, aryl, heteroaryl or $R^{44}$ and $R^{45}$ together with the nitrogen to which they are attached form a heterocycle such as piperazine, homopiperazine or morpholine;

$R^{48}$ is selected from
- $C_{1-6}$-alkyl, carboxy-$C_{1-6}$-alkyl, $C_{1-6}$-alkylamino-$C_{1-6}$-alkyl or hydroxy-$C_{1-6}$-alkyl; or
- aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{51}$; or
- $C_{3-8}$-cycloalkyl, $C_{3-8}$-cycloalkenyl, $C_{3-8}$-cycloalkyl-$C_{1-6}$-alkyl, $C_{3-3}$-cycloalkenyl-$C_{1-6}$-alkyl.

$R^{49}$ and $R^{50}$ are independently selected from hydrogen and $C_{1-6}$-alkyl.

$R^{51}$ is halogen, nitro, cyano, hydroxy, carboxy, —$CF_3$, $C_{1-6}$-alkyl, hydroxy-$C_{1-6}$-alkyl, or carboxy-$C_{1-6}$-alkyl.

$R^{52}$ and $R^{53}$ are independently $C_{1-6}$-alkyl, halogen, nitro, cyano, hydroxy, carboxy, —$CF_3$, —$S(O)_2CH_3$, or —$S(O)_2NH_2$ as well as any salt hereof with a pharmaceutically acceptable acid or base, or any optical isomer or mixture of optical isomers, including a racemic mixture, or any tautomeric forms, for the preparation of a medicament for increasing the activity of glucokinase.

Embodiment 92

The use according to embodiment 91 for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins.

Embodiment 93

The use according to embodiment 91 for the preparation of a medicament for the adjuvant treatment of type 1 diabetes for preventing the onset of diabetic complications.

Embodiment 94

The use according to embodiment 91 for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

Embodiment 95

Use according to any one of the embodiments 91 to 94 in a regimen which comprises treatment with a further antidiabetic agent.

Embodiment 96

Use according to any one of the embodiments 91 to 95 in a regimen which comprises treatment with a further antihyperlipidemic agent.

Embodiment 97

Use according to any one of embodiments 91 to 96 in a regimen which comprises treatment with a further antiobesity agent.

Embodiment 98

Use according to any one of the embodiments 91 to 97 in a regimen which comprises treatment with a further antihypertensive agent.

Embodiment 99

The use according to any one of the embodiments 91 to 98 of a compound of Formula (II) wherein B is heteroaryl selected from thienyl, furyl, pyrrolyl, pyrazolyl, imidazolyl, oxazolyl, thiazolyl, isoxazolyl, isothiazolyl, pyridyl, pyridazinyl, pyrimidinyl, pyrazinyl, indolyl, indazolyl, pyrrolo[2,3-b]pyridyl, pyrrolo[2,3-c]pyridyl, benzo[b]thienyl, benzo[b]furyl, quinolyl, isoquinolyl, cinnolinyl, phthalazinyl, quinazolinyl, quinoxalinyl, each of which may optionally be substituted with one or more substituents independently selected from $R^1$, $R^2$, $R^3$, $R^4$, $R^5$, $R^6$, and $R^7$.

Embodiment 100

The use according to embodiment 99 of a compound of Formula (II) wherein B is heteroaryl selected from thienyl, pyrrolyl, pyrazolyl, oxazolyl, thiazolyl, pyridyl, pyridazinyl, pyrimidinyl, pyrazinyl, indolyl, indazolyl, pyrrolo[2,3-b]pyridyl, pyrrolo[2,3-c]pyridyl, benzo[b]thienyl, quinolyl, isoquinolyl, each of which may optionally be substituted with one or more substituents independently selected from $R^1$, $R^2$, $R^3$, $R^4$, $R^5$, $R^6$, and $R^7$.

Embodiment 101

The use according to embodiment 100 of a compound of Formula (II) wherein B is heteroaryl selected from thienyl, pyrrolyl, pyrazolyl, oxazolyl, thiazolyl, pyridyl, indolyl, indazolyl, pyrrolo[2,3-b]pyridyl, pyrrolo[2,3-c]pyridyl, benzo[b]thienyl, each of which may optionally be substituted with one or more substituents independently selected from $R^1$, $R^2$, $R^3$, $R^4$, $R^5$, $R^6$, and $R^7$.

Embodiment 102

The use according to embodiment 101 of a compound according to any one of the embodiments 1 to 86.

Embodiment 103

In another embodiment the invention provides compounds represented by the general formula (III),

wherein B is

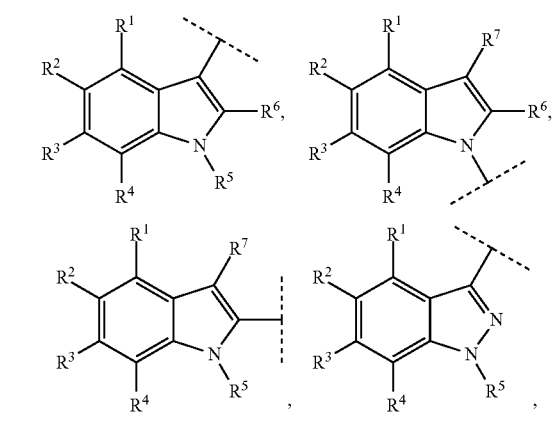

-continued

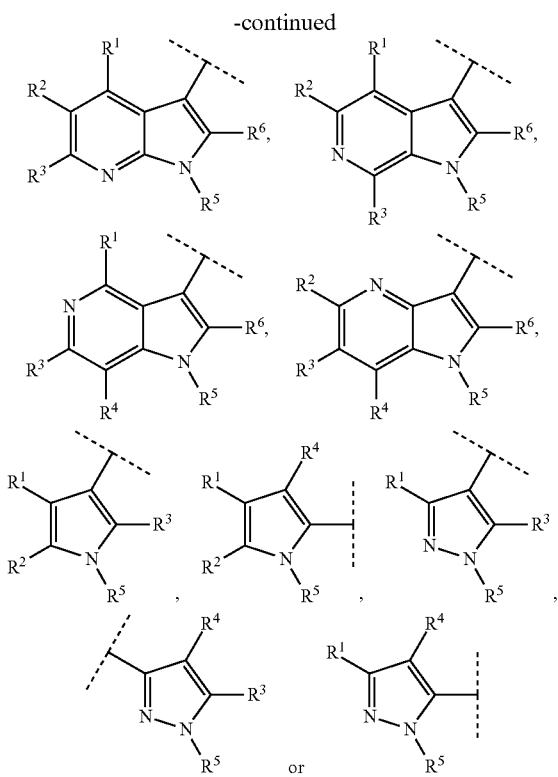

R¹, R², R³, R⁴, R⁶, and R⁷ are independently selected from the group consisting of
  hydrogen, halogen, nitro, cyano, hydroxy, carboxy, —CF₃; or
  —NR¹⁰R¹¹; or
  $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, heteroaryl-$C_{1-6}$-alkyl, $C_{1-6}$-alkoxy, aryl-$C_{1-6}$-alkoxy, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, $C_{1-6}$-alkylsulfonyl, $C_{1-6}$-alkylsulfinyl, arylsulfonyl, heteroarylsulfonyl, aryl, heteroaryl, $C_{1-6}$-alkyl-carbonyl, —C(O)—O—$C_{1-6}$-alkyl, $C_{1-6}$-alkyl-O—$C_{1-6}$-alkyl, carboxy-$C_{1-6}$-alkyl, hydroxy-$C_{1-6}$-alkyl, carboxy-$C_{1-6}$-alkyloxy, $C_{1-6}$-alkylamino-$C_{1-6}$-alkyl, di($C_{1-6}$-alkylamino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from R¹²; or
  —CO—NR¹³R¹⁴, —C(O)—$C_{3-8}$-cycloalkyl;
R¹⁰ and R¹¹ independently represent hydrogen, $C_{1-6}$-alkyl, carboxy-$C_{1-6}$-alkyl, —C(O)—$C_{1-6}$-alkyl-C(O)OH, —S(O)₂CH₃, or aryl;
R¹² is halogen, cyano, hydroxy, carboxy, —CF₃, $C_{1-6}$-alkyl, —S(O)₂CH₃, or —S(O)₂NH₂;
R¹³ and R¹⁴ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from R¹⁵; or R¹³ and R¹⁴ together with the nitrogen to which they are attached form a heterocycle such as piperazine, homopiperazine or morpholine;
R¹⁵ is halogen, cyano, hydroxy, carboxy, —CF₃, $C_{1-6}$-alkyl, —S(O)₂CH₃, or —S(O)₂NH₂;

R⁵ is selected from
  $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, $C_{1-6}$-alkylcarbamoyl-$C_{1-6}$-alkyl, di-($C_{1-6}$-alkyl)carbamoyl-$C_{1-6}$-alkyl, each of which is optionally substituted with one or more substituents independently selected from R³²; or
  aryl-$C_{1-6}$-alkyl, aryl-C(O)—$C_{1-6}$-alkyl, aryl-O—$C_{1-6}$-alkyl, aryl-sulfonyl or aryl-S—$C_{1-6}$-alkyl, wherein the aryl group may be substituted with one or more substituents independently selected from R²⁰; or
  heteroaryl-$C_{1-6}$-alkyl, $C_{3-8}$-heterocyclyl-$C_{1-6}$-alkyl wherein the heteroaryl or heterocyclyl group may be substituted with one or more substituents independently selected from R²⁶; or
  —$C_{1-6}$-alkyl-C(O)—NR²⁸R²⁹ or —$C_{1-6}$-alkyl-NR²⁸R²⁹; wherein the alkyl part may be substituted with one or more substituents independently selected from R³³; or
  —C(O)NR³⁰R³¹ or S(O)₂—R³²;
R³² and R³³ are independently halogen, cyano, hydroxy, carboxy, —CF₃, $C_{1-6}$-alkyl, —S(O)₂CH₃, or —S(O)₂NH₂
R²⁰ is
  hydrogen, halogen, nitro, cyano, CF₃, hydroxy, carboxy; or
  —C(O)—O—$C_{1-6}$-alkyl, $C_{1-6}$-alkoxy, $C_{1-6}$-alkyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl each of which is optionally substituted with one or more substituents independently selected from R²¹; or
  NR²²R²³ or —$C_{1-6}$-alkyl-NR²²R²³ optionally substituted with one or more substituents independently selected from R³⁴; or
  —CONR²⁴R²⁵;
R²¹ is halogen, nitro, cyano, CF₃, hydroxy, $C_{1-6}$-alkyl, —S(O)₂CH₃, —S(O)₂NH₂ or carboxy;
R²² and R²³ are independently selected from hydrogen, —C(O)—$C_{1-6}$-alkyl or $C_{1-6}$-alkyl;
R²⁴ and R²⁵ are independently selected from the group consisting of hydrogen, $C_{1-6}$-alkyl, hydroxy-$C_{1-6}$-alkyl, carboxy-$C_{1-6}$-alkyl, aryl or heteroaryl, or R²⁴ and R²⁵ together with the nitrogen to which they are attached form a heterocycle such as piperazine, homopiperazine or morpholine;
R²⁶ is
  hydrogen, halogen, nitro, cyano, hydroxy, carboxy; or
  —C(O)—O—$C_{1-6}$-alkyl, $C_{1-6}$-alkoxy, $C_{1-6}$-alkyl, sulfonyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl, each of which is optionally substituted with one or more substituents independently selected from R²⁷;
R²⁷ is halogen, nitro, cyano, hydroxy, or carboxy;
R²⁸ and R²⁹ are independently selected from hydrogen, —C(O)—O—$C_{1-6}$-alkyl, —C(O)—$C_{1-6}$-alkyl or $C_{1-6}$-alkyl;
R³⁰ and R³¹ are independently selected from the group consisting of hydrogen, $C_{1-6}$-alkyl, hydroxy-$C_{1-6}$-alkyl, carboxy-$C_{1-6}$-alkyl, aryl, heteroaryl, or R³⁰ and R³¹ together with the nitrogen to which they are attached form a heterocycle such as piperazine, homopiperazine or morpholine;
R³⁴ is halogen, nitro, cyano, CF₃, hydroxy, $C_{1-6}$-alkyl, —S(O)₂CH₃, —S(O)₂NH₂ or carboxy;
A is heteroaryl which is optionally substituted with one or more substituents selected independently from R⁴⁰, R⁴¹ and R⁴²

$R^{40}$, $R^{41}$ and $R^{42}$ are independently selected from halogen, carboxy, cyano, nitro, hydroxy, —$CF_3$, —SCN; or $C_{1-6}$-alkyl, $C_{1-6}$-alkoxy, $C_{1-6}$-alkylthio, $C_{1-6}$-alkylamino, di($C_{1-6}$-alkyl)amino, $C_{1-6}$-alkylsulfonyl, $C_{1-6}$-alkylsulfinyl, —C(O)—O—$C_{1-6}$-alkyl, —C(O)—$C_{1-6}$-alkyl, —NH—C(O)—$C_{1-6}$-alkyl, —$C_{1-6}$-alkyl-O—$C_{1-6}$-alkyl, —$C_{1-6}$—S—$C_{1-6}$-alkyl, carboxy-$C_{1-6}$-alkyl, di($C_{1-6}$-alkyl)amino-$C_{1-6}$-alkyl, $C_{1-6}$-alkylamino-$C_{1-6}$-alkyl or hydroxy-$C_{1-6}$-alkyl, each of which is optionally substituted with one or more substituents independently selected from $R^{43}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, aryloxy, heteroaryloxy, arylthio, heteroarylthio, arylsulfonyl, heteroarylsulfonyl, aryl-$C_{1-6}$-alkylamino, each of which is optionally substituted on the aryl or heteroaryl part with one or more substituents independently selected from $R^{44}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{45}$; or —$NR^{46}R^{47}$, —$C_{1-6}$-alkyl-$NR^{46}R^{47}$, —$C_{1-6}$-alkyl-S—$R^{48}$—$C_{1-6}$-alkyl-S(O)—$R^{48}$, —$C_{1-6}$-alkyl-S(O)$_2$—$R^{48}$ wherein each alkyl part may be substituted with one or more substituents independently selected from $R^{52}$; or —$CONR^{49}R^{50}$, —$C_{1-6}$-alkyl-$CONR^{49}R^{50}$ optionally substituted with one or more substituents independently selected from $R^{53}$; or two of $R^{40}$, $R^{41}$ and $R^{42}$ can be taken together to form a $C_{2-5}$-alkylene bridge;

$R^{43}$, $R^{44}$, and $R^{45}$ are independently $C_{1-6}$-alkyl, halogen, nitro, cyano, hydroxy, carboxy, —$CF_3$, carboxy-$C_{1-6}$-alkyl, —C(O)—O—$C_{1-6}$-alkyl, —$S(O)_2CH_3$, or —$S(O)_2NH_2$;

$R^{46}$ and $R^{47}$ independently represent hydrogen, $C_{1-6}$-alkyl, hydroxy-$C_{1-6}$-alkyl, carboxy-$C_{1-6}$-alkyl, aryl, heteroaryl or $R^{44}$ and $R^{45}$ together with the nitrogen to which they are attached form a heterocycle such as piperazine, homopiperazine or morpholine;

$R^{48}$ is selected from $C_{1-6}$-alkyl, carboxy-$C_{1-6}$-alkyl, $C_{1-6}$-alkylamino-$C_{1-6}$-alkyl or hydroxy-$C_{1-6}$-alkyl; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{51}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl.

$R^{49}$ and $R^{50}$ are independently selected from hydrogen and $C_{1-6}$-alkyl.

$R^{51}$ is halogen, nitro, cyano, hydroxy, carboxy, —$CF_3$, $C_{1-6}$-alkyl, hydroxy-$C_{1-6}$-alkyl, or carboxy-$C_{1-6}$-alkyl.

$R^{52}$ and $R^{53}$ are independently $C_{1-6}$-alkyl, halogen, nitro, cyano, hydroxy, carboxy, —$CF_3$, —$S(O)_2CH_3$, or —$S(O)_2NH_2$ as well as any salt hereof with a pharmaceutically acceptable acid or base, or any optical isomer or mixture of optical isomers, including a racemic mixture, or any tautomeric forms, with the exception of compounds represented by the general formula (IV)

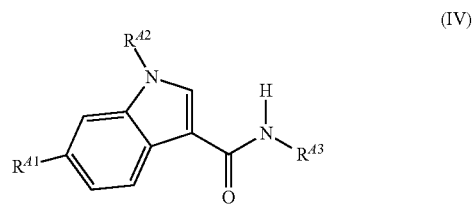

(IV)

wherein $R^{41}$ is halo, nitro, amino, cyano, methyl, trifluoromethyl, hydroxy, methoxy, trifluoromethoxy, methylthio, methylsulfinyl, or methylsulfonyl; $R^{42}$ is lower alkyl having from 2 to 5 carbon atoms or —$CH_2$—$R^{44}$ wherein $R^{44}$ is cycloalkyl having from 3 to 6 carbon atoms; and $R^{43}$ is an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of methyl, trifluoromethyl, chloro, bromo, nitro, cyano, —$(CH_2)_m$—$OR^{45}$, —$(CH_2)_m$—C(O)—$OR^{45}$, —$(CH_2)_m$—C(O)—$NHR^{45}$, and —$(CH_2)_m$—$NHR^{45}$, wherein m is 0 or 1; $R^{45}$ is hydrogen or lower alkyl; or a pharmaceutically acceptable salt thereof, and further with the exception of the compounds

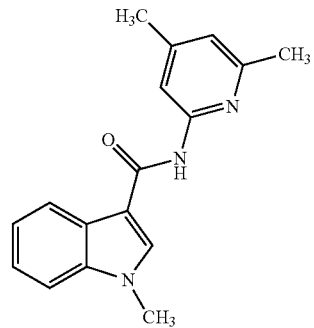

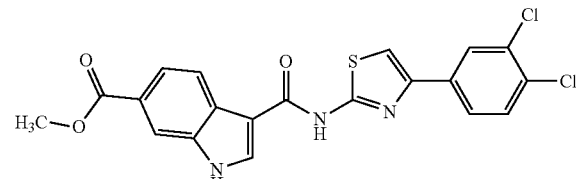

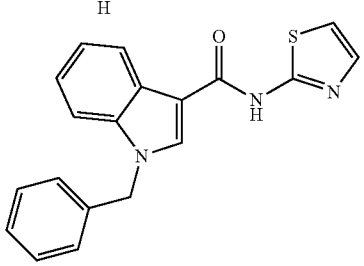

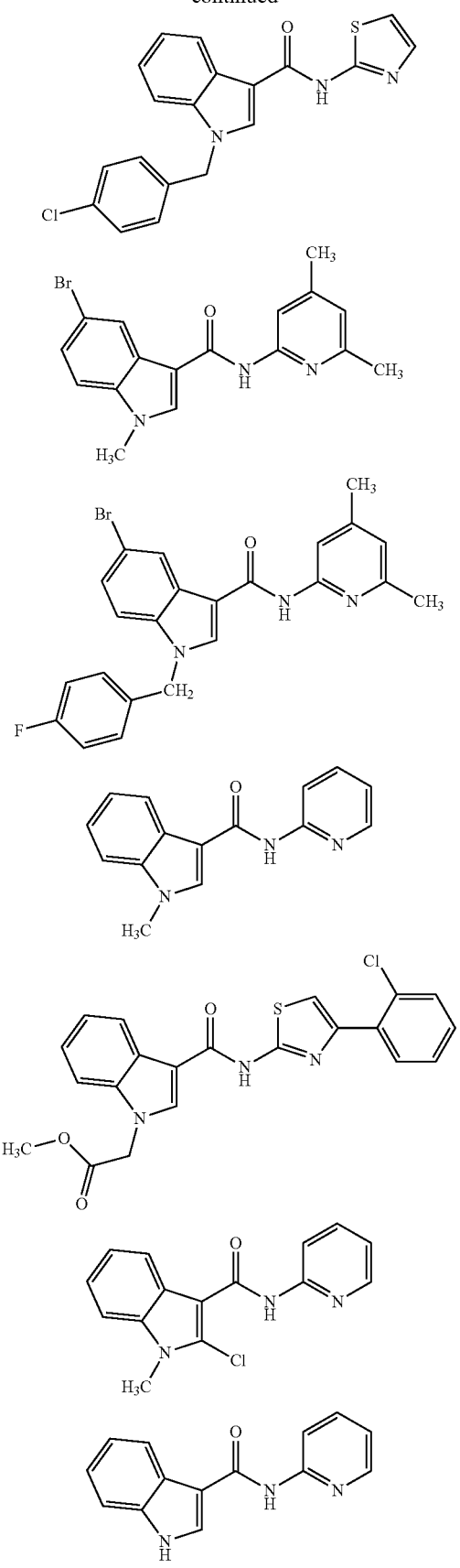

and with the proviso that if A is thiazolyl and B is indolyl, then A cannot be substituted in the 4-position with
- $C_{5-8}$-cycloalkyl optionally substituted with $C_{1-4}$-alkyl,
- aryl optionally substituted with one or more substituents selected from halogen, $C_{1-6}$-alkyl, $C_{1-3}$ alkoxy or $C_{1-3}$ thioalkoxy, nitro, $CF_3$,
- heteroaryl substituted with one or more substituents selected from $C_{1-3}$-alkyl or halogen and with the proviso that if A is thiadiazolyl and B is unsubstituted indolyl or indolyl substituted on the nitrogen atom with
- —C(O)—$C_{1-4}$-alkyl,
- —$(CH_2)_n$C(O)R wherein n is 1 or 2 and R is $OR^{1'}$ or $NR^{1'}R^{2'}$, $R^{1'}R^{2'}$ being selected from H or $C_{1-4}$-alkyl,
- Hydroxy-$C_{1-4}$-alkyl,
- $C_{2-6}$ alkoxyalkyl,
- tetrahydropyranyl, then A cannot be substituted in the 3-position with
- phenyl, pyridine, or pyrimidine, each of which may optionally be substituted with up to four substituents selected from Cl, Br, $C_{1-3}$-alkyl, or $C_{1-3}$-alkoxy and $CF_3$,
- naphtyl optionally substituted with halogen, $C_{1-3}$-alkyl, or $C_{1-3}$-alkoxy.

Embodiment 104

In another embodiment the invention provides compounds represented by the general formula (V),

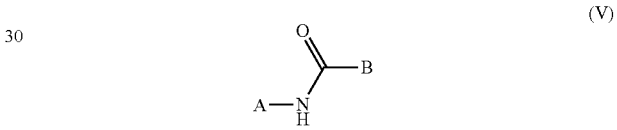

wherein B is

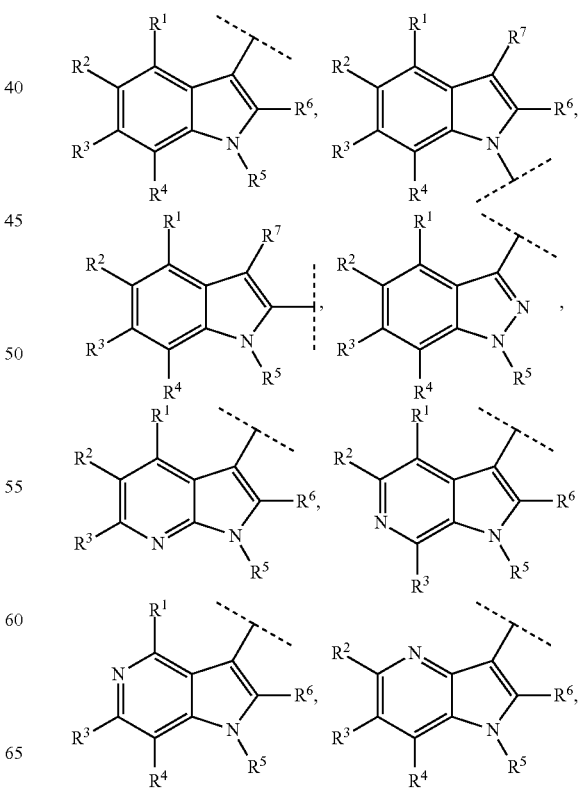

-continued

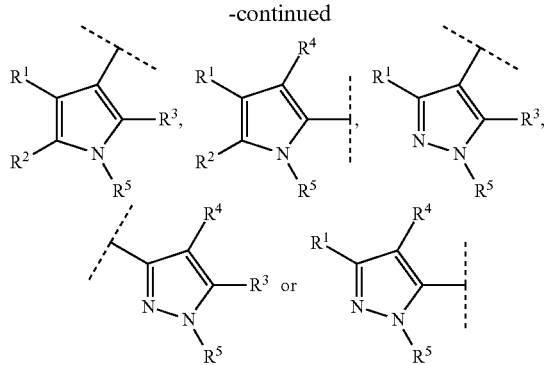

$R^1, R^2, R^3, R^4, R^6,$ and $R^7$ are independently selected from the group consisting of
  hydrogen, halogen, nitro, cyano, hydroxy, carboxy, —$CF_3$; or
  —$NR^{10}R^{11}$; or
  $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, heteroaryl-$C_{1-6}$-alkyl, $C_{1-6}$-alkoxy, aryl-$C_{1-6}$-alkoxy, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, $C_{1-6}$-alkylsulfonyl, arylsulfonyl, heteroarylsulfonyl, aryl, heteroaryl, $C_{1-6}$-alkyl-carbonyl, —C(O)—O—$C_{1-6}$-alkyl, carboxy-$C_{1-6}$-alkyl, hydroxy-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or
  —CO—$NR^{13}R^{14}$, $C_{1-6}$-alkyl-O—$C_{1-6}$-alkyl, —C(O)—$C_{3-8}$-cycloalkyl;
$R^{10}$ and $R^{11}$ independently represent hydrogen, $C_{1-6}$-alkyl, —C(O)—$C_{1-6}$-alkyl, carboxy-$C_{1-6}$-alkyl, —C(O)—$C_{1-6}$-alkyl-C(O)OH, —$S(O)_2CH_3$, or aryl;
$R^{12}$ is halogen, cyano, hydroxy, carboxy, —$CF_3$, $C_{1-6}$-alkyl, —$S(O)_2CH_3$, or —$S(O)_2NH_2$;
$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a heterocycle such as piperazine, homopiperazine or morpholine;
$R^{15}$ is halogen, cyano, hydroxy, carboxy, —$CF_3$, $C_{1-6}$-alkyl, —$S(O)_2CH_3$, or —$S(O)_2NH_2$;
$R^5$ is selected from
  $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, $C_{1-6}$-alkylcarbamoyl-$C_{1-6}$-alkyl, di-($C_{1-6}$-alkyl)carbamoyl-$C_{1-6}$-alkyl, each of which is optionally substituted with one or more substituents independently selected from $R^{32}$; or
  aryl-$C_{1-6}$-alkyl, aryl-C(O)—$C_{1-6}$-alkyl, aryl-O—$C_{1-6}$-alkyl, aryl-sulfonyl or aryl-S—$C_{1-6}$-alkyl, wherein the aryl group may be substituted with one or more substituents independently selected from $R^{20}$; or
  heteroaryl-$C_{1-6}$-alkyl or $C_{3-8}$-heterocyclyl-$C_{1-6}$-alkyl wherein the heteroaryl or heterocyclyl group may be substituted with one or more substituents independently selected from $R^{26}$; or
  —$C_{1-6}$-alkyl-C(O)—$NR^{28}R^{29}$ or —$C_{1-6}$-alkyl-$NR^{28}R^{29}$; wherein the alkyl part may be substituted with one or more substituents independently selected from $R^{33}$; or
  —C(O)$NR^{30}R^{31}$ or $S(O)_2$—$R^{32}$;
$R^{32}$ and $R^{33}$ are independently halogen, cyano, hydroxy, carboxy, —$CF_3$, $C_{1-6}$-alkyl, —$S(O)_2CH_3$, or —$S(O)_2NH_2$
$R^{20}$ is
  hydrogen, halogen, nitro, cyano, $CF_3$, hydroxy, carboxy; or
  —C(O)—O—$C_{1-6}$-alkyl, $C_{1-6}$-alkoxy, $C_{1-6}$-alkyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl each of which is optionally substituted with one or more substituents independently selected from $R^{21}$; or
  —$NR^{22}R^{23}$ or —$C_{1-6}$-alkyl-$NR^{22}R^{23}$ optionally substituted with one or more substituents independently selected from $R^{34}$; or
  —$CONR^{24}R^{25}$;
$R^{21}$ is halogen, nitro, cyano, $CF_3$, hydroxy, $C_{1-6}$-alkyl, —$S(O)_2CH_3$, —$S(O)_2NH_2$ or carboxy;
$R^{22}$ and $R^{23}$ are independently selected from hydrogen, —C(O)—$C_{1-6}$-alkyl or $C_{1-6}$-alkyl;
$R^{24}$ and $R^{25}$ are independently selected from the group consisting of hydrogen, $C_{1-6}$-alkyl, hydroxy-$C_{1-6}$-alkyl, carboxy-$C_{1-6}$-alkyl, aryl or heteroaryl, or $R^{24}$ and $R^{25}$ together with the nitrogen to which they are attached form a heterocycle such as piperazine, homopiperazine or morpholine;
$R^{26}$ is
  hydrogen, halogen, nitro, cyano, hydroxy, carboxy; or
  —C(O)—O—$C_{1-6}$-alkyl, $C_{1-6}$-alkoxy, $C_{1-6}$-alkyl, sulfonyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl, each of which is optionally substituted with one or more substituents independently selected from $R^{27}$;
$R^{27}$ is halogen, nitro, cyano, hydroxy, or carboxy;
$R^{28}$ and $R^{29}$ are independently selected from hydrogen, —C(O)—O—$C_{1-6}$-alkyl, —C(O)—$C_{1-6}$-alkyl or $C_{1-6}$-alkyl;
$R^{30}$ and $R^{31}$ are independently selected from the group consisting of hydrogen, $C_{1-6}$-alkyl, hydroxy-$C_{1-6}$-alkyl, carboxy-$C_{1-6}$-alkyl, aryl, heteroaryl, or $R^{30}$ and $R^{31}$ together with the nitrogen to which they are attached form a heterocycle such as piperazine, homopiperazine or morpholine;
$R^{34}$ is halogen, nitro, cyano, $CF_3$, hydroxy, $C_{1-6}$-alkyl, —$S(O)_2CH_3$, —$S(O)_2NH_2$ or carboxy;
A is heteroaryl which is optionally substituted with one or more substituents selected independently from $R^{40}, R^{41}$ and $R^{42}$
$R^{40}, R^{41}$ and $R^{42}$ are independently selected from
  halogen, carboxy, cyano, nitro, hydroxy, —$CF_3$, —SCN; or
  $C_{1-6}$-alkyl, $C_{1-6}$-alkoxy, $C_{1-6}$-alkylthio, $C_{1-6}$-alkylamino, di($C_{1-6}$-alkyl)amino, $C_{1-6}$-alkylsulfonyl, $C_{1-6}$-alkylsulfinyl, —C(O)—O—$C_{1-6}$-alkyl, —C(O)—$C_{1-6}$-alkyl, —NH—C(O)—$C_{1-6}$-alkyl, —$C_{1-6}$-alkyl-O—$C_{1-6}$-alkyl, —$C_{1-6}$-alkyl-S—$C_{1-6}$-alkyl, carboxy-$C_{1-6}$-alkyl, di($C_{1-6}$-alkyl)amino-$C_{1-6}$-alkyl, $C_{1-6}$-alkylamino-$C_{1-6}$-alkyl or hydroxy-$C_{1-6}$-alkyl, each of which is optionally substituted with one or more substituents independently selected from $R^{43}$; or
  aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio- $C_{1-6}$-alkyl, aryloxy, heteroaryloxy, arylthio, heteroarylthio, arylsulfonyl, heteroarylsulfonyl, aryl-$C_{1-6}$-alkylamino, each of which is optionally substituted on the aryl or heteroaryl part with one or more substituents independently selected from $R^{44}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{45}$; or —$NR^{46}R^{47}$, —$C_{1-6}$-alkyl-$NR^{46}R^{47}$, —$C_{1-6}$-alkyl-S(O)—$R^{48}$, —$C_{1-6}$-alkyl-S(O)$_2$—$R^{48}$ wherein each alkyl part may be substituted with one or more substituents independently selected from $R^{52}$; or —$CONR^{49}R^{50}$, —$C_{1-6}$-alkyl-$CONR^{49}R^{50}$ optionally substituted with one or more substituents independently selected from $R^{53}$; or two of $R^{40}$, $R^{41}$ and $R^{42}$ can be taken together to form a $C_{2-5}$-alkylene bridge;

$R^{43}$, $R^{44}$, and $R^{45}$ are independently $C_{1-6}$-alkyl, halogen, nitro, cyano, hydroxy, carboxy, —$CF_3$, carboxy-$C_{1-6}$-alkyl, —C(O)—O—$C_{1-6}$-alkyl, —$S(O)_2CH_3$, or —$S(O)_2NH_2$, $R^{46}$ and $R^{47}$ independently represent hydrogen, $C_{1-6}$-alkyl, hydroxy-$C_{1-6}$-alkyl, carboxy-$C_{1-6}$-alkyl, aryl, heteroaryl or $R^{44}$ and $R^{45}$ together with the nitrogen to which they are attached form a heterocycle such as piperazine, homopiperazine or morpholine;

$R^{48}$ is selected from $C_{1-6}$-alkyl, carboxy-$C_{1-6}$-alkyl, $C_{1-6}$-alkylamino-$C_{1-6}$-alkyl or hydroxy-$C_{1-6}$-alkyl; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{51}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl.

$R^{49}$ and $R^{50}$ are independently selected from hydrogen and $C_{1-6}$-alkyl.

$R^{51}$ is halogen, nitro, cyano, hydroxy, carboxy, —$CF_3$, $C_{1-6}$-alkyl, hydroxy-$C_{1-6}$-alkyl, or carboxy-$C_{1-6}$-alkyl.

$R^{52}$ and $R^{53}$ are independently $C_{1-6}$-alkyl, halogen, nitro, cyano, hydroxy, carboxy, —$CF_3$, —$S(O)_2CH_3$, or —$S(O)_2NH_2$ as well as any salt hereof with a pharmaceutically acceptable acid or base, or any optical isomer or mixture of optical isomers, including a racemic mixture, or any tautomeric forms, with the exception of the compounds

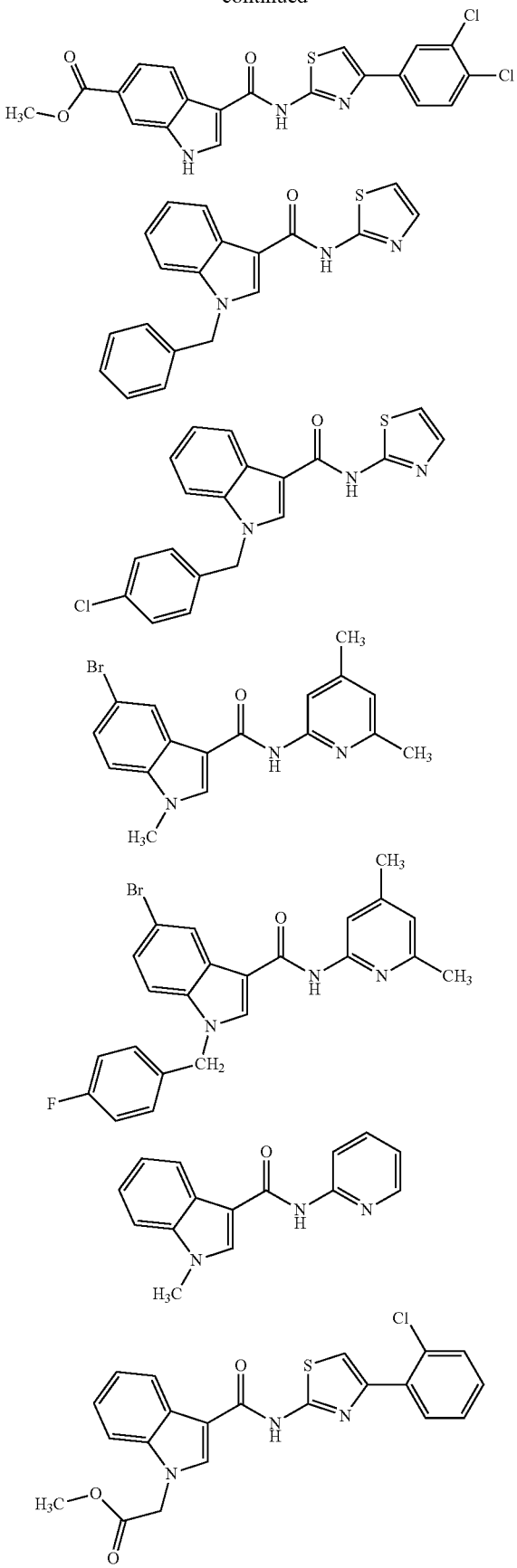

51
-continued
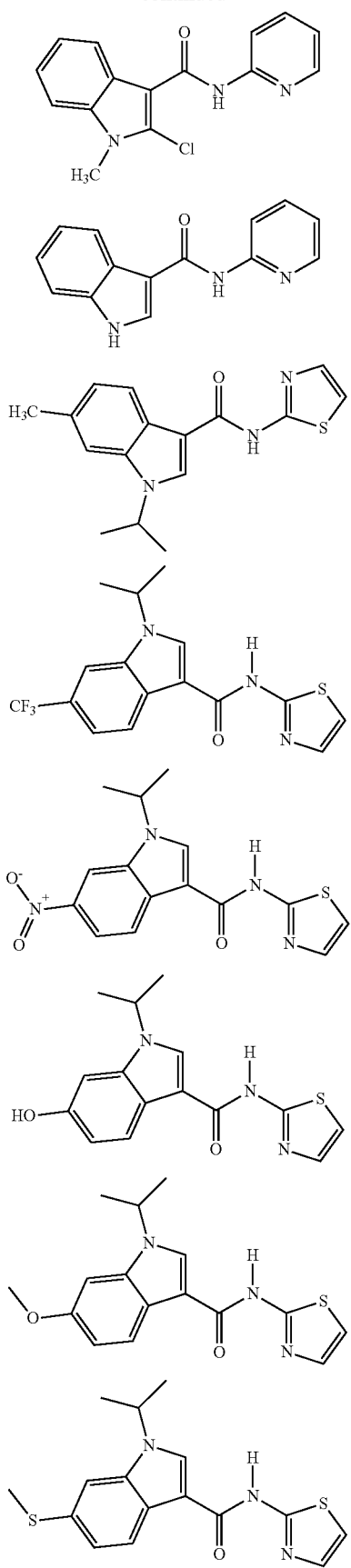
52
-continued
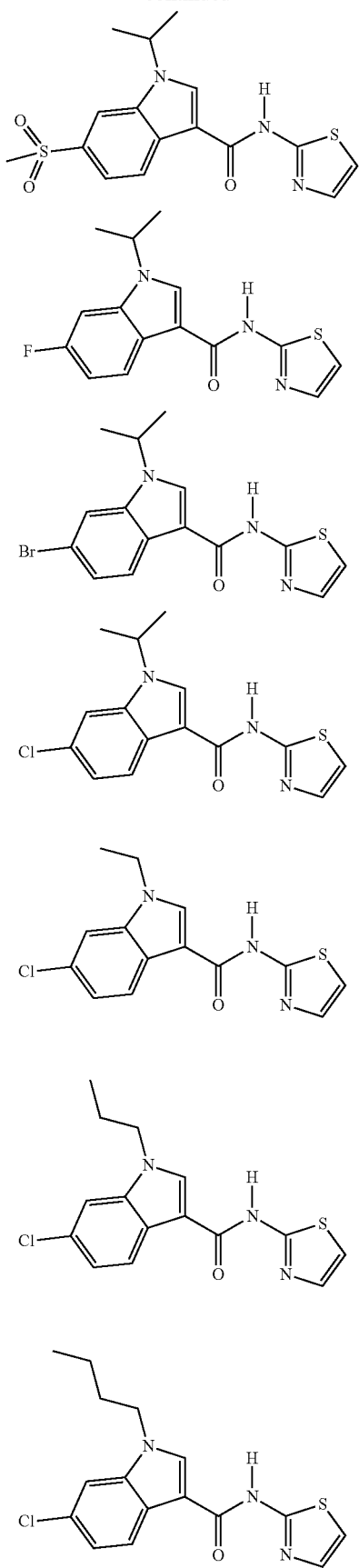

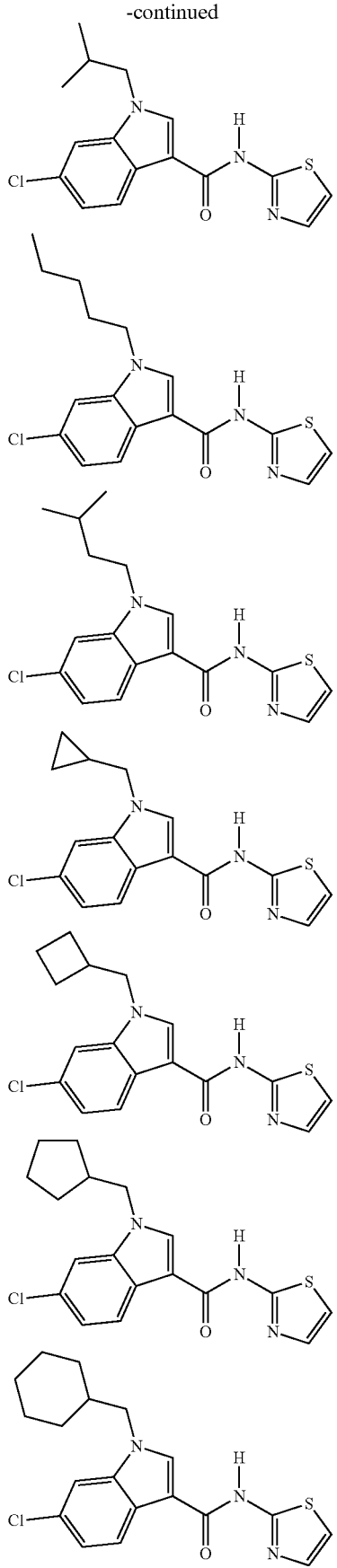
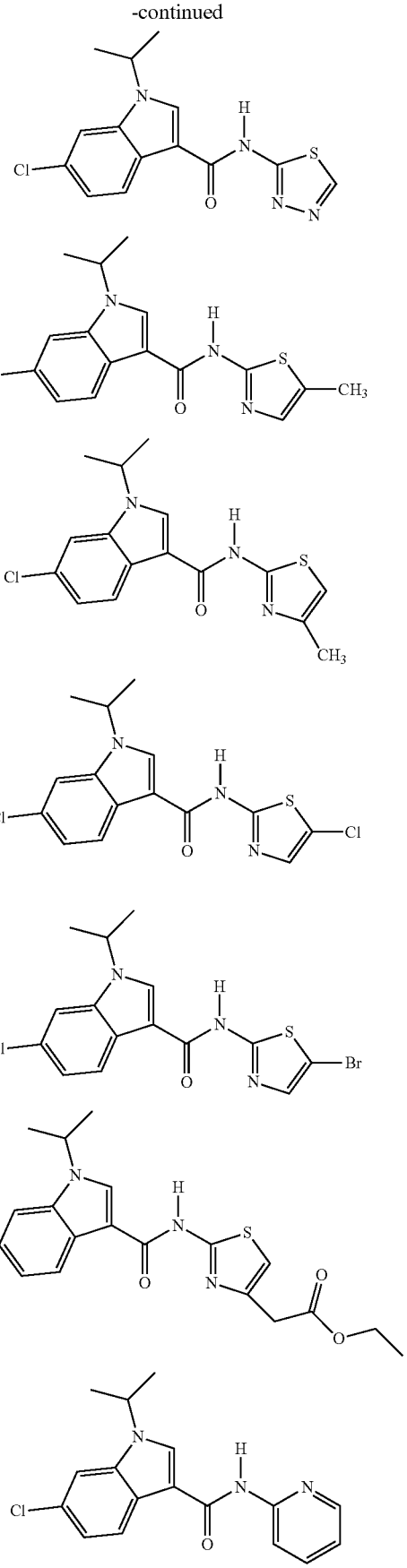

-continued

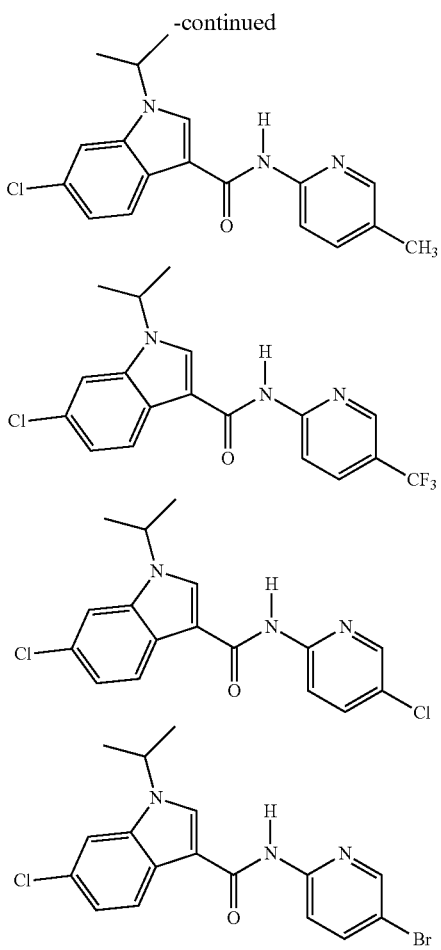

and with the proviso that if A is thiazolyl and B is indolyl, then A cannot be substituted in the 4-position with
- $C_{5-8}$-cycloalkyl optionally substituted with $C_{1-4}$-alkyl,
- aryl optionally substituted with one or more substituents selected from halogen, $C_{1-6}$-alkyl, $C_{1-3}$ alkoxy or $C_{1-3}$ thioalkoxy, nitro, $CF_3$,
- heteroaryl substituted with one or more substituents selected from $C_{1-3}$-alkyl or halogen and with the proviso that if A is thiadiazolyl and B is unsubstituted indolyl or indolyl substituted on the nitrogen atom with
- —C(O)—$C_{1-4}$-alkyl,
- —$(CH_2)_n$C(O)R wherein n is 1 or 2 and R is $OR^{1\prime}$ or $NR^{1\prime}R^{2\prime}$, $R^{1\prime}R^{2\prime}$ being selected from H or $C_{1-4}$-alkyl,
- Hydroxy-$C_{1-4}$-alkyl,
- $C_{2-6}$ alkoxyalkyl,
- tetrahydropyranyl, then A cannot be substituted in the 3-position with
- phenyl, pyridine, or pyrimidine, each of which may optionally be substituted with up to four substituents selected from Cl, Br, $C_{1-3}$-alkyl, or $C_{1-3}$-alkoxy and $CF_3$,
- naphtyl optionally substituted with halogen, $C_{1-3}$-alkyl, or $C_{1-3}$-alkoxy.

Embodiment 105

An embodiment according to embodiment 103 or 104 wherein B is Error! Objects cannot be created from editing field codes.

Embodiment 106

A compound according to embodiment 103 or 104 wherein B is

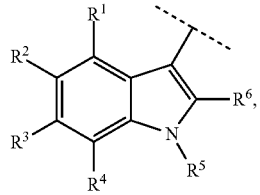

$R^1$, $R^2$, $R^3$, $R^4$, and $R^6$ are independently selected from the group consisting of
- hydrogen, halogen, nitro, cyano, hydroxy, carboxy, —$CF_3$; or
- —$NR^{10}R^{11}$; or
- $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, heteroaryl-$C_{1-6}$-alkyl, $C_{1-6}$-alkoxy, aryl-$C_{1-6}$-alkoxy, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, $C_{1-6}$-alkylsulfonyl, $C_{1-6}$-alkylsulfinyl, arylsulfonyl, heteroarylsulfonyl, aryl, heteroaryl, $C_{1-6}$-alkyl-carbonyl, —C(O)—O—$C_{1-6}$-alkyl, carboxy-$C_{1-6}$-alkyl, hydroxy-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or
- —CO—$NR^{13}R^{14}$, $C_{1-6}$-alkyl-O—$C_{1-6}$-alkyl, —C(O)—$C_{3-8}$-cycloalkyl;

$R^{10}$ and $R^{11}$ independently represent hydrogen, $C_{1-6}$-alkyl, —C(O)—$C_{1-6}$-alkyl, carboxy-$C_{1-6}$-alkyl, —C(O)—$C_{1-6}$-alkyl-C(O)OH, —$S(O)_2CH_3$, or aryl;

$R^{12}$ is halogen, cyano, hydroxy, carboxy, —$CF_3$, $C_{1-6}$-alkyl, —$S(O)_2CH_3$, or —$S(O)_2NH_2$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a heterocycle such as piperazine, homopiperazine or morpholine;

$R^{15}$ is halogen, cyano, hydroxy, carboxy, —$CF_3$, $C_{1-6}$-alkyl, —$S(O)_2CH_3$, or —$S(O)_2NH_2$;

$R^5$ is selected from
- $C_{2-6}$-alkenyl, $C_{2-6}$-alkynyl, $C_{3-8}$-cycloalkyl, $C_{3-8}$-cycloalkenyl, $C_{3-8}$-cycloalkyl-$C_{2-6}$-alkyl, $C_{3-8}$-cycloalkenyl-$C_{1-6}$-alkyl, $C_{1-6}$-alkylcarbamoyl-$C_{1-6}$-alkyl, di-($C_{1-6}$-alkyl)carbamoyl-$C_{1-6}$-alkyl, each of which is optionally substituted with one or more substituents independently selected from $R^{32}$; or
- aryl-$C_{1-6}$-alkyl, aryl-C(O)—$C_{1-6}$-alkyl, aryl-O—$C_{1-6}$-alkyl, aryl-sulfonyl or aryl-S—$C_{1-6}$-alkyl, wherein the aryl group may be substituted with one or more substituents independently selected from $R^{20}$; or
- heteroaryl-$C_{1-6}$-alkyl or $C_{3-8}$-heterocyclyl-$C_{1-6}$-alkyl wherein the heteroaryl or heterocyclyl group may be substituted with one or more substituents independently selected from $R^{26}$; or —C$_{1-6}$-alkyl-C(O)—NR$^{28}$R$^{29}$ or —C$_{1-6}$-alkyl-NR$^{28}$R$^{29}$; wherein the alkyl part may be substituted with one or more substituents independently selected from R$^{33}$; or —C(O)NR$^{30}$R$^{31}$ or S(O)$_2$—R$^{32}$; or C$_{1-6}$-alkyl substituted with one or more substituents independently selected from R$^{32}$;

R$^{32}$ and R$^{33}$ are independently halogen, cyano, hydroxy, carboxy, —CF$_3$, C$_{1-6}$-alkyl, —S(O)$_2$CH$_3$, —C(O)NR$^{30}$R$^{31}$ or —S(O)$_2$NH$_2$ R$^{20}$ is hydrogen, halogen, nitro, cyano, CF$_3$, hydroxy, carboxy; or —C(O)—O—C$_{1-6}$-alkyl, C$_{1-6}$-alkoxy, C$_{1-6}$-alkylthio, C$_{1-6}$-alkylsulfonyl, C$_{1-6}$-alkylsulfinyl, C$_{1-6}$-alkylsulfamoyl, di(C$_{1-6}$-alkyl)sulfamoyl, C$_{1-6}$-alkylsulfinamoyl, di(C$_{1-6}$-alkyl)sulfinamoyl, carboxy-C$_{1-6}$-alkyl, C$_{1-6}$-alkylamino C$_{1-6}$-alkyl, di-(C$_{1-6}$-alkyl)amino-C$_{1-6}$-alkyl or hydroxy-C$_{1-6}$-alkyl each of which is optionally substituted with one or more substituents independently selected from R$^{21}$; or —NR$^{22}$R$^{23}$ or —C$_{1-6}$-alkyl-NR$^{22}$R$^{23}$ optionally substituted with one or more substituents independently selected from R$^{34}$; or

—CONR$^{24}$R$^{25}$;

R$^{21}$ is halogen, nitro, cyano, CF$_3$, hydroxy, C$_{1-6}$-alkyl, —S(O)$_2$CH$_3$, —S(O)$_2$NH$_2$ or carboxy;

R$^{22}$ and R$^{23}$ are independently selected from hydrogen, —C(O)—C$_{1-6}$-alkyl or C$_{1-6}$-alkyl;

R$^{24}$ and R$^{25}$ are independently selected from the group consisting of hydrogen, C$_{1-6}$-alkyl, hydroxy-C$_{1-6}$-alkyl, carboxy-C$_{1-6}$-alkyl, aryl or heteroaryl, or R$^{24}$ and R$^{25}$ together with the nitrogen to which they are attached form a heterocycle such as piperazine, homopiperazine or morpholine;

R$^{26}$ is hydrogen, halogen, nitro, cyano, hydroxy, carboxy; or

—CO—NR$^{13}$R$^{14}$; or

—C(O)—O—C$_{1-6}$-alkyl, C$_{1-6}$-alkoxy, sulfonyl, C$_{1-6}$-alkylthio, C$_{1-6}$-alkylsulfonyl, C$_{1-6}$-alkylsulfinyl, C$_{1-6}$-alkylsulfamoyl, di(C$_{1-6}$-alkyl)sulfamoyl, C$_{1-6}$-alkylsulfinamoyl, di(C$_{1-6}$-alkyl)sulfinamoyl, carboxy-C$_{1-6}$-alkyl, C$_{1-6}$-alkylamino di-(alkyl)amino-C$_{1-6}$-alkyl or hydroxy-C$_{1-6}$-alkyl, each of which is optionally substituted with one or more substituents independently selected from R$^{27}$;

R$^{27}$ is halogen, nitro, cyano, hydroxy, or carboxy;

R$^{28}$ and R$^{29}$ are independently selected from hydrogen, —C(O)—O—C$_{1-6}$-alkyl, —C(O)—C$_{1-6}$-alkyl or R$^{30}$ and R$^{31}$ are independently selected from the group consisting of hydrogen, C$_{1-6}$-alkyl, hydroxy-C$_{1-6}$-alkyl, carboxy-C$_{1-6}$-alkyl, aryl, heteroaryl, or R$^{30}$ and R$^{31}$ together with the nitrogen to which they are attached form a heterocycle such as piperazine, homopiperazine or morpholine;

R$^{34}$ is halogen, nitro, cyano, CF$_3$, hydroxy, C$_{1-6}$-alkyl, —S(O)$_2$CH$_3$, —S(O)$_2$NH$_2$ or carboxy;

as well as any salt hereof with a pharmaceutically acceptable acid or base, or any optical isomer or mixture of optical isomers, including a racemic mixture, or any tautomeric forms, with the exception of the compounds

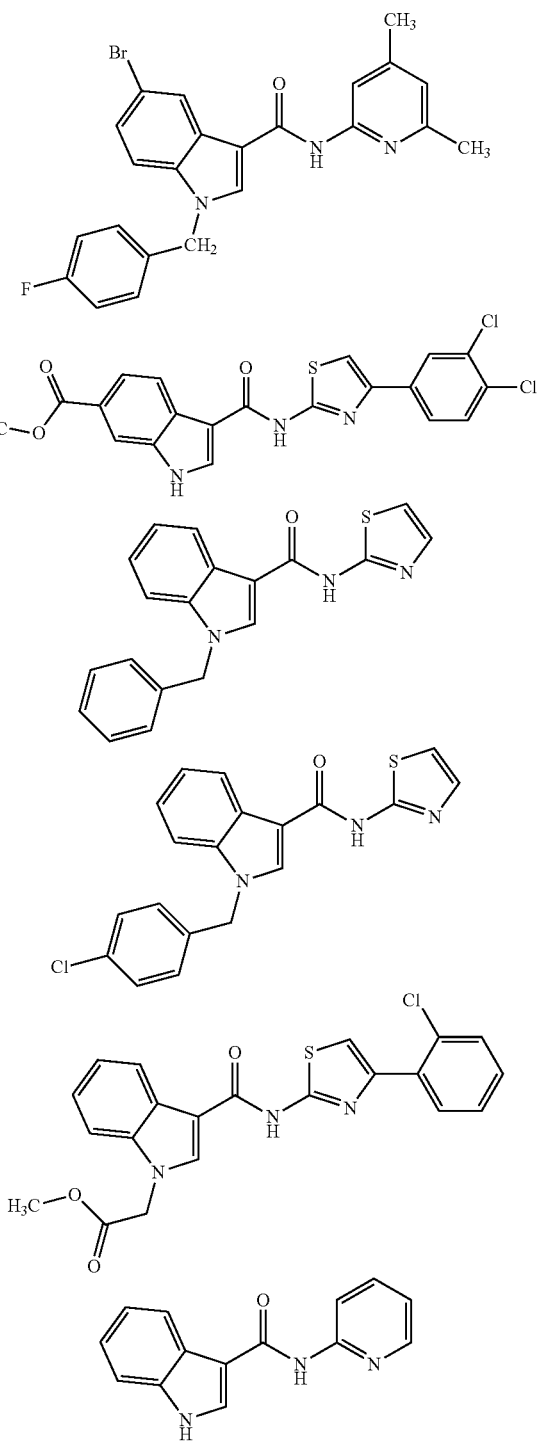

and with the proviso that if A is thiazolyl, then A cannot be substituted in the 4-position with C$_{5-8}$-cycloalkyl optionally substituted with C$_{1-4}$-alkyl, aryl optionally substituted with one or more substituents selected from halogen, C$_{1-6}$-alkyl, C$_{1-3}$ alkoxy or C$_{1-3}$ thioalkoxy, nitro, CF$_3$, heteroaryl substituted with one or more substituents selected from C$_{1-3}$-alkyl or halogen and with the proviso that if A is thiadiazolyl and B indolyl substituted on the nitrogen atom with
—C(O)—C$_{1-4}$-alkyl,
—(CH$_2$)$_n$C(O)R wherein n is 1 or 2 and R is OR$^{1'}$ or NR$^{1'}$R$^{2'}$, R$^{1'}$R$^{2'}$ being selected from H or C$_{1-4}$-alkyl,
Hydroxy-C$_{1-4}$-alkyl,
C$_{2-6}$ alkoxyalkyl,
tetrahydropyranyl,
then A cannot be substituted in the 3-position with
phenyl, pyridine, or pyrimidine, each of which may optionally be substituted with up to four substituents selected from Cl, Br, C$_{1-3}$-alkyl, or C$_{1-3}$-alkoxy and CF$_3$,
naphtyl optionally substituted with halogen, C$_{1-3}$-alkyl, or C$_{1-3}$-alkoxy.

Embodiment 107

A compound according to embodiment 103 or 104 wherein B is

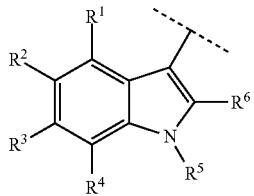

R$^1$, R$^2$, R$^3$, R$^4$, and R$^6$ are independently selected from the group consisting of
hydrogen, halogen, nitro, cyano, hydroxy, carboxy, —CF$_3$; or
—NR$^{10}$R$^{11}$; or
C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, aryl-C$_{1-6}$-alkyl, heteroaryl-C$_{1-6}$-alkyl, C$_{1-6}$-alkoxy, aryl-C$_{1-6}$-alkoxy, heteroaryl-C$_{1-6}$-alkoxy, aryloxy, heteroaryloxy, C$_{1-6}$-alkylthio, arylthio, heteroarylthio, aryl-C$_{1-6}$-alkylthio, heteroaryl-C$_{1-6}$-alkylthio, C$_{1-6}$-alkylsulfonyl, C$_{1-6}$-alkylsulfinyl, arylsulfonyl, heteroarylsulfonyl, aryl, heteroaryl, C$_{1-6}$-alkyl-carbonyl, —C(O)—O—C$_{1-6}$-alkyl, carboxy-C$_{1-6}$-alkyl, hydroxy-C$_{1-6}$-alkyl, carboxy-C$_{1-6}$-alkyloxy, amino-C$_{1-6}$-alkyl, di-(C$_{1-6}$-alkyl)amino-C$_{1-6}$-alkyl, C$_{1-6}$-alkylsulfamoyl, di(C$_{1-6}$-alkyl)sulfamoyl, C$_{1-6}$-alkylsulfinamoyl or di(C$_{1-6}$-alkyl)sulfinamoyl each of which is optionally substituted with one or more substituents independently selected from R$^{12}$; or
—CO—NR$^{13}$R$^{14}$, —C(O)—C$_{3-8}$-cycloalkyl;
with the proviso, that if R$^1$, R$^2$, R$^4$, and R$^6$ are all hydrogen, then
R$^3$ is selected from the group consisting of
carboxy, or
—NR$^{10}$R$^{11}$; or
—NH—C(O)—C$_{1-6}$-alkyl,
—NH—S(O)$_2$—C$_{1-6}$-alkyl,
C$_{2-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, alkyl, heteroaryl-C$_{1-6}$-alkyl, C$_{2-6}$-alkoxy, aryl-C$_{1-6}$-alkoxy, heteroaryl-C$_{1-6}$-alkoxy, aryloxy, heteroaryloxy, C$_{2-6}$-alkylthio, arylthio, heteroarylthio, aryl-C$_{1-6}$-alkylthio, heteroaryl-C$_{1-6}$-alkylthio, C$_{2-6}$-alkylsulfonyl, C$_{2-6}$-alkylsulfinyl, arylsulfonyl, heteroarylsulfonyl, aryl, heteroaryl, C$_{1-6}$-alkyl-carbonyl, carboxy-C$_{1-6}$-alkyl, hydroxy-C$_{1-6}$-alkyl, carboxy-C$_{1-6}$-alkyloxy, di-(C$_{1-6}$-alkyl)amino-C$_{1-6}$-alkyl, C$_{1-6}$-alkylsulfamoyl, di(C$_{1-6}$-alkyl)sulfamoyl, C$_{1-6}$-alkylsulfinamoyl or di(C$_{1-6}$-alkyl)sulfinamoyl each of which is optionally substituted with one or more substituents independently selected from R$^{12}$; or
—CO—NR$^{13}$R$^{14}$;

R$^{10}$ and R$^{11}$ independently represent hydrogen, C$_{1-6}$-alkyl, carboxy-C$_{1-6}$-alkyl, —C(O)—C$_{1-6}$-alkyl-C(O)OH, —S(O)$_2$CH$_3$, or aryl;

R$^{12}$ is halogen, cyano, hydroxy, carboxy, —CF$_3$, C$_{1-6}$-alkyl, —S(O)$_2$CH$_3$, or —S(O)$_2$NH$_2$;

R$^{13}$ and R$^{14}$ are independently selected from the group consisting of hydrogen, C$_{1-6}$-alkyl, hydroxy-C$_{1-6}$-alkyl, carboxy-C$_{1-6}$-alkyl, aryl, or heteroaryl, each of which is optionally substituted with one or more substituents independently selected from R$^{15}$; or R$^{13}$ and R$^{14}$ together with the nitrogen to which they are attached form a heterocycle such as piperazine, homopiperazine or morpholine;

R$^{15}$ is halogen, cyano, hydroxy, carboxy, —CF$_3$, C$_{1-6}$-alkyl, —S(O)$_2$CH$_3$, or —S(O)$_2$NH$_2$;

R$^5$ is selected from
C$_{1-6}$-alkyl, C$_{2-6}$-alkenyl, C$_{2-6}$-alkynyl, C$_{3-8}$-cycloalkyl, C$_{3-8}$-cycloalkenyl, C$_{3-8}$-cycloalkyl-C$_{1-6}$-alkyl, C$_{3-8}$-cycloalkenyl-C$_{1-6}$-alkyl, C$_{1-6}$-alkylcarbamoyl-C$_{1-6}$-alkyl, di-(C$_{1-6}$-alkyl)carbamoyl-C$_{1-6}$-alkyl, each of which is optionally substituted with one or more substituents independently selected from R$^{32}$; or
aryl-C$_{1-6}$-alkyl, aryl-C(O)—C$_{1-6}$-alkyl, aryl-O—C$_{1-6}$-alkyl, aryl-sulfonyl or aryl-S—C$_{1-6}$-alkyl, wherein the aryl group may be substituted with one or more substituents independently selected from R$^{20}$; or
heteroaryl-C$_{1-6}$-alkyl or C$_{3-8}$-heterocyclyl-C$_{1-6}$-alkyl wherein the heteroaryl or heterocyclyl group may be substituted with one or more substituents independently selected from R$^{26}$; or
—C$_{1-6}$-alkyl-C(O)—NR$^{28}$R$^{29}$ or —C$_{1-6}$-alkyl-NR$^{28}$R$^{29}$; wherein the alkyl part may be substituted with one or more substituents independently selected from R$^{33}$; or
—C(O)NR$^{30}$R$^{31}$ or S(O)$_2$—R$^{32}$;

R$^{32}$ and R$^{33}$ are independently halogen, cyano, hydroxy, carboxy, —CF$_3$, C$_{1-6}$-alkyl, —S(O)$_2$CH$_3$, or —S(O)$_2$NH$_2$ R$^{20}$ is
hydrogen, halogen, nitro, cyano, CF$_3$, hydroxy, carboxy; or
—C(O)—O—C$_{1-6}$-alkyl, C$_{1-6}$-alkoxy, C$_{1-6}$-alkyl, C$_{1-6}$-alkylthio, C$_{1-6}$-alkylsulfonyl, C$_{1-6}$-alkylsulfinyl, C$_{1-6}$-alkylsulfamoyl, di(C$_{1-6}$-alkyl)sulfamoyl, C$_{1-6}$-alkylsulfinamoyl, di(C$_{1-6}$-alkyl)sulfinamoyl, carboxy-C$_{1-6}$-alkyl, amino-C$_{1-6}$-alkyl, C$_{1-6}$-alkylamino di-(C$_{1-6}$-alkyl)amino-C$_{1-6}$-alkyl or hydroxy-C$_{1-6}$-alkyl each of which is optionally substituted with one or more substituents independently selected from R$^{21}$; or
—NR$^{22}$R$^{23}$ or —C$_{1-6}$-alkyl-NR$^{22}$R$^{23}$ optionally substituted with one or more substituents independently selected from R$^{34}$; or
—CONR$^{24}$R$^{25}$;

R$^{21}$ is halogen, nitro, cyano, CF$_3$, hydroxy, C$_{1-6}$-alkyl, —S(O)$_2$CH$_3$, —S(O)$_2$NH$_2$ or carboxy;

R$^{22}$ and R$^{23}$ are independently selected from hydrogen, —C(O)—C$_{1-6}$-alkyl or C$_{1-6}$-alkyl;

R$^{24}$ and R$^{25}$ are independently selected from the group consisting of hydrogen, C$_{1-6}$-alkyl, hydroxy-C$_{1-6}$-alkyl, carboxy-C$_{1-6}$-alkyl, aryl or heteroaryl, or R$^{24}$ and R$^{25}$ together with the nitrogen to which they are attached form a heterocycle such as piperazine, homopiperazine or morpholine;

R$^{26}$ is
hydrogen, halogen, nitro, cyano, hydroxy, carboxy; or
—C(O)—O—C$_{1-6}$-alkyl, C$_{1-6}$-alkoxy, C$_{1-6}$-alkyl, sulfonyl, C$_{1-6}$-alkylthio, C$_{1-6}$-alkylsulfonyl, C$_{1-6}$-alkylsulfinyl, C$_{1-6}$-alkylsulfamoyl, di(C$_{1-6}$-alkyl)sulfamoyl, C$_{1-6}$- alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl, each of which is optionally substituted with one or more substituents independently selected from $R^{27}$;

$R^{27}$ is halogen, nitro, cyano, hydroxy, or carboxy;

$R^{28}$ and $R^{29}$ are independently selected from hydrogen, —C(O)—O—$C_{1-6}$-alkyl, —C(O)—$C_{1-6}$-alkyl or $C_{1-6}$-alkyl;

$R^{30}$ and $R^{31}$ are independently selected from the group consisting of hydrogen, $C_{1-6}$-alkyl, hydroxy-$C_{1-6}$-alkyl, carboxy-$C_{1-6}$-alkyl, aryl, heteroaryl, or $R^{30}$ and $R^{31}$ together with the nitrogen to which they are attached form a heterocycle such as piperazine, homopiperazine or morpholine;

$R^{34}$ is halogen, nitro, cyano, $CF_3$, hydroxy, $C_{1-6}$-alkyl, —S(O)$_2$CH$_3$, —S(O)$_2$NH$_2$ or carboxy;

as well as any salt hereof with a pharmaceutically acceptable acid or base, or any optical isomer or mixture of optical isomers, including a racemic mixture, or any tautomeric forms, with the exception of the compounds

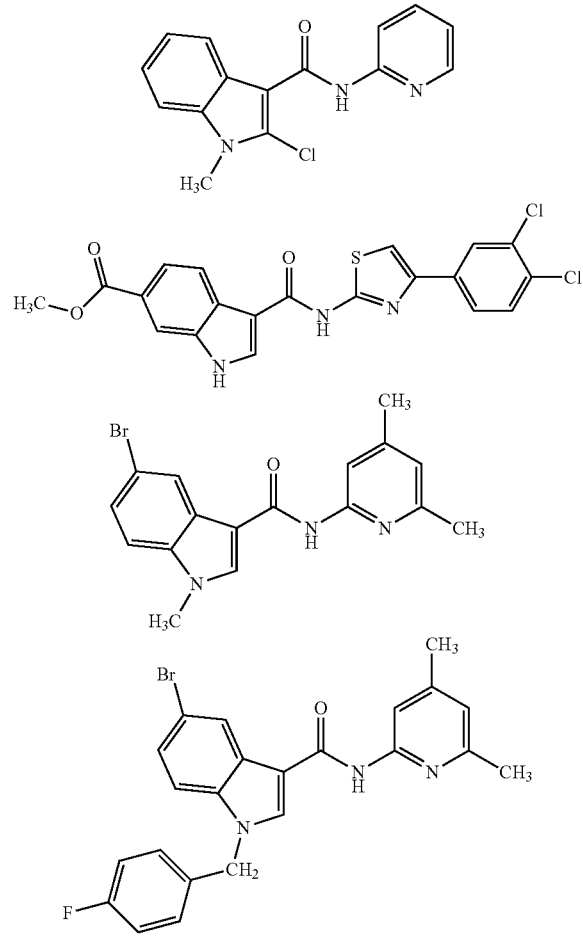

and with the proviso that if A is thiazolyl, then A cannot be substituted in the 4-position with $C_{5-8}$-cycloalkyl optionally substituted with $C_{1-4}$-alkyl, aryl optionally substituted with one or more substituents selected from halogen, $C_{1-6}$-alkyl, $C_{1-3}$ alkoxy or $C_{1-3}$ thioalkoxy, nitro, $CF_3$, heteroaryl substituted with one or more substituents selected from $C_{1-3}$-alkyl or halogen and with the proviso that if A is thiadiazolyl and B is indolyl substituted on the nitrogen atom with —C(O)—$C_{1-4}$-alkyl, —(CH$_2$)$_n$C(O)R wherein n is 1 or 2 and R is OR$^{1'}$ or NR$^{1'}$R$^{2'}$, R$^{1'}$R$^{2'}$ being selected from H or $C_{1-4}$-alkyl, Hydroxy-$C_{1-4}$-alkyl, $C_{2-6}$ alkoxyalkyl, tetrahydropyranyl, then A cannot be substituted in the 3-position with phenyl, pyridine, or pyrimidine, each of which may optionally be substituted with up to four substituents selected from Cl, Br, $C_{1-3}$-alkyl, or $C_{1-3}$-alkoxy and $CF_3$, naphtyl optionally substituted with halogen, $C_{1-3}$-alkyl, or $C_{1-3}$-alkoxy.

Embodiment 108

A compound according to embodiment 103 or 104 wherein B is

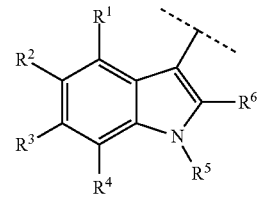

$R^1$, $R^2$, $R^3$, $R^4$, and $R^6$ are independently selected from the group consisting of hydrogen, halogen, nitro, cyano, hydroxy, carboxy, —$CF_3$; or —NR$^{10}$R$^{11}$; or $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, heteroaryl-$C_{1-6}$-alkyl, $C_{1-6}$-alkoxy, aryl-$C_{1-6}$-alkoxy, heteroaryl-$C_{1-6}$-alkoxy, aryloxy, heteroaryloxy, $C_{1-6}$-alkylthio, arylthio, heteroarylthio, aryl-$C_{1-6}$-alkylthio, heteroaryl-$C_{1-6}$-alkylthio, $C_{1-6}$-alkylsulfonyl, $C_{1-6}$-alkylsulfinyl, arylsulfonyl, heteroarylsulfonyl, aryl, heteroaryl, $C_{1-6}$-alkyl-carbonyl, —C(O)—O—$C_{1-6}$-alkyl, carboxy-$C_{1-6}$-alkyl, hydroxy-$C_{1-6}$-alkyl, carboxy-$C_{1-6}$-alkyloxy, $C_{1-6}$-alkylamino-$C_{1-6}$-alkyl, di-($C_{1-6}$-alkyl)amino-$C_{1-6}$-alkyl, $C_{1-6}$-alkylsulfamoyl, di($C_{1-6}$-alkyl)sulfamoyl, $C_{1-6}$-alkylsulfinamoyl or di($C_{1-6}$-alkyl)sulfinamoyl each of which is optionally substituted with one or more substituents independently selected from $R^{12}$; or

—CO—NR$^{13}$R$^{14}$;

$R^{10}$ and $R^{11}$ independently represent hydrogen, $C_{1-6}$-alkyl, —C(O)—$C_{1-6}$-alkyl, carboxy-$C_{1-6}$-alkyl, —C(O)—$C_{1-6}$-alkyl-C(O)OH, —S(O)$_2$CH$_3$, or aryl;

$R^{12}$ is halogen, cyano, hydroxy, carboxy, —$CF_3$, $C_{1-6}$-alkyl, —S(O)$_2$CH$_3$, or —S(O)$_2$NH$_2$;

$R^{13}$ and $R^{14}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{15}$; or $R^{13}$ and $R^{14}$ together with the nitrogen to which they are attached form a heterocycle such as piperazine, homopiperazine or morpholine;

$R^{15}$ is halogen, cyano, hydroxy, carboxy, —$CF_3$, $C_{1-6}$-alkyl, —S(O)$_2$CH$_3$, or —S(O)$_2$NH$_2$;

$R^5$ is selected from $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, $C_{1-6}$-alkylcarbamoyl-$C_{1-6}$-alkyl, di-($C_{1-6}$-alkyl)carbamoyl-$C_{1-6}$-alkyl, each of which is optionally substituted with one or more substituents independently selected from $R^{32}$; or aryl-$C_{1-6}$-alkyl, aryl-C(O)—$C_{1-6}$-alkyl, aryl-O—$C_{1-6}$-alkyl, aryl-sulfonyl or aryl-S—$C_{1-6}$-alkyl, wherein the aryl group may be substituted with one or more substituents independently selected from $R^{20}$; or heteroaryl-$C_{1-6}$-alkyl or $C_{3-8}$-heterocyclyl-$C_{1-6}$-alkyl wherein the heteroaryl or heterocyclyl group may be substituted with one or more substituents independently selected from $R^{26}$; or —$C_{1-6}$-alkyl-C(O)—$NR^{28}R^{29}$ or —$C_{1-6}$-alkyl-$NR^{28}R^{29}$; wherein the alkyl part may be substituted with one or more substituents independently selected from $R^{33}$; or —C(O)$NR^{30}R^{31}$ or S(O)$_2$—$R^{32}$;

$R^{32}$ and $R^{33}$ are independently halogen, cyano, hydroxy, carboxy, —$CF_3$, $C_{1-6}$-alkyl, —S(O)$_2$CH$_3$, or —S(O)$_2$NH$_2$ $R^{20}$ is hydrogen, halogen, nitro, cyano, $CF_3$, hydroxy, carboxy; or —C(O)—O—$C_{1-6}$-alkyl, $C_{1-6}$-alkoxy, $C_{1-6}$-alkyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl each of which is optionally substituted with one or more substituents independently selected from $R^{21}$; or —$NR^{22}R^{23}$ or —$C_{1-6}$-alkyl-$NR^{22}R^{23}$ optionally substituted with one or more substituents independently selected from $R^{34}$; or

—CONR$^{24}R^{25}$;

$R^{21}$ is halogen, nitro, cyano, $CF_3$, hydroxy, $C_{1-6}$-alkyl, —S(O)$_2$CH$_3$, —S(O)$_2$NH$_2$ or carboxy;

$R^{22}$ and $R^{23}$ are independently selected from hydrogen, —C(O)—$C_{1-6}$-alkyl or $C_{1-6}$-alkyl;

$R^{24}$ and $R^{25}$ are independently selected from the group consisting of hydrogen, $C_{1-6}$-alkyl, hydroxy-$C_{1-6}$-alkyl, carboxy-$C_{1-6}$-alkyl, aryl or heteroaryl, or $R^{24}$ and $R^{25}$ together with the nitrogen to which they are attached form a heterocycle such as piperazine, homopiperazine or morpholine;

$R^{26}$ is hydrogen, halogen, nitro, cyano, hydroxy, carboxy; or

—C(O)—O—$C_{1-6}$-alkyl, $C_{1-6}$-alkoxy, $C_{1-6}$-alkyl, sulfonyl, $C_{1-6}$-alkylthio, $C_{1-6}$-alkylsulfonyl, $C_{1-6}$-alkylsulfinyl, $C_{1-6}$-alkylsulfamoyl, di($C_{1-6}$-alkyl)sulfamoyl, $C_{1-6}$-alkylsulfinamoyl, di($C_{1-6}$-alkyl)sulfinamoyl, carboxy-$C_{1-6}$-alkyl, amino-$C_{1-6}$-alkyl, $C_{1-6}$-alkylamino $C_{1-6}$-alkyl, di-($C_{1-6}$-alkyl)amino-$C_{1-6}$-alkyl or hydroxy-$C_{1-6}$-alkyl, each of which is optionally substituted with one or more substituents independently selected from $R^{27}$;

$R^{27}$ is halogen, nitro, cyano, hydroxy, or carboxy;

$R^{28}$ and $R^{29}$ are independently selected from hydrogen, —C(O)—O—$C_{1-6}$-alkyl, —C(O)—$C_{1-6}$-alkyl or $C_{1-6}$-alkyl;

$R^{30}$ and $R^{31}$ are independently selected from the group consisting of hydrogen, $C_{1-6}$-alkyl, hydroxy-$C_{1-6}$-alkyl, carboxy-$C_{1-6}$-alkyl, aryl, heteroaryl, or $R^{30}$ and $R^{31}$ together with the nitrogen to which they are attached form a heterocycle such as piperazine, homopiperazine or morpholine;

$R^{34}$ is halogen, nitro, cyano, $CF_3$, hydroxy, $C_{1-6}$-alkyl, —S(O)$_2$CH$_3$, —S(O)$_2$NH$_2$ or carboxy;

A is heteroaryl which is substituted with one or more substituents selected independently from $R^{40}$, $R^{41}$ and $R^{42}$ $R^{40}$, $R^{41}$ and $R^{42}$ are independently selected from halogen, carboxy, cyano, nitro, hydroxy, —$CF_3$, —SCN; or $C_{1-6}$-alkyl, $C_{1-6}$-alkoxy, $C_{1-6}$-alkylthio, $C_{1-6}$-alkylamino, di($C_{1-6}$-alkyl)amino, $C_{1-6}$-alkylsulfonyl, $C_{1-6}$-alkylsulfinyl, —C(O)—O—$C_{1-6}$-alkyl, —C(O)—$C_{1-6}$-alkyl, —NH—C(O)—$C_{1-6}$-alkyl, —$C_{1-6}$-alkyl-O—$C_{1-6}$-alkyl, —$C_{1-6}$-alkyl-S—$C_{1-6}$-alkyl, carboxy-$C_{1-6}$-alkyl, di($C_{1-6}$-alkyl)amino-$C_{1-6}$-alkyl, $C_{1-6}$-alkylamino-$C_{1-6}$-alkyl or hydroxy-$C_{1-6}$-alkyl, each of which is optionally substituted with one or more substituents independently selected from $R^{43}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, aryloxy, heteroaryloxy, arylthio, heteroarylthio, arylsulfonyl, heteroarylsulfonyl, aryl-$C_{1-6}$-alkylamino, each of which is optionally substituted on the aryl or heteroaryl part with one or more substituents independently selected from $R^{44}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{45}$; or —$NR^{46}R^{47}$, —$C_{1-6}$-alkyl-$NR^{48}R^{47}$, —$C_{1-6}$-alkyl-S—$R^{48}$—$C_{1-6}$-alkyl-S(O)—$R^{48}$, —$C_{1-6}$-alkyl-S(O)$_2$—$R^{48}$ wherein each alkyl part may be substituted with one or more substituents independently selected from $R^{52}$; or —CONR$^{49}R^{50}$, —$C_{1-6}$-alkyl-CONR$^{49}R^{50}$ optionally substituted with one or more substituents independently selected from $R^{53}$; or two of $R^{40}$, $R^{41}$ and $R^{42}$ can be taken together to form a $C_{2-5}$-alkylene bridge;

$R^{43}$, $R^{44}$, and $R^{45}$ are independently $C_{1-6}$-alkyl, halogen, nitro, cyano, hydroxy, carboxy, —$CF_3$, carboxy-$C_{1-6}$-alkyl, —C(O)—O—$C_{1-6}$-alkyl, —S(O)$_2$CH$_3$, or —S(O)$_2$NH$_2$;

$R^{46}$ and $R^{47}$ independently represent hydrogen, $C_{1-6}$-alkyl, hydroxy-$C_{1-6}$-alkyl, carboxy-$C_{1-6}$-alkyl, aryl, heteroaryl or $R^{44}$ and $R^{45}$ together with the nitrogen to which they are attached form a heterocycle such as piperazine, homopiperazine or morpholine;

$R^{48}$ is selected from $C_{1-6}$-alkyl, carboxy-$C_{1-6}$-alkyl, $C_{1-6}$-alkylamino-$C_{1-6}$-alkyl or hydroxy-$C_{1-6}$-alkyl; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{51}$; or $C_{3-8}$-cycloalkyl, $C_{3-3-8}$-cycloalkenyl, $C_{3-8}$-cycloalkyl-$C_{1-6}$-alkyl, $C_{3-8}$-cycloalkenyl-$C_{1-6}$-alkyl.

$R^{49}$ and $R^{50}$ are independently selected from hydrogen and $C_{1-6}$-alkyl.

$R^{51}$ is halogen, nitro, cyano, hydroxy, carboxy, —$CF_3$, $C_{1-6}$-alkyl, hydroxy-$C_{1-6}$-alkyl, or carboxy-$C_{1-6}$-alkyl.

$R^{52}$ and $R^{53}$ are independently $C_{1-6}$-alkyl, halogen, nitro, cyano, hydroxy, carboxy, —$CF_3$, —S(O)$_2$CH$_3$, or —S(O)$_2$NH$_2$;

with the proviso that when A is a monosubstituted heteroaryl $R^{40}$ is selected from carboxy, hydroxy, —SCN; or $C_{2-6}$-alkyl, $C_{1-6}$-alkoxy, $C_{1-6}$-alkylthio, $C_{1-6}$-alkylsulfonyl, $C_{1-6}$-alkylsulfinyl, —C(O)—O—$C_{1-6}$-alkyl, —C(O)—$C_{1-6}$-alkyl, —NH$_2$—C(O)—$C_{1-6}$-alkyl, —$C_{1-6}$-alkyl-O—$C_{1-6}$-alkyl, —$C_{1-6}$-alkyl-S—$C_{1-6}$-alkyl, carboxy-$C_{1-6}$-alkyl, carboxy-$C_{1-6}$-alkylthio, di($C_{1-6}$-alkyl)amino-$C_{2-6}$-alkyl, $C_{1-6}$-alkylamino-$C_{2-6}$- alkyl or hydroxy-$C_{2-6}$-alkyl, each of which is optionally substituted with one or more substituents independently selected from $R^{43}$; or aryl, heteroaryl, aryl-$C_{1-6}$-alkyl, heteroaryl-$C_{1-6}$-alkyl, aryl-$C_{1-6}$-alkoxy, heteroaryl-$C_{1-6}$-alkoxy, aryl-$C_{1-6}$-alkylthio, heteroaryl-$C_{1-6}$-alkylthio, heteroaryl-thio-$C_{1-6}$-alkyl, aryloxy, heteroaryloxy, arylthio, heteroarylthio, arylsulfonyl, heteroarylsulfonyl, aryl-$C_{1-6}$-alkylamino, each of which is optionally substituted on the aryl or heteroaryl part with one or more substituents independently selected from $R^{44}$; or $C_{3-8}$-cycloalkyl, $C_{3-8}$-cycloalkenyl, $C_{3-8}$-cycloalkyl-$C_{1-6}$-alkyl, $C_{3-8}$-cycloalkenyl-$C_{1-6}$-alkyl, each of which is optionally substituted on the cycloalkyl part with one or more substituents independently selected from $R^{45}$; or —$NR^{46}R^{47}$, —$C_{1-6}$-alkyl-$NR^{46}R^{47}$, —$C_{1-6}$-alkyl-S—$R^{48}$—$C_{1-6}$-alkyl-S(O)—$R^{48}$, —$C_{1-6}$-alkyl-S(O)$_2$—$R^{48}$ wherein each alkyl part may be substituted with one or more substituents independently selected from $R^{52}$; or —$CONR^{49}R^{50}$, —$C_{1-6}$-alkyl-$CONR^{49}R^{50}$ optionally substituted with one or more substituents independently selected from $R^{53}$;

$R^{43}$, $R^{44}$, and $R^{45}$ are independently $C_{1-6}$-alkyl, halogen, nitro, cyano, hydroxy, carboxy, —$CF_3$, carboxy-$C_{1-6}$-alkyl, —$S(O)_2CH_3$, or —$S(O)_2NH_2$;

$R^{46}$ and $R^{47}$ independently represent hydroxy-$C_{1-6}$-alkyl, carboxy-$C_{1-6}$-alkyl, aryl, heteroaryl or $R^{44}$ and $R^{45}$ together with the nitrogen to which they are attached form a heterocycle such as piperazine, homopiperazine or morpholine;

$R^{48}$ is selected from $C_{1-6}$-alkyl, carboxy-$C_{1-6}$-alkyl, $C_{1-6}$-alkylamino-$C_{1-6}$-alkyl or hydroxy-$C_{1-6}$-alkyl; or aryl, heteroaryl, aryl-$C_{1-6}$-alkyl, or heteroaryl-$C_{1-6}$-alkyl, wherein the aryl or heteroaryl part is optionally substituted with one or more substituents independently selected from $R^{51}$; or $C_{3-8}$-cycloalkyl, $C_{3-8}$-cycloalkenyl, $C_{3-8}$-cycloalkenyl-$C_{1-6}$-alkyl.

$R^{49}$ and $R^{50}$ are independently selected from hydrogen and $C_{1-6}$-alkyl.

$R^{51}$ is halogen, nitro, cyano, hydroxy, carboxy, —$CF_3$, $C_{1-6}$-alkyl, hydroxy-$C_{1-6}$-alkyl, or carboxy-$C_{1-6}$-alkyl.

$R^{52}$ and $R^{53}$ are independently $C_{1-6}$-alkyl, halogen, nitro, cyano, hydroxy, carboxy, —$CF_3$, —$S(O)_2CH_3$, or —$S(O)_2NH_2$ as well as any salt hereof with a pharmaceutically acceptable acid or base, or any optical isomer or mixture of optical isomers, including a racemic mixture, or any tautomeric forms, with the exception of the compounds

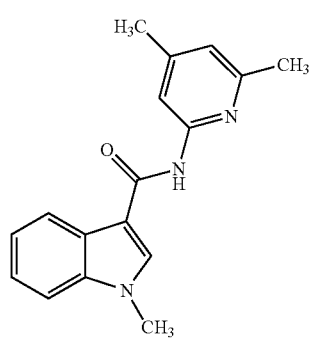

-continued

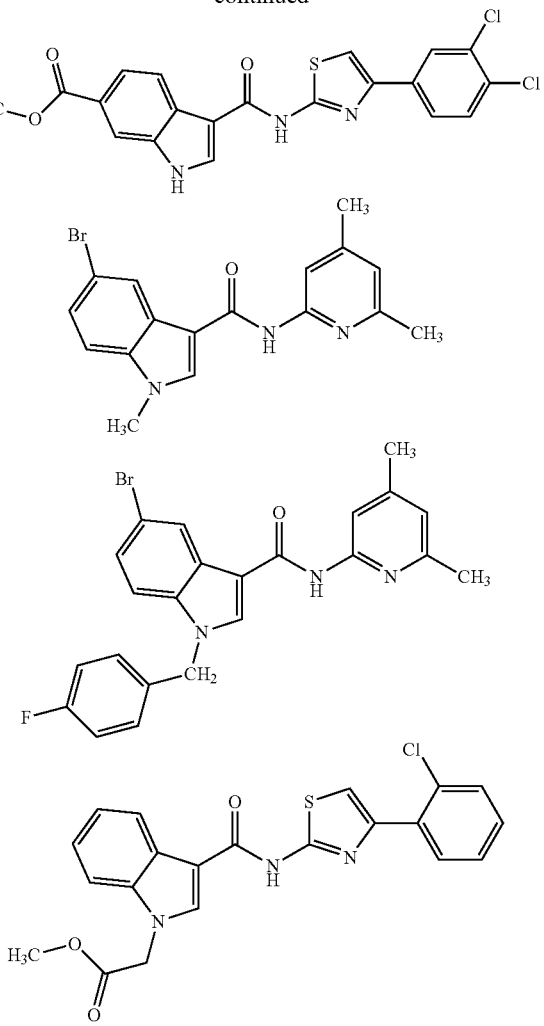

and with the proviso that if A is thiazolyl, then A cannot be substituted in the 4-position with $C_{5-8}$-cycloalkyl optionally substituted with $C_{1-4}$-alkyl, aryl optionally substituted with one or more substituents selected from halogen, $C_{1-6}$-alkyl, $C_{1-3}$ alkoxy or $C_{1-3}$ thioalkoxy, nitro, $CF_3$, heteroaryl substituted with one or more substituents selected from $C_{1-3}$-alkyl or halogen and with the proviso that if A is thiadiazolyl and B is unsubstituted indolyl or indolyl substituted on the nitrogen atom with —C(O)—$C_{1-4}$-alkyl, —$(CH_2)_nC(O)R$ wherein n is 1 or 2 and R is $OR^{1'}$ or $NR^{1'}R^{2'}$, $R^{1'}R^{2'}$ being selected from H or $C_{1-4}$-alkyl, Hydroxy-$C_{1-4}$-alkyl, $C_{2-6}$ alkoxyalkyl, tetrahydropyranyl, then A cannot be substituted in the 3-position with phenyl, pyridine, or pyrimidine, each of which may optionally be substituted with up to four substituents selected from Cl, Br, $C_{1-3}$-alkyl, or $C_{1-3}$-alkoxy and $CF_3$, naphtyl optionally substituted with halogen, $C_{1-3}$-alkyl, or $C_{1-3}$-alkoxy.

Embodiment 109

A compound according to any one of the embodiments 103 to 108 wherein B is

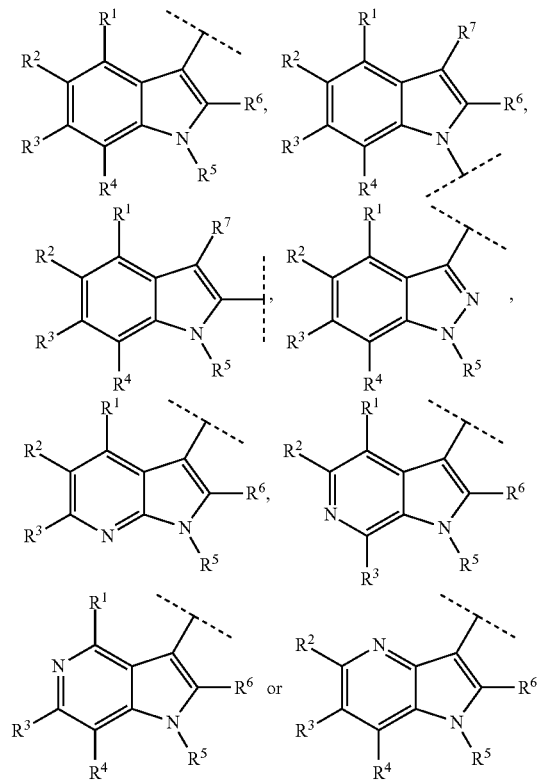

Embodiment 110

A compound according to embodiment 109 wherein B is

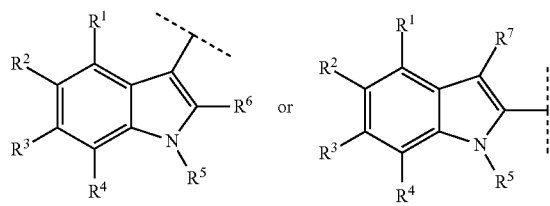

Embodiment 111

A compound according to embodiment 110 wherein B is

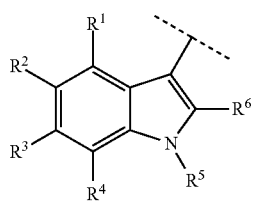

Embodiment 112

A compound according to embodiment 111 wherein B is

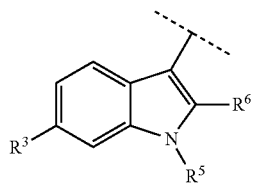

Embodiment 113

A compound according to embodiment 110 wherein B is

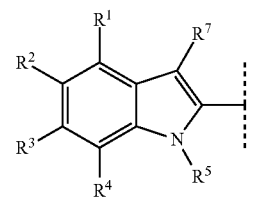

Embodiment 114

A compound according to embodiment 111 wherein B is

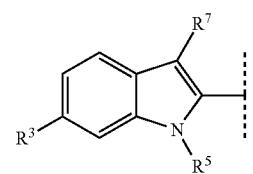

Embodiment 115

A compound according to any one of the embodiments 103 to 114 wherein at least one of the substituents $R^1$, $R^2$, $R^3$ and $R^4$ is different from H.

Embodiment 116

A compound according to embodiment 115 wherein $R^3$ is different from H.

Embodiment 117

A compound according to any one of the embodiments 103 to 116 wherein A is thiazolyl, oxazolyl, isoxazolyl, 1,3,4-thiadiazolyl-1,2,4-thiadiazolyl, 1,3,4-oxadiazolyl, 1,2,4-oxadiazolyl, pyrazolyl, 1,2,4-triazolyl, tetrazolyl, 3-oxo-pyrazolyl, 3-oxo-imidazolyl, 3-oxo-thiazolyl, thiazolidinyl, pyridyl, pyrimidinyl, pyrazinyl, 1,3,5-triazinyl, 1,2,4-triazinyl, benzimidazolyl, 4-oxo-pyrimidyl, pyridazinyl or 2-oxopyrimidyl, each of which may optionally be substituted with one or more substituents independently selected from R⁴⁰, R⁴¹ and R⁴².

Embodiment 118

A compound according to embodiment 117 wherein A isothiazolyl, 1,3,4-thiadiazolyl 1,2,4-thiadiazolyl, pyridyl, or pyrimidinyl, each of which may optionally be substituted with one or more substituents independently selected from R⁴⁰, R⁴¹ and R⁴².

Embodiment 119

A compound according to embodiment 118 wherein A isothiazolyl or 1,2,4-thiadiazolyl, each of which may optionally be substituted with one or more substituents independently selected from R⁴⁰, R⁴¹, and R⁴².

Embodiment 120

A compound according to embodiment 118 wherein A is

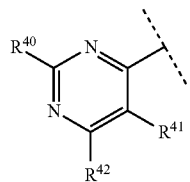

Embodiment 121

A compound according to any one of the embodiments 117 to 120 wherein A is

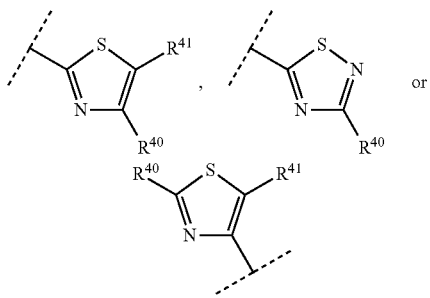

Embodiment 122

A compound according to embodiment 121 wherein A is

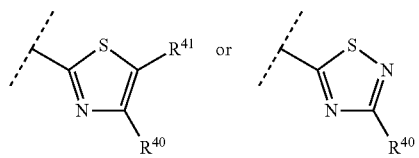

Embodiment 123

A compound according to embodiment 122 wherein A is

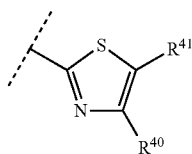

Embodiment 124

A compound according to embodiment 121 wherein A is

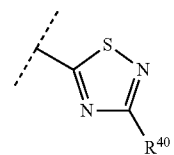

Embodiment 125

A compound according to any one of the embodiments 103 to 124 wherein R⁶ and R⁷ are hydrogen.

Embodiment 126

A compound according to any one of the embodiments 103 to 125 wherein R¹, R², R³ and R⁴ are independently selected from the group consisting of
hydrogen, halogen, cyano, hydroxy, carboxy, —CF₃; or —NR¹⁰R¹¹; or
$C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl-$C_{1-6}$-alkyl, heteroaryl-$C_{1-6}$-alkyl, $C_{1-6}$-alkoxy, aryl-$C_{1-6}$-alkoxy, aryloxy, heteroaryloxy, $C_{1-6}$-alkylthio, $C_{1-6}$-alkylsulfonyl, $C_{1-6}$-alkylsulfinyl, aryl, heteroaryl, $C_{1-6}$-alkyl-carbonyl, carboxy-$C_{1-6}$-alkyl, hydroxy-$C_{1-6}$-alkyl, di($C_{1-6}$-alkyl) amino-$C_{1-6}$-alkyl, $C_{1-6}$-alkylamino-$C_{1-6}$-alkyl, or carboxy-$C_{1-6}$-alkyloxy, each of which is optionally substituted with one or more substituents independently selected from R¹²; or
—CO—NR¹³R¹⁴, $C_{1-6}$-alkyl-O—$C_{1-6}$-alkyl, —C(O)—$C_{3-8}$-cycloalkyl.

Embodiment 127

A compound according to embodiment 126 wherein R¹, R², R³ and R⁴ are independently selected from the group consisting of
hydrogen, halogen, cyano, hydroxy, carboxy, —CF₃; or —NR¹⁰R¹¹; or
$C_{1-6}$-alkyl, benzyl, $C_{1-6}$-alkoxy, benzyloxy, phenyl, $C_{1-6}$-alkyl-carbonyl, carboxy-$C_{1-6}$-alkyl, hydroxy-$C_{1-6}$-alkyl, di($C_{1-6}$-alkyl)amino-$C_{1-6}$-alkyl, $C_{1-6}$-alkylamino-$C_{1-6}$-alkyl or carboxy-$C_{1-6}$-alkyloxy, each of which is optionally substituted with one or more substituents independently selected from R¹²; or
—CO—NR¹³R¹⁴.

Embodiment 128

A compound according to embodiment 127 wherein R¹, R², R³ and R⁴ are independently selected from the group consisting of hydrogen, halogen, hydroxy, carboxy, —CF$_3$; or
—NR$^{10}$R$^{11}$; or C$_{1-6}$-alkyl, carboxy-C$_{1-6}$-alkyl, hydroxy-C$_{1-6}$-alkyl, di(C$_{1-6}$-alkyl)amino-C$_{1-6}$-alkyl, C$_{1-6}$-alkylamino-C$_{1-6}$-alkyl or carboxy-C$_{1-6}$-alkyloxy, each of which is optionally substituted with one or more substituents independently selected from R$^{12}$; or

—CO—NR$^{13}$R$^{14}$.

Embodiment 129

A compound according to embodiment 128 wherein R$^1$, R$^2$, R$^3$ and R$^4$ are independently selected from the group consisting of hydrogen, F, Cl, Br, hydroxy, carboxy, —CF$_3$; or
—NR$^{10}$R$^{11}$; or methyl, ethyl, propyl, —CH$_2$—C(O)OH, —(CH$_2$)$_2$—C(O)OH, —CH$_2$—OH, —(CH$_2$)$_2$—OH, —O—CH$_2$—C(O)OH, —(CH$_2$)$_2$—N(CH$_3$)$_2$, —O—(CH$_2$)$_2$—C(O)OH; or

CO—NR$^{13}$R$^{14}$.

Embodiment 130

A compound according to any one of the embodiments 103 to 129 wherein R$^{10}$ and R$^{11}$ independently represent hydrogen, methyl, —C(O)—CH$_3$, —C(O)—CH$_2$CH$_3$, —CH$_2$—C(O)OH, —(CH$_2$)$_2$—C(O)OH, —C(O)—CH$_2$—C(O)OH, or —S(O)$_2$CH$_3$.

Embodiment 131

A compound according to embodiment 130 wherein R$^{10}$ is H and R$^{11}$ is hydrogen, methyl, —C(O)—CH$_3$, —C(O)—CH$_2$CH$_3$, —CH$_2$—C(O)OH, —(CH$_2$)$_2$—C(O)OH, —C(O)—CH$_2$—C(O)OH, or —S(O)$_2$CH$_3$.

Embodiment 132

A compound according to any one of the embodiments 103 to 131 wherein R$^{12}$ is halogen.

Embodiment 133

A compound according to any one of the embodiments 103 to 132 wherein R$^{13}$ and R$^{14}$ are independently selected from the group consisting of hydrogen, methyl, ethyl, or propyl.

Embodiment 134

A compound according to embodiment 133 wherein both R$^{13}$ and R$^{14}$ are hydrogen, or both are methyl, or both are ethyl, or both are propyl.

Embodiment 135

A compound according to any one of the embodiments 103 to 132 wherein R$^{13}$ and R$^{14}$ together with the nitrogen to which they are attached form a morpholine ring.

Embodiment 136

A compound according to any one of the embodiments 103 to 135 wherein R$^{15}$ is halogen.

Embodiment 137

A compound according to any one of the embodiments 103 to 136 wherein R$^5$ is selected from C$_{1-6}$-alkyl, C$_{2-6}$-alkenyl, C$_{2-6}$-alkynyl, C$_{3-8}$-cycloalkyl-C$_{1-6}$-alkyl, C$_{3-8}$-cycloalkenyl-C$_{1-6}$ alkyl, cyanomethyl, carboxymethyl, C$_{1-6}$-alkylcarbamoyl-C$_{1-6}$-alkyl, di-(C$_{1-6}$-alkyl)carbamoyl-C$_{1-6}$-alkyl; each of which may optionally be substituted with one or more substituents independently selected from R$^{32}$; or phenyl-C$_{1-6}$-alkyl, wherein the phenyl group may be substituted with one or more substituents independently selected from R$^{20}$; or heteroaryl-C$_{1-6}$-alkyl, C$_{3-8}$-heterocyclyl-C$_{1-6}$-alkyl wherein the heteroaryl or heterocyclyl group may be substituted with one or more substituents independently selected from R$^{26}$, wherein the heteroaryl part is selected from furyl, thienyl, pyrrolyl, pyrazolyl, 3-oxopyrazolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl, thiazolidinyl, 2-thiooxothiazolidinyl; or —C$_{1-6}$-alkyl-NR$^{28}$R$^{29}$; or
—CONR$^{30}$R$^{31}$.

Embodiment 138

A compound according to embodiment 137 wherein R$^5$ is selected from

C$_{1-6}$-alkyl, C$_{2-6}$-alkenyl, C$_{2-6}$-alkynyl, C$_{3-8}$-cycloalkyl-C$_{1-6}$-alkyl, C$_{3-8}$-cycloalkenyl-C$_{1-6}$-alkyl, cyanomethyl, carboxymethyl, C$_{1-6}$-alkylcarbamoylmethyl, di-(C$_{1-6}$-alkyl)carbamoylmethyl; each of which may optionally be substituted with one or more substituents independently selected from R$^{32}$; or Phenyl-C$_{1-6}$-alkyl, wherein the phenyl group may be substituted with one or more substituents independently selected from R$^{20}$; or Heteroaryl-C$_{1-6}$-alkyl, C$_{3-8}$-heterocyclyl-C$_{1-6}$-alkyl wherein the heteroaryl or heterocyclyl group may be substituted with one or more substituents independently selected from R$^{26}$, wherein the heteroaryl part is selected from furyl, thienyl, pyrrolyl, pyrazolyl, oxazolyl, thiazolyl, imidazolyl, 1,2,3-triazolyl, 1,2,4-triazolyl, pyranyl, pyridyl, pyrimidinyl, 1,2,3-thiadiazolyl, 1,2,4-thiadiazolyl, 1,2,5-thiadiazolyl, 1,3,4-thiadiazolyl, indolyl, isoindolyl, benzofuryl, benzothienyl, benzimidazolyl, benzoxazolyl, purinyl, quinolinyl, isoquinolinyl, or thiazolidinyl; or —C$_{1-6}$-alkyl-NR$^{28}$R$^{29}$; or
—CONR$^{30}$R$^{31}$.

Embodiment 139

A compound according to embodiment 138 wherein R$^5$ is selected from

C$_{1-6}$-alkyl, C$_{2-6}$-alkenyl, C$_{2-6}$-alkynyl, C$_{3-8}$-cycloalkyl-C$_{1-6}$-alkyl, C$_{3-8}$-cycloalkenyl-C$_{1-6}$-alkyl, each of which may optionally be substituted with one or more substituents independently selected from R$^{32}$; or Phenyl-$C_{1-6}$-alkyl, wherein the phenyl group may be substituted with one or more substituents independently selected from $R^{20}$; or —$C_{1-6}$-alkyl-$NR^{28}R^{29}$; or

—$CONR^{30}R^{31}$.

Embodiment 140

A compound according to embodiment 139 wherein $R^5$ is selected from $C_{1-6}$-alkyl, $C_{2-6}$-alkenyl, $C_{2-6}$-alkynyl, $C_{3-8}$-cycloalkyl-$C_{1-6}$-alkyl, $C_{3-8}$-cycloalkenyl-$C_{1-6}$-alkyl, each of which may optionally be substituted with one or more substituents independently selected from $R^{32}$; or Phenyl-$C_{1-6}$-alkyl, wherein the phenyl group may be substituted with one or more substituents independently selected from $R^{20}$.

Embodiment 141

A compound according to embodiment 140 wherein $R^5$ is selected from methyl, ethyl, propyl, isopropyl, butyl, isobutyl, sec-butyl, tert-butyl, n-pentyl, isopentyl, neopentyl, tert-pentyl, wherein each alkyl is optionally substituted with one or more substituents independently selected from $R^{32}$, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, ethynyl, 1-propynyl, 2-propynyl, 1-butynyl, 2-butynyl, 3-butynyl, 1-pentynyl, 2-pentynyl, 3-pentynyl, 4-pentynyl,

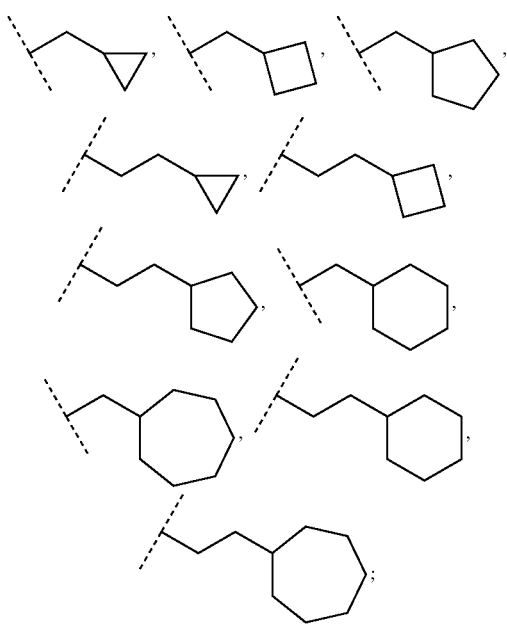

or

Phenyl-$C_{1-6}$-alkyl, wherein the phenyl group may be substituted with one or more substituents independently selected from $R^{20}$.

Embodiment 142

A compound according to embodiment 141 wherein $R^5$ is selected from methyl, ethyl, propyl, isopropyl, butyl, isobutyl, sec-butyl, tert-butyl, wherein each alkyl is optionally substituted with one or more substituents independently selected from $R^{32}$, vinyl, 1-propenyl, 2-propenyl, iso-propenyl, 1,3-butadienyl, 1-butenyl, 2-butenyl, 3-butenyl, 2-methyl-1-propenyl, 3-methyl-2-butenyl,

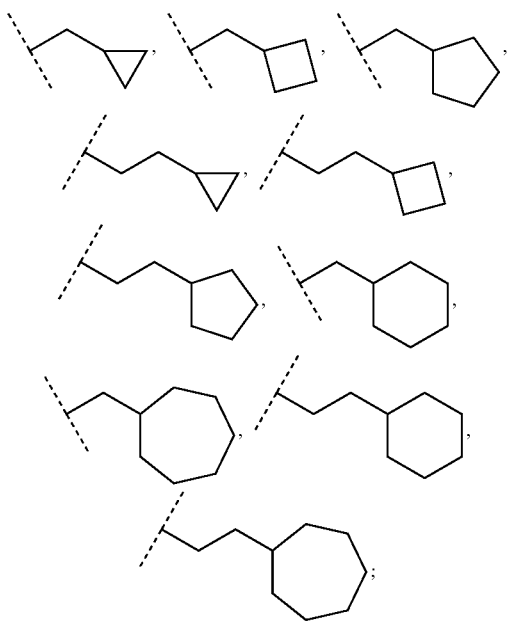

or

Phenyl-$C_{1-6}$-alkyl, wherein the phenyl group may be substituted with one or more substituents independently selected from $R^{20}$.

Embodiment 143

A compound according to embodiment 142 wherein $R^5$ is selected from methyl, ethyl, propyl, wherein each alkyl is optionally substituted with one or more substituents independently selected from $R^{32}$, 1-propenyl, 2-propenyl, iso-propenyl, 2-methyl-1-propenyl, 3-methyl-2-butenyl,

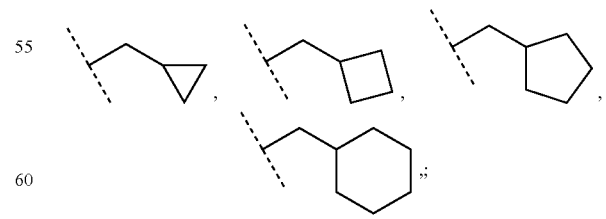

or

Benzyl, wherein the phenyl part may be substituted with one or more substituents independently selected from $R^{20}$.

Embodiment 144

A compound according to any one of the embodiments 103 to 143 wherein $R^{20}$ is
halogen, cyano, $CF_3$, hydroxy, carboxy; or
—C(O)—O—$C_{1-6}$-alkyl, $C_{1-6}$-alkoxy, $C_{1-6}$-alkyl, $C_{1-6}$-alkylthio, $C_{1-6}$-alkylsulfonyl, carboxy-$C_{1-6}$-alkyl, amino-$C_{1-6}$-alkyl, hydroxy-$C_{1-6}$-alkyl, each of which is optionally substituted with one or more substituents independently selected from $R^{21}$; or
—$NR^{22}R^{23}$, —$C_{1-6}$-alkyl-$NR^{22}R^{23}$; or
—$CONR^{24}R^{25}$.

Embodiment 145

A compound according to embodiment 144 wherein $R^{20}$ is
halogen, cyano, $CF_3$, hydroxy, carboxy; or
—C(O)—O—$C_{1-6}$-alkyl, $C_{1-6}$-alkoxy, $C_{1-6}$-alkyl, carboxy-$C_{1-6}$-alkyl, amino-$C_{1-6}$-alkyl, hydroxy-$C_{1-6}$-alkyl; or
—$NR^{22}R^{23}$ or
—$CONR^{24}R^{25}$.

Embodiment 146

A compound according to embodiment 145 wherein $R^{20}$ is
halogen, cyano, $CF_3$, hydroxy, carboxy; or
$C_{1-6}$-alkoxy, $C_{1-6}$-alkyl, carboxy-$C_{1-6}$-alkyl, amino-$C_{1-6}$-alkyl, hydroxy-$C_{1-6}$-alkyl.

Embodiment 147

A compound according to embodiment 146 wherein $R^{20}$ is halogen, cyano, $CF_3$, hydroxy, carboxy, —O—$CH_3$, —O—$(CH_3)_2$, methyl, ethyl, or propyl.

Embodiment 148

A compound according to any one of the embodiments 103 to 147 wherein $R^{21}$ is halogen.

Embodiment 149

A compound according to any one of the embodiments 103 to 148 wherein $R^{22}$ and $R^{23}$ are independently selected from hydrogen, —C(O)—$CH_2$, methyl, ethyl or propyl.

Embodiment 150

A compound according to any one of the embodiments 103 to 149 wherein $R^{24}$ and $R^{25}$ are independently selected from the group consisting of hydrogen, methyl, ethyl or propyl.

Embodiment 151

A compound according to any one of the embodiments 103 to 150 wherein $R^{26}$ is
halogen, nitro, cyano, hydroxy, carboxy; or
—C(O)—O—$C_{1-6}$-alkyl, $C_{1-6}$-alkoxy, $C_{1-6}$-alkyl, each of which is optionally substituted with one or more substituents independently selected from $R^{27}$.

Embodiment 152

A compound according to embodiment 151 wherein $R^{26}$ is halogen, cyano, hydroxy, carboxy, methoxy, ethoxy, methyl, ethyl or propyl.

Embodiment 153

A compound according to any one of the embodiments 103 to 152 wherein $R^{27}$ is halogen.

Embodiment 154

A compound according to any one of the embodiments 103 to 153 wherein $R^{28}$ and $R^{29}$ are independently selected from hydrogen or methyl.

Embodiment 155

A compound according to any one of the embodiments 103 to 154 wherein $R^{30}$ and $R^{31}$ are independently selected from hydrogen or methyl.

Embodiment 156

A compound according to any one of the embodiments 103 to 155 wherein $R^{32}$ is halogen or cyano.

Embodiment 157

A compound according to embodiment 156 wherein $R^{32}$ is halogen.

Embodiment 158

A compound according to any one of the embodiments 103 to 157 wherein $R^{40}$, $R^{41}$ and $R^{42}$ are independently selected from
halogen, carboxy, cyano, hydroxy, —$CF_3$, —SCN; or
$C_{1-6}$-alkyl, $C_{1-6}$-alkoxy, $C_{1-6}$-alkylthio, —C(O)—$C_{1-6}$-alkyl, —$C_{1-6}$-alkyl-O—$C_{1-6}$-alkyl, $C_{1-6}$-alkyl-S—$C_{1-6}$-alkyl, carboxy-$C_{1-6}$-alkyl, di($C_{1-6}$-alkyl)amino-$C_{1-6}$-alkyl, $C_{1-6}$-alkylamino-$C_{1-6}$-alkyl, or hydroxy-$C_{1-6}$-alkyl, each of which is optionally substituted with one or more substituents independently selected from $R^{43}$; or
phenyl-$C_{1-6}$-alkyl, naphtyl-$C_{1-6}$-alkyl, heteroaryl-$C_{1-6}$-alkyl, phenyl-$C_{1-6}$-alkylthio, naphtyl-$C_{1-6}$-alkylthio, heteroaryl-$C_{1-6}$-alkylthio, heteroaryl-thio-$C_{1-6}$-alkyl, phenyloxy, heteroaryloxy, or heteroarylthio, wherein each heteroaryl part is selected from furyl, thienyl, pyrrolyl, pyrazolyl, oxazolyl, thiazolyl, imidazolyl, 1,2,3-triazolyl, 1,2,4-triazolyl, pyranyl, pyridyl, pyrimidinyl, 1,2,3-thiadiazolyl, 1,2,4-thiadiazolyl, 1,2,5-thiadiazolyl, 1,3,4-thiadiazolyl, indolyl, isoindolyl, benzofuryl, benzothienyl, benzimidazolyl, benzoxazolyl, purinyl, quinolinyl, isoquinolinyl, or thiazolidinyl, and wherein each aryl or heteroaryl part is optionally substituted with one or more substituents independently selected from $R^{44}$; or
$C_{3-8}$-cycloalkyl, $C_{3-8}$-cycloalkyl-$C_{1-6}$-alkyl, each of which is optionally substituted on the cycloalkyl part with one or more substituents independently selected from $R^{45}$; or
—$NR^{46}R^{47}$, —$C_{1-6}$-alkyl-$NR^{46}R^{47}$, —$C_{1-6}$-alkyl-S(O)—$R^{48}$, —$C_{1-6}$-alkyl-S(O)_2$—$R^{48}$ wherein each alkyl part may be substituted with one or more substituents independently selected from $R^{52}$;
two of $R^{40}$, $R^{41}$ and $R^{42}$ can be taken together to form a $C_{2-5}$-alkylene bridge.

Embodiment 159

A compound according to embodiment 158 wherein $R^{40}$, $R^{41}$ and $R^{42}$ are independently selected from halogen, cyano, —$CF_3$, —SCN; or methyl, ethyl propyl, butyl, methoxy, ethoxy, —C(O)—$CH_3$, —C(O)—$CH_2CH_3$, —$CH_2OH$, —$CH_2CH_2OH$, —$(CH_2)_2$—$N(CH_3)_2$, —$CH_2$—O—$CH_2$, —$CH_2CH_2$—O—$CH_2$, —$CH_2$—S—$CH_2$, —$CH_2CH_2$—S—$CH_2$; or phenyl-methyl, phenyl-ethyl, naphtyl-methyl, naphtyl-ethyl, heteroaryl-methyl, heteroaryl-ethyl, phenyl-methylthio, phenyl-ethylthio, heteroaryl-methylthio, heteroaryl-ethylthio, heteroaryl-thio-methyl, heteroaryl-thio-ethyl, each of which is optionally substituted on the aryl or heteroaryl part with one or more substituents independently selected from $R^{44}$ and wherein heteroaryl is selected from

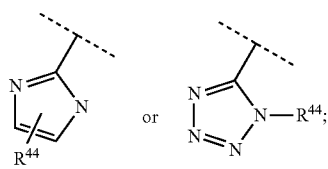

or

Cyclopropyl, cyclobutyl, cyclopentyl, cyclohexyl, cyclopropyl-methyl, cyclobutyl-methyl, cyclopentyl-methyl, cyclohexyl-methyl, cyclopropyl-ethyl, cyclobutyl-ethyl, cyclopentylethyl, cyclohexyl-ethyl, each of which is optionally substituted on the cycloalkyl part with one or more substituents independently selected from $R^{45}$; or two of $R^{40}$, $R^{41}$ and $R^{42}$ can be taken together to form a $C_{2-5}$-alkylene bridge.

Embodiment 160

A compound according to embodiment 159 wherein $R^{40}$, $R^{41}$ and $R^{42}$ are independently selected from halogen, cyano, —$CF_3$, —SCN; or methyl, ethyl, —C(O)—$CH_3$, —$CH_2OH$, —$CH_2CH_2OH$, —$CH_2$—O—$CH_2$, —$CH_2CH_2$—O—$CH_2$, —$CH_2$—S—$CH_2$, —$CH_2CH_2$—S—$CH_2$; or heteroaryl-methyl, heteroaryl-ethyl, phenyl-methylthio, phenyl-ethylthio, heteroaryl-thio-methyl, heteroaryl-thio-ethyl, each of which is optionally substituted on the aryl or heteroaryl part with one or more substituents independently selected from $R^{44}$ and wherein heteroaryl is selected from

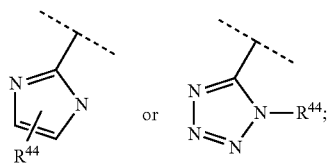

or

Cyclopropyl, cyclobutyl, cyclopentyl, cyclohexyl, cyclopropyl-methyl, cyclobutyl-methyl, cyclopentyl-methyl, cyclohexyl-methyl, cyclopropyl-ethyl, cyclobutyl-ethyl, cyclopentylethyl, cyclohexyl-ethyl, each of which is optionally substituted on the cycloalkyl part with one or more substituents independently selected from $R^{45}$; or two of $R^{40}$, $R^{41}$ and $R^{42}$ can be taken together to form a $C_{2-5}$-alkylene bridge.

Embodiment 161

A compound according to embodiment 160 wherein $R^{40}$, $R^{41}$ and $R^{42}$ are independently selected from halogen, cyano, —$CF_3$, —SCN; or methyl, ethyl, —C(O)—$CH_3$, —$CH_2OH$, —$CH_2CH_2OH$, —$CH_2$—O—$CH_2$, —$CH_2CH_2$—O—$CH_2$, —$CH_2$—S—$CH_2$, —$CH_2CH_2$—S—$CH_2$; or

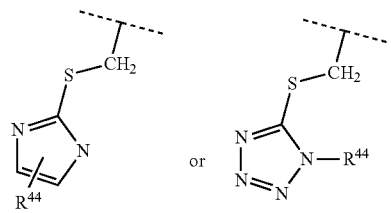

Embodiment 162

A compound according to any one of the embodiments 103 to 161 wherein $R^{43}$ is $C_{1-6}$-alkyl, halogen, cyano, hydroxy, carboxy, —C(O)—O—$C_{1-6}$-alkyl or —$CF_3$.

Embodiment 163

A compound according to embodiment 162 wherein $R^{43}$ is methyl, ethyl, —C(O)—O—$CH_3$, —C(O)—O—$CH_2CH_3$, —C(O)—O—$CH_2CH_2CH_3$, or halogen.

Embodiment 164

A compound according to any one of the embodiments 103 to 163 wherein $R^{44}$ is $C_{1-6}$-alkyl, halogen, nitro, cyano, hydroxy, carboxy, —$CF_3$, or carboxy-$C_{1-6}$-alkyl.

Embodiment 165

A compound according to embodiment 164 wherein $R^{44}$ is methyl, ethyl, halogen, —$CH_2$—COOH, or —$CH_2$—$CH_2$—COOH.

Embodiment 166

A compound according to any one of the embodiments 103 to 165 wherein $R^{45}$ is $C_{1-6}$-alkyl, halogen, nitro, cyano, hydroxy, carboxy, —$CF_3$, or carboxy-$C_{1-6}$-alkyl.

Embodiment 167

A compound according to embodiment 166 wherein $R^{45}$ is methyl, ethyl, halogen, —$CH_2$—COOH, or —$CH_2$—$CH_2$—COOH.

Embodiment 168

A compound according to any one of the embodiments 103 to 167 wherein $R^{46}$ and $R^{47}$ independently represent hydrogen, methyl, ethyl, hydroxy-methyl, hydroxy-methyl, carboxy-methyl, carboxy-ethyl, or phenyl, or $R^{44}$ and $R^{45}$ together with the nitrogen to which they are attached form a heterocycle selected from piperazine, homopiperazine or morpholine.

Embodiment 169

A compound according embodiment 168 wherein $R^{46}$ and $R^{47}$ independently represent hydrogen, methyl, ethyl, or phenyl, or $R^{44}$ and $R^{45}$ together with the nitrogen to which they are attached form a heterocycle selected from piperazine, homopiperazine or morpholine.

Embodiment 170

A compound according to any one of the embodiments 103 to 169 wherein $R^{48}$ is selected from
- carboxy-methyl, carboxy-ethyl, hydroxy-methyl or hydroxy-ethyl; or
- phenyl, naphtyl, heteroaryl, phenylmethyl, phenylethyl, heteroaryl-methyl or heteroaryl-methyl, wherein each heteroaryl part is selected from furyl, thienyl, pyrrolyl, pyrazolyl, oxazolyl, thiazolyl, imidazolyl, 1,2,3-triazolyl, 1,2,4-triazolyl, pyranyl, pyridyl, pyrimidinyl, 1,2,3-thiadiazolyl, 1,2,4-thiadiazolyl, 1,2,5-thiadiazolyl, 1,3,4-thiadiazolyl, indolyl, isoindolyl, benzofuryl, benzothienyl, benzimidazolyl, benzoxazolyl, purinyl, quinolinyl, isoquinolinyl, tetrazolyl, or thiazolidinyl, and wherein the aryl or heteroaryl part is optionally substituted with one or more substituents independently selected from $R^{51}$; or
- $C_{3-8}$-cycloalkyl, $C_{3-8}$-cycloalkyl-methyl or $C_{3-8}$-cycloalkyl-ethyl.

Embodiment 171

A compound according to embodiment 170 wherein $R^{48}$ is selected from
- carboxy-methyl, carboxy-ethyl, hydroxy-methyl or hydroxy-ethyl; or
- phenyl, heteroaryl, phenylmethyl, phenylethyl, heteroaryl-methyl or heteroaryl-methyl, wherein each heteroaryl part is selected from imidazolyl, 1,2,3-triazolyl, 1,2,4-triazolyl, or tetrazolyl, and wherein the aryl or heteroaryl part is optionally substituted with one or more substituents independently selected from $R^{51}$; or
- Cyclopropyl, cyclobutyl, cyclopentyl, cyclohexyl, cyclopropyl-methyl, cyclobutyl-methyl, cyclopentyl-methyl, cyclohexyl-methyl, cyclopropyl-ethyl, cyclobutyl-ethyl, cyclopentylethyl, or cyclohexyl-ethyl.

Embodiment 172

A compound according to embodiment 171 wherein $R^{48}$ is selected from
- carboxy-methyl, carboxy-ethyl, hydroxy-methyl or hydroxy-ethyl; or
- phenyl, heteroaryl, phenylmethyl, phenylethyl, heteroaryl-methyl or heteroaryl-methyl, wherein each heteroaryl part is selected from imidazolyl, 1,2,3-triazolyl, 1,2,4-triazolyl, or tetrazolyl, and wherein the aryl or heteroaryl part is optionally substituted with one or more substituents independently selected from $R^{51}$; or
- Cyclopropyl, cyclobutyl, or cyclopentyl.

Embodiment 173

A compound according to any one of the embodiments 103 to 172 wherein $R^{49}$ and $R^{50}$ are independently selected from hydrogen, methyl and ethyl.

Embodiment 174

A compound according to embodiment 173 wherein $R^{49}$ and $R^{50}$ are both hydrogen.

Embodiment 175

A compound according to any one of the embodiments 103 to 174 wherein $R^{51}$ is halogen, cyano, hydroxy, carboxy, —$CF_3$, methyl, ethyl, hydroxy-methyl, hydroxy-ethyl, carboxy-methyl or carboxy-ethyl.

Embodiment 176

A compound according to embodiment 175 wherein $R^{51}$ is methyl, ethyl, hydroxy-methyl, hydroxy-ethyl, carboxy-methyl or carboxy-ethyl.

Embodiment 177

A compound according to any one of the embodiments 103 to 176 wherein $R^{52}$ is halogen, cyano, hydroxy, carboxy, —$CF_3$, methyl, ethyl, hydroxy-methyl, hydroxy-ethyl, carboxy-methyl or carboxy-ethyl.

Embodiment 178

A compound according to any one of the embodiments 103 to 177 wherein $R^{53}$ is halogen, cyano, hydroxy, carboxy, —$CF_3$, methyl, ethyl, hydroxy-methyl, hydroxy-ethyl, carboxy-methyl or carboxy-ethyl.

Embodiment 179

A compound according to any one of the embodiments 103 to 178, which compound is an activator of glucokinase, when tested in the Glucokinase Activation Assay (I) disclosed herein at a glucose concentration of 2 mM.

Embodiment 180

A compound according to any one of the embodiments 103 to 179, which compound is an activator of glucokinase, when tested in the Glucokinase Activation Assay (I) disclosed herein at a glucose concentration of from 10 to 15 mM.

Embodiment 181

A compound according to any one of the embodiments 103 to 180, which compound, at a concentration of 30 μM, is capable of providing an at least 1.5, such as at least 1.7, for instance at least 2.0 fold activation of glucokinase in the Glucokinase Activation Assay (I) disclosed herein at a glucose concentration of 2 mM.

Embodiment 182

A compound according to any one of the embodiments 103 to 181, which compound, at a concentration of 30 μM, is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment 183

A compound according to any one of the embodiments 103 to 182, which at a concentration of 5 µM is capable of providing an at least 1.5, such as at least 1.7, for instance at least 2.0 fold activation of glucokinase in the Glucokinase Activation Assay (I) disclosed herein at a glucose concentration of 2 mM.

Embodiment 184

A compound according to any one of the embodiments 103 to 183, which at a concentration of 5 µM is capable of providing an at least 1.5, such as at least 1.7, for instance at least 2.0 fold activation of glucokinase in the Glucokinase Activation Assay (I) disclosed herein at a glucose concentration of from 10 to 15 mM.

Embodiment 185

A compound according to any one of the embodiments 103 to 184, which compound provides an increase in glucokinase activity, where the increase in glucokinase activity provided by the compound increases with increasing concentrations of glucose.

Embodiment 186

A compound according to embodiment 184 or embodiment 185, which provides an increase in glucokinase activity in Glucokinase Activation Assay (I) disclosed herein at a glucose concentration of 15 mM, which increase is significantly higher than the increase in glucokinase activity provided by the compound in Glucokinase Activation Assay (I) disclosed herein at a glucose concentration of 5 mM.

Embodiment 187

A compound according to any one of the embodiments 184 to 186, which at a compound concentration of 10 µM provides an increase in glucokinase activity in Glucokinase Activation Assay (I) disclosed herein at a glucose concentration of 15 mM, which increase is significantly higher than the increase in glucokinase activity provided by the compound at a compound concentration of 10 µM in Glucokinase Activation Assay (I) disclosed herein at a glucose concentration of 5 mM.

Embodiment 188

A compound according to any one of the embodiments 184 to 187, which at a compound concentration of 10 µM provides an increase in glucokinase activity in Glucokinase Activation Assay (I) disclosed herein at a glucose concentration of 15 mM, which increase is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the increase in glucokinase activity provided by the compound at a compound concentration of 10 µM in Glucokinase Activation Assay (I) disclosed herein at a glucose concentration of 5 mM.

Embodiment 189

A compound according to any one of the embodiments 103 to 188, which compound increases glucose utilization in the liver without inducing any increase in insulin secretion in response to glucose.

Embodiment 190

A compound according to any one of the embodiments 103 to 188, which compound shows a significantly higher activity in isolated hepatocytes compared to the activity of the compound in Ins-1 cells.

Embodiment 191

A compound according to any one of the embodiments 188 to 190, which compound shows a significantly higher activity in isolated hepatocytes measured as described in the Glucokinase Activity Assay (II) compared to the activity of the compound in Ins-1 cells measured as described in the Glucokinase Activity Assay (III).

Embodiment 192

A compound according to embodiment 191, which compound shows an activity in isolated hepatocytes measured as described in the Glucokinase Activity Assay (II) which activity is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the compound in Ins-1 cells measured as described in the Glucokinase Activity Assay (III).

Embodiment 193

A compound according to embodiment 191, which compound shows no activity in the Ins-1 cells measured as described in the Glucokinase Activity Assay (III).

Embodiment 194

A compound according to any one of embodiments 103 to 193 for use as a medicament.

Embodiment 195

A compound according to any one of embodiments 103 to 193 for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

Embodiment 196

A pharmaceutical composition comprising, as an active ingredient, at least one compound according to any one of embodiments 103 to 195 together with one or more pharmaceutically acceptable carriers or excipients.

Embodiment 197

A pharmaceutical composition according to embodiment 89 in unit dosage form, comprising from about 0.05 mg to about 1000 mg, preferably from about 0.1 mg to about 500 mg and especially preferred from about 0.5 mg to about 200 mg of the compound according to any one of embodiments 103 to 195.

Embodiment 198

Use of a compound according to any one of the embodiments 103 to 195 for the preparation of a medicament for increasing the activity of glucokinase.

Embodiment 199

The use according to embodiment 198 for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins.

Embodiment 200

The use according to embodiment 198 for the preparation of a medicament for the adjuvant treatment of type 1 diabetes for preventing the onset of diabetic complications.

Embodiment 201

The use according to embodiment 198 for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

Embodiment 202

Use according to any one of the embodiments 198 to 201 in a regimen which comprises treatment with a further antidiabetic agent.

Embodiment 203

Use according to any one of the embodiments 198 to 202 in a regimen which comprises treatment with a further antihyperlipidemic agent.

Embodiment 204

Use according to any one of embodiments 198 to 203 in a regimen which comprises treatment with a further antiobesity agent.

Embodiment 205

Use according to any one of embodiments 198 to 204 in a regimen which comprises treatment with a further antihypertensive agent.

Included within the scope of the present invention are the individual enantiomers of the compounds represented by the above formulae as well as any wholly or partially racemic mixtures thereof. The present invention also covers the individual enantiomers of the compounds represented by the above formulae above as mixtures with diastereoisomers thereof in which one or more stereocenters are inverted.

In one embodiment of the present invention, the present compounds are used for the preparation of a medicament for the treatment of hyperglycemia. As used herein hyperglycemia is to be taken as generally understood in the art, with reference for example to the Report of the Expert Committee of the Diagnosis and Classification of Diabetes Mellitus, published in Diabetes Care 20, 1183-1197, (1997), but is usually taken to mean an elevated plasma glucose level exceeding about 110 mg/dl. The present compounds are effective in lowering the blood glucose both in the fasting and postprandial stage.

In one embodiment of the present invention, the present compounds are used for the preparation of a pharmaceutical composition for the treatment of IGT.

In one embodiment of the present invention, the present compounds are used for the preparation of a pharmaceutical composition for the treatment of Syndrome X.

In one embodiment of the present invention, the present compounds are used for the preparation of a pharmaceutical composition for the treatment of type 2 diabetes. Such treatment includes i.a. treatment for the purpose of the delaying of the progression from IGT to type 2 diabetes as well as delaying the progression from non-insulin requiring type 2 diabetes to insulin requiring type 2 diabetes.

In one embodiment of the present invention the present compounds are used for the preparation of a pharmaceutical composition for the treatment of type 1 diabetes. Such therapy is normally accompanied by insulin administration.

In one embodiment of the present invention the present compounds are used for the preparation of a pharmaceutical composition for the treatment of dyslipidemia and hyperlipidemia.

In one embodiment of the present invention the present compounds are used for the preparation of a pharmaceutical composition for the treatment of obesity.

In another aspect of the present invention treatment of a patient with the present compounds are combined with diet and/or exercise.

The present invention provides methods of activating glucokinase activity in a mammal, which methods comprise administering, to a mammal in need of activation of glucokinase activity, a therapeutically defined amount of a compound according to the present invention defined above, as a single or polymorphic crystalline form or forms, an amorphous form, a single enantiomer, a racemic mixture, a single stereoisomer, a mixture of stereoisomers, a single diastereoisomer, a mixture of diastereoisomers, a solvate, a pharmaceutically acceptable salt, a solvate, a prodrug, a biohydrolyzable ester, or a biohydrolyzable amide thereof.

The present invention provides a method of activating glucokinase, comprising the step of administering to a mammal in need thereof a pharmacologically effective amount of a compound according to the present invention. The invention further provides a pharmaceutical composition comprising a pharmaceutically acceptable carrier and a pharmacologically effective amount of a compound according to the present invention sufficient to activate glucokinase. A glucokinase-activating amount can be an amount that reduces or inhibits a Glucokinase activity in the subject.

Additionally provided by the present invention is a pharmaceutical composition comprising a pharmaceutically acceptable carrier and a pharmacologically effective amount of a compound according to the present invention sufficient to treat type I diabetes.

Also provided by the present invention is a pharmaceutical composition comprising a pharmaceutically acceptable carrier and a pharmacologically effective amount of a compound according to the present invention sufficient to treat type II diabetes.

The compounds of the present invention can be administered to any mammal in need of activation of glucokinase activity. Such mammals can include, for example, horses, cows, sheep, pigs, mice, dogs, cats, primates such as chimpanzees, gorillas, rhesus monkeys, and, most preferably humans.

Combination Treatment

In a further aspect of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, aglucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In one embodiment of the present invention, the present compounds are administered in combination with a sulphonylurea eg tolbutamide, chlorpropamide, tolazamide, glibenclamide, glipizide, glimepiride, glicazide or glyburide.

In one embodiment of the present invention, the present compounds are administered in combination with a biguanide eg metformin.

In one embodiment of the present invention, the present compounds are administered in combination with a meglitinide eg repaglinide or senaglinide/nateglinide.

In one embodiment of the present invention, the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

In one embodiment of the present invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In one embodiment of the present invention the present compounds are administered in combination with an α-glucosidase inhibitor eg voglibose, emiglitate, miglitol or acarbose.

In one embodiment of the present invention the present compounds are administered in combination with a glycogen phosphorylase inhibitor eg the compounds described in WO 97/09040 (Novo Nordisk A/S).

In one embodiment of the present invention the present compounds are administered in combination with an agent acting on the ATP-dependent potassium channel of the pancreatic β-cells eg tolbutamide, glibenclamide, glipizide, glicazide, BTS-67582 or repaglinide.

In one embodiment of the present invention the present compounds are administered in combination with nateglinide.

In one embodiment of the present invention the present compounds are administered in combination with an antihyperlipidemic agent or a antilipidemic agent eg cholestyramine, colestipol, clofibrate, gemfibrozil, lovastatin, pravastatin, simvastatin, probucol or dextrothyroxine.

Furthermore, the compounds according to the invention may be administered in combination with one or more antiobesity agents or appetite regulating agents.

Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists, ciliary neurotrophic factor, and oxyntomodulin. Further antiobesity agents are bupropion (antidepressant), topiramate (anticonvulsant), ecopipam (dopamine D1/D5 antagonist) and naltrexone (opioid antagonist).

In one embodiment of the present invention the antiobesity agent is leptin.

In one embodiment of the present invention the antiobesity agent is a serotonin and norepinephrine reuptake inhibitor eg sibutramine.

In one embodiment of the present invention the antiobesity agent is a lipase inhibitor eg orlistat.

In one embodiment of the present invention the antiobesity agent is an adrenergic CNS stimulating agent eg dexamphetamine, amphetamine, phentermine, mazindol phendimetrazine, diethylpropion, fenfluramine or dexfenfluramine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In one embodiment of the present invention, the present compounds are administered in combination with insulin, insulin derivatives or insulin analogues.

In one embodiment of the invention the insulin is an insulin derivative is selected from the group consisting of B29-N$^\epsilon$-myristoyl-des(B30) human insulin, B29-N$^\epsilon$-palmitoyl-des(B30) human insulin, B29-N$^\epsilon$-myristoyl human insulin, B29-N$^\epsilon$-palmitoyl human insulin, B28-N$^\epsilon$-myristoyl Lys$^{B28}$Pro$^{B29}$ human insulin, B28-N$^\epsilon$-palmitoyl Lys$^{B28}$Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$-(N-lithocholyl-γ-glutamyl)-des(B30) human insulin, B29-N$^\epsilon$-(ω-carboxyheptadecanoyl)-des(B30) human insulin and B29-N$^\epsilon$-(ω-carboxyheptadecanoyl) human insulin.

In another embodiment of the invention the insulin derivative is B29-N$^\epsilon$-myristoyl-des(B30) human insulin.

In a further embodiment of the invention the insulin is an acid-stabilised insulin. The acid-stabilised insulin may be selected from analogues of human insulin having one of the following amino acid residue substitutions:
A21G
A21G, B28K, B29P
A21G, B28D
A21G, B28E
A21G, B3K, B29E
A21G, desB27
A21G, B9E
A21G, B9D
A21G, B10E insulin.

In a further embodiment of the invention the insulin is an insulin analogue. The insulin analogue may be selected from the group consisting of
i. An analogue wherein position B28 is Asp, Lys, Leu, Val, or Ala and position B29 is Lys or Pro; and
ii. des(B28-B30), des(B27) or des(B30) human insulin.

In another embodiment the analogue is an analogue of human insulin wherein position B28 is Asp or Lys, and position B29 is Lys or Pro.

In another embodiment the analogue is des(B30) human insulin.

In another embodiment the insulin analogue is an analogue of human insulin wherein position B28 is Asp.

In another embodiment the analogue is an analogue wherein position B3 is Lys and position B29 is Glu or Asp.

In another embodiment the GLP-1 derivative to be employed in combination with a compound of the present invention refers to GLP-1(1-37), exendin-4(1-39), insulinotropic fragments thereof, insulinotropic analogues thereof and insulinotropic derivatives thereof. Insulinotropic fragments of GLP-1(1-37) are insulinotropic peptides for which the entire sequence can be found in the sequence of GLP-1(1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1(7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogues of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1(1-37) are e.g. Met$^8$-GLP-1(7-37) wherein the alanine in position 8 has been replaced by methionine and the amino acid residues in position 1 to 6 have been deleted, and Arg$^{34}$-GLP-1(7-37) wherein the valine in position 34 has been replaced with arginine and the amino acid residues in position 1 to 6 have been deleted. An example of an insulinotropic analogue of exendin-4(1-39) is Ser$^2$Asp$^3$-exendin-4(1-39) wherein the amino acid residues in position 2 and 3 have been replaced with serine and aspartic acid, respectively (this particular analogue also being known in the art as exendin-3). Insulinotropic derivatives of GLP-1(1-37), exendin-4(1-39) and analogues thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogues thereof are GLP-1(7-36)-amide, Arg$^{34}$, Lys$^{26}$(N$^\epsilon$-(γ-Glu(N$^\alpha$-hexadecanoyl)))-GLP-1(7-37) and Tyr$^{31}$-exendin-4(1-31)-amide. Further examples of GLP-1(1-37), exendin-4(1-39), insulinotropic fragments thereof, insulinotropic analogues thereof and insulinotropic derivatives thereof are described in WO 98/08871, WO 99/43706, U.S. Pat. No. 5,424,286 and WO 00/09666.

In another aspect of the present invention, the present compounds are administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

It should be understood that any suitable combination of the compounds according to the invention with diet and/or exercise, one or more of the above-mentioned compounds and optionally one or more other active substances are considered to be within the scope of the present invention. In one embodiment of the present invention, the pharmaceutical composition according to the present invention comprises e.g. a compound of the invention in combination with metformin and a sulphonylurea such as glyburide; a compound of the invention in combination with a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds of this invention which are generally prepared by reacting the free base with a suitable organic or inorganic acid or by reacting the acid with a suitable organic or inorganic base. When a compound according to the present invention contains a free base such salts are prepared in a conventional manner by treating a solution or suspension of the compound with a chemical equivalent of a pharmaceutically acceptable acid. When a compound according to the present invention contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the present invention and these form a further aspect of the present invention.

For parenteral administration, solutions of the novel compounds of the above formulae in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the present invention.

Thus, in a further embodiment, there is provided a pharmaceutical composition comprising a compound according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ®IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the present invention may comprise a compound according to the present invention in combination with further active substances such as those described in the foregoing.

The present invention also provides a method for the synthesis of compounds useful as intermediates in the preparation of compounds of the above formulae along with methods for the preparation of such compounds. The compounds can be prepared readily according to the following reaction Schemes (in which all variables are as defined before, unless so specified) using readily available starting materials, reagents and conventional synthesis procedures. In these reactions, it is also possible to make use of variants which are themselves known to those of ordinary skill in this art, but are not mentioned in greater detail.

EXAMPLES

HPLC-MS

Method A

The following instrumentation is used:
Hewlett Packard series 1100 G1312A Bin Pump
Hewlett Packard series 1100 Column compartment
Hewlett Packard series 1100 G1315A DAD diode array detector
Hewlett Packard series 1100 MSD
Sedere 75 Evaporative Light Scattering detector The instrument is controlled by HP Chemstation software.
The HPLC pump is connected to two eluent reservoirs containing:
A: 0.01% TFA in water
B: 0.01% TFA in acetonitrile The analysis is performed at 40° C. by injecting an appropriate volume of the sample (preferably 1 µl) onto the column which is eluted with a gradient of acetonitrile.

The HPLC conditions, detector settings and mass spectrometer settings used are given in the following table.

| Column | Waters Xterra MS C-18 X 3 mm id 5 µm |
|---|---|
| Gradient | 5%-100% acetonitrile linear during 7.5 min at 1.5 mL/min |
| Detection | 210 nm (analogue output from DAD) |
| | ELS (analogue output from ELS) |
| MS | ionisation mode API-ES |
| | Scan 100-1000 amu step 0.1 amu |

After the DAD the flow is divided yielding approximately 1 mL/min to the ELS and 0.5 mL/min to the MS.

HPLC-MS

Method B

The following instrumentation is used:
Hewlett Packard series 1100 MSD G1946A Single quadropole mass spectrometer
Hewlett Packard series 1100 MSD G1312A Bin pump
Hewlett Packard series 1100 MSD G1313A ALS autosampler
Hewlett Packard series 1100 MSD G1315A diode array detector (DAD)

The HP LC/MSD ChemStation control software running on a HP Vectra computer is used for the instrument control and data acquisition.

The HPLC pump is connected to two eluent reservoirs containing:
A: 0.01% TFA in water
B: 0.01% TFA in acetonitrile The analysis is performed at room temperature by injecting 1 µL of the sample solution on the column which is eluted with a gradient of acetonitrile in 0.01% TFA.

The HPLC conditions, detector settings and mass spectrometer settings used are given in the following table.

| Column | Waters Xterra 100 A MS C-18 3.5 µm, 3.0 mm × 50 mm |
|---|---|
| Gradient | 10%-100% acetonitrile in 0.05% TFA linearly during 4.5 min at 1.5 mL/min |
| Detection | UV: 210 nm (diode array) |
| MS | Ionisation mode: API-ES |
| | Experiment: Start: 100 amu Stop: 1000 amu Step: 0.1 amu |

HPLC-MS

Method C

The following instrumentation is used:
Sciex API 100 Single quadropole mass spectrometer
Perkin Elmer Series 200 Quard pump
Perkin Elmer Series 200 autosampler
Applied Biosystems 785A UV detector
Sedex 55 evaporative light scattering detector
A Valco column switch with a Valco actuator controlled by timed events from the pump.

The Sciex Sample control software running on a Macintosh PowerPC 7200 computer is used for the instrument control and data acquisition.

The HPLC pump is connected to four eluent reservoirs containing:
A: Acetonitrile
B: Water
C: 0.5% TFA in water
D: 0.02 M ammonium acetate The requirements for the samples are that they contain approximately 500 μg/mL of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis is performed at room temperature by injecting 20 μl of the sample solution on the column, which is eluted with a gradient of acetonitrile in either 0.05% TFA or 0.002 M ammonium acetate. Depending on the analysis method varying elution conditions are used.

The eluate from the column is passed through a flow splitting T-connector, which passed approximately 20 μl/min through approx. 1 m 75μ fused silica capillary to the API interface of API 100 spectrometer.

The remaining 1.48 mL/min is passed through the UV detector and to the ELS detector.

During the LC-analysis the detection data are acquired concurrently from the mass spectrometer, the UV detector and the ELS detector.

The LC conditions, detector settings and mass spectrometer settings used for the different methods are given in the following table.

| | |
|---|---|
| Column | YMC ODS-A 120 Å s - 5μ 3 mm × 50 mm id |
| Gradient | 5%-90% acetonitrile in 0.05% TFA linearly during 7.5 min at 1.5 mL/min |
| Detection | UV: 214 nm    ELS: 40° C. |
| MS | Experiment: Start: 100 amu Stop: 800 amu Step: 0.2 amu Dwell: 0.571 msec Method: Scan 284 times = 9.5 min |

HPLC-Preparative

Method D

The following instrumentation is used:
Gilson pump 306 (A and B)
Gilson detector UV/Vis-155
Gilson autosampler 215 Liquide Handler The HPLC pump is connected to two eluent reservoirs containing:
A: 0.1% TFA in water
B: 100% Acetonitrile The purification is performed at room temperature by injecting the sample solution on the column which is eluted with a gradient of solvent A and B.

The HPLC conditions, detector settings and mass spectrometer settings used are given in the following table.

| | |
|---|---|
| Column | Phenomenex Luna 10μ C18 (2) 100 Å, size 250 × 10 mm |
| Gradient | T = 0-3 min 0% B, t = 3-13 min linear from 0% to 100% B at 10 mL/min |
| Detection | UV: 214 and 254 nm |

HPLC-Preparative

Method E

The following instrumentation is used:
Gilson pump 306
Gilson detector UV/Vis-155
Gilson sampler; reodyne manuel injection
Gilson fraction collector-202
Gilson mixer-811C The HPLC pump is connected to two eluent reservoirs containing:
A: water
B: Acetonitrile The purification is performed at room temperature by injecting the sample solution on the column which is eluted with a gradient of solvent A and B.

The HPLC conditions, detector settings and mass spectrometer settings used are given in the following table.

| | |
|---|---|
| Column | Phenomenex, Synergi-MAX, 3μ, RP, size 250 × 30 mm |
| Gradient | 5-100% B, 40 min |
| Detection | UV: 210 |

LIST OF ABBREVIATIONS t-BuOK—Potassium tert-butoxide
DBU—1,8-Diazabicyclo[5.4.0]-undec-7-en
EDAC—1-(3-Dimethylaminopropyl)-3-ethyl-carbodiimide hydrochloride
DIC—1,3-Diisopropyl carbodiimide
DIPEA—Diisopropylethylamin
DCC—1,3-Dicyclohexyl carbodiimide
BOP—Benzotriazole-1-yl-oxy-tris-(dimethylamino) phosphoniumhexafluorophosphate
PyBroP—Bromotrispyrrolidinophosphonium hexafluorophosphate
HOBt—N-Hydroxybenzotriazole
HOAt—7-Aza-1-Hydroxybenzotriazole
DCM—Dichloromethane
NMP—N-Methylpyrrolidone
DMF—N,N-Dimethylformamide
TFA—Trifluoroacetic acid
TFFH—Fluoro-N,N,N',N'-tetramethylformamidinium hexafluorophosphate General Procedure (A)

General procedure (A) for the synthesis of compounds of the general formula (Ia):

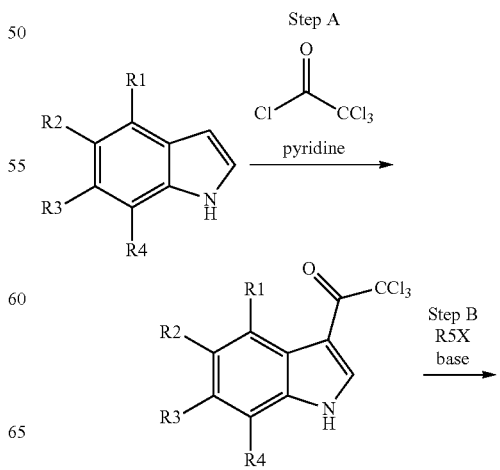

Step C:
To the solution from step B was added aqueous NaOH (0.10 mL, 4 N) and the reaction mixture was shaken for 1 hour whereupon aqueous HCl (0.60 mL, 1 N) was introduced. The aqueous phase was extracted with diethyl ether (2×1.5 mL), the two organic fractions were combined and the volatiles were removed in vacuo.

Step D:
The intermediate from step C was dissolved in NMP (0.20 mL) and HOBt (15 mg, 0.111 mmol), EDAC (37 mg, 0.192 mmol) and NH₂A (0.192 mmol) was added in sequence. The reaction mixture was heated to 120° C. for 2 hours before the reaction was allowed to cool to room temperature.

The resulting mixture was applied directly on a preparative HPLC instrument (HPLC-prep. (Method D)) and fractions were collected. The fractions containing the desired compound were combined and the volatiles were removed in vacuo.

General Procedure (B)
General procedure (B) for the synthesis of compounds of the general formula (Ia):

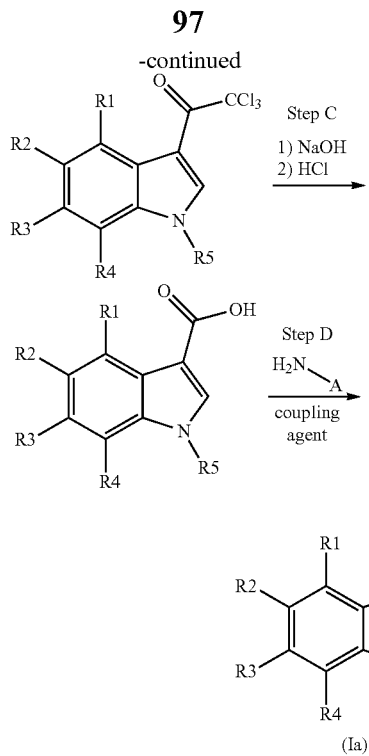

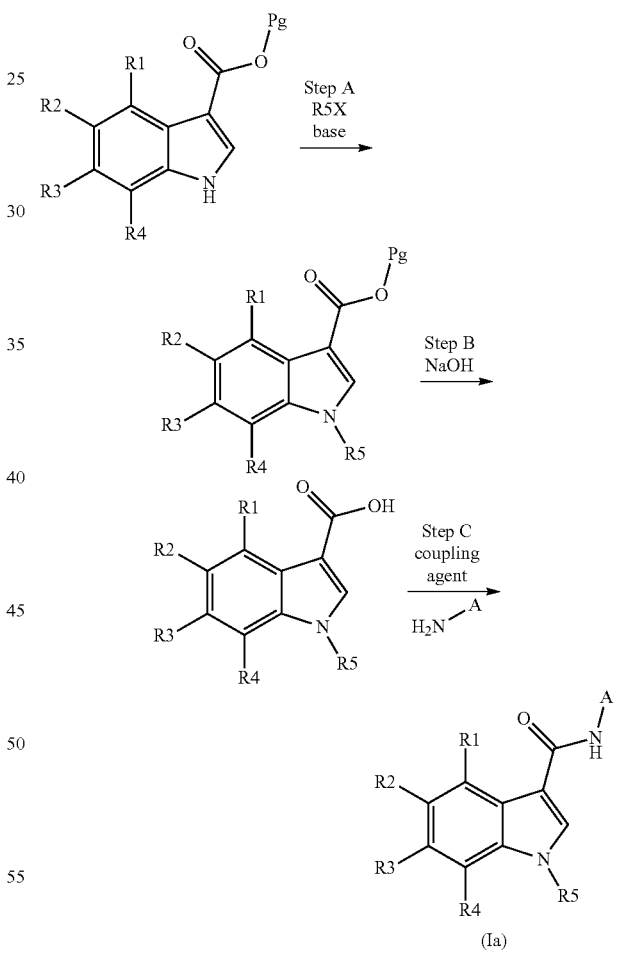

wherein R1, R2, R3, R4, R5 and A, are as defined for formula (I). The indole starting material can be either commercially available compounds or compounds that can be prepared following procedures described in the literature. In the general formula R5X, X represents chloride, bromide, iodide, mesylate or tosylate. The base used in step B can be NaH, K₂CO₃, NaOH, t-BuOK, DBU or an equivalent of these. The coupling agent in step D can be EDC, DIC, DCC, BOP, PyBroP or any equivalent of such which may be combined with HOBt or HOAt.

If a carboxylic acid is desired as a part of R1, R2, R3, R4, R5 or a substituent on A, a methylethyl-, isopropyl- or t-butyl ester can be taken through step A to step D and subsequently be hydrolysed using standard procedures for hydrolysis of esters. The procedure is illustrated in the following example.

Step A:
The indole derivative (20 mmol) was dissolved in DCM (15 mL) and pyridine (21 mmol) was added. The solution was cooled to 0° C. on an ice bath before a solution of trichloroacetyl chloride (20 mmol) in DCM (5 mL) was added over the course of 30 min. The cooling bath was removed and the reaction mixture was stirred at room temperature (typical over night). If HPLC showed unreacted indole starting material, an amount of trichloro acetyl chloride corresponding to the amount of unreacted indole (estimated by HPLC) was added, and the mixture was stirred for an additional 2 hours before the solvent was removed in vacuo. The crude product was stirred with ethanol-water (1:1, 15 mL) for 10 min before the product was filtered off and dried in vacuo at 50° C., and used without any further purification.

Step B:
To the 3-trichloroacetyl-indole derivative (0.096 mmol) from step A in NMP (0.20 mL) in a 5 mL glass vial, was added K₂CO₃ (20 mg, 0.144 mmol) and alkylating agent R5X (0.125 mmol) before the reaction mixture was shaken over night at room temperature.

wherein R1, R2, R3, R4, R5 and A, are as defined for formula (I), and Pg is a protecting group like methyl, ethyl, propyl, isopropyl, tert-butyl or benzyl. The indole starting material can be either commercially available compounds or compounds that can be prepared following procedures described in the literature. In the general formula R5X, X represents chloride, bromide, iodide, mesylate or tosylate. The base used in step A can be NaH, K₂CO₃, NaOH, t-BuOK, DBU or an equivalent of these. The coupling agent used in step C can be EDC, DIC, DCC, BOP, PyBroP or any equivalent of such which may or may not be combined with HOBt or HOAt.

The procedure is illustrated in the following example.

Step A:

The indole derivative (0.096 mmol) dissolved in NMP (0.10 mL) was added a solution of alkylating agent (R5X) (0.115 mmol) in NMP (0.20 mL) and subsequently solid $K_2CO_3$ (13.3 mg, 0.096 mmol). The reaction mixture was shaken at 40° C. for 24 hours.

Step B:

To the solution from step A was added aqueous NaOH (0.10 mL, 4 N) and the reaction mixture was shaken for two days whereupon aqueous HCl (0.60 mL, 1 N) was introduced. The aqueous phase was extracted with diethyl ether (2×1.5 mL), the two organic fractions were combined and the volatiles were removed in vacuo.

Step C:

The intermediate from step B was dissolved in NMP (0.20 mL) and HOBt (15 mg, 0.111 mmol), EDAC (37 mg, 0.192 mmol) and $NH_2A$ (19 mg, 0.192 mmol) was added in sequence. The reaction mixture was heated to 120° C. for 4 hours before the reaction was allowed to cool to room temperature.

The resulting mixture was applied directly on a preparative HPLC instrument (HPLC-prep. (Method D)) and fractions were collected. The fractions containing the desired compound were combined and the volatiles were removed in vacuo.

General Procedure (C)

General procedure (C) for the synthesis of compounds of the general formula (I):

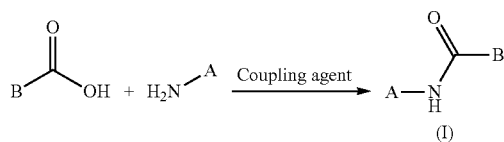

wherein B and A, are as defined for formula (I). The heteroarylcarboxylic acid starting material (BCOOH) and the aminoheterocycle ($NH_2A$) can be either a commercially available compound or compound that can be prepared following procedures described in the literature. The coupling agent used can be EDC, DIC, DCC, BOP, PyBroP, TFFH or any equivalent of such which may or may not be combined with HOBt or HOAt and the temperature may vary from 20° to 150° C.

The heteroarylcarboxylic acid (BCOOH) (0.096 mmol) was dissolved in NMP (0.20 mL) and HOBt (15 mg, 0.111 mmol), EDAC (37 mg, 0.192 mmol) and $NH_2A$ (19 mg, 0.192 mmol) was added in sequence. The reaction mixture was heated to 120° C. for 4 hours before the reaction was allowed to cool to room temperature.

The resulting mixture was applied directly on a preparative HPLC instrument (HPLC-prep. (Method D)) and fractions were collected. The fractions containing the desired compound were combined and the volatiles were removed in vacuo.

General Procedure D, E and F

General procedure (D, E and F) for the synthesis of compounds of the general formula (Ib):

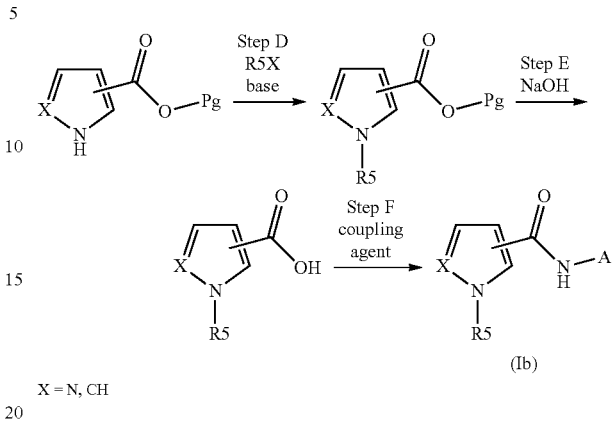

X = N, CH wherein (Ib) can be substituted with R1, R2 or R3 as defined for formula (I), and Pg is a protecting group like methyl, ethyl, propyl, isopropyl, tert-butyl or benzyl. The pyrrole or pyrazole starting material can be either commercially available compounds or compounds that can be prepared following procedures described in the literature. In general formula R5X, X represents chloride, bromide, iodide, mesylate or tosylate. The base used in step A can be NaH, $K_2CO_3$, NaOH, t-BuOK, DBU or an equivalent of these. The coupling agent used in step C can be EDC, DIC, DCC, BOP, PyBroP, TFFH or any equivalent of such which may or may not be combined with HOBt or HOAt.

General Procedure D:

Ethyl ester of a heteroaryl carboxylic acid (10.0 mmol) in DMF (20 mL) was added to a suspension of sodium hydride (600 mg, 15.0 mmol, 60% in oil) in DMF (20 mL) at 0° C. with stirring. After 30 min, an alkyl halide, such as an alkyl iodide or a benzylic bromide, was added. The ice bath was removed and the solution was stirred at room temperature overnight. The reaction mixture was carefully quenched with a small amount of water before adding ethyl acetate (100 ml) and water (50 mL). The layers were separated and the aqueous phase was extracted with ethyl acetate (2×100 mL). The combined organic extracts were washed with water (50 mL) and brine (50 mL). After drying over sodium sulfate, the solution was filtered and concentrated in vacuo to afford desired N-alkylated heteroaryl carboxylic acid ester.

General Procedure E:

The ester derivative (2 mmol) in a 1:1:1 mixture of THF/MeOH/2.5 M aqueous LiOH solution (10 mL) was stirred for 3 h. The reaction mixture was concentrated to half volume in vacuo. The residual aqueous solution was acidified with 1 N HCl to pH 5-6. The suspension was extracted with ethyl acetate (3×20 mL). The organic layer was washed (water and brine), dried (sodium sulfate), filtered and concentrated to afford desired N-alkylated heteroaryl carboxylic acid.

General Procedure F:

TFFH (0.25 mmol, 67 mg) was added to a DCM (3 mL) solution of the acid (0.25 mmol) and DIPEA (80 µL). After stirring for 15 min, 2-aminothiazole or its derivative was added. The mixture was stirred at room temperature for 16 h. After concentration, the residue was purified by flash chromatography (silica, 10-30% ethyl acetate in hexanes) to obtain desired amide.

General Procedure G and H

General procedure (G and H) for the synthesis of compounds of the general formula (Ic):

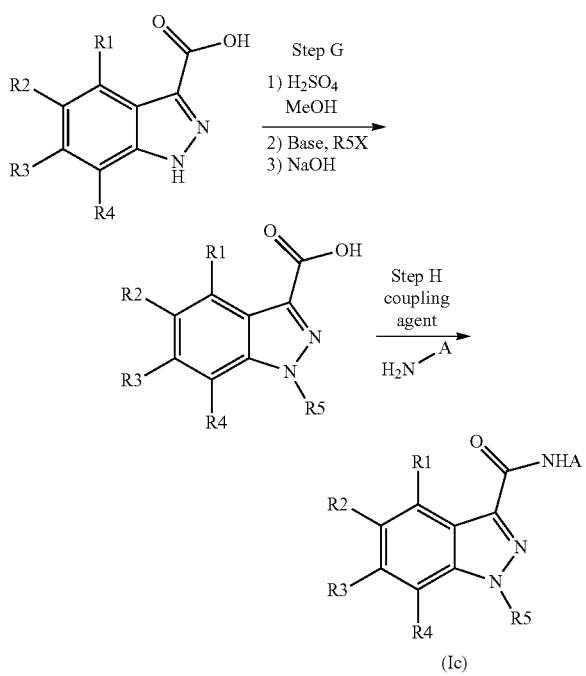

wherein R1, R2, R3, R4, R5 and A, are as defined for formula (I), The indazole starting material can be either commercially available compounds or compounds that can be prepared following procedures described in the literature. In the general formula R5X, X represents chloride, bromide, iodide, mesylate or tosylate. The base used in step A can be NaH, K$_2$CO$_3$, NaOH, t-BuOK, DBU or an equivalent of these. The coupling agent used in step C can be EDC, DIC, DCC, BOP, PyBroP or any equivalent of such which may or may not be combined with HOBt or HOAt.

General Procedure G.

Indazole-3-carboxylic acid (8.0 g, 50.0 mmol) was dissolved in anhydrous methanol (80 mL). After adding 2.0 mL of conc. H$_2$SO$_4$, the solution was heated at 50° C. for 24 h. The reaction mixture was slowly quenched by dropwise addition of saturated aqueous potassium carbonate. The solution was concentrated and the aqueous layer was extracted with ethyl acetate (3×100 mL). The combined organic extracts were washed with water (2×50 mL), dried over sodium sulfate, filtered and concentrated to afford a pale yellow solid (8.1 g). The solid was used without further purification.

Methyl indazole-3-carboxylate (0.5 g, 2.84 mmol) was dissolved in tert-BuOH (20 mL). Potassium tert-butoxide (0.32 g, 2.84 mmol) was added and the reaction mixture was stirred for 30 min at room temperature. An alkyl halide (2.84 mmol) was then added and the reaction mixture was heated at 70° C. for 72 h. The reaction mixture was cooled to room temperature and water was added. The aqueous phase was extracted with ethyl acetate (3×50 mL) and the combined organic extracts were washed (water and brine), dried (sodium sulfate), filtered and concentrated in vacuo to afford methyl 1-alkylindazole-3-carboxylate.

Methyl 1-alkylindazole-3-carboxylate was dissolved in MeOH and added aqueous NaOH (10 eq., 4 N) and the reaction mixture was stirred at 60° C. for 4 hours before aqueous HCl (11 eq., 1 N) was introduced. The aqueous phase was extracted with diethyl ether (2×1.5 mL), the organic fractions were combined and dried (MgSO$_4$) and the volatiles were removed in vacuo.

General Procedure H:

To the carboxylic acid (1 mmol) in DCE (8 mL) was added 1,1'-carbonyldiimidazole (1 mmol) and the mixture was heated at 50° C. After 1 h, an alkylamine, heteroarylamine or arylamine (1 mmol) was added and the reaction mixture was heated at 50° C. overnight. The crude reaction mixture was concentrated and purified by flash chromatography (silica, 30-50% ethyl acetate in hexanes) to afford the desired amide.

General Procedure (I)

General procedure (I) for the synthesis of compounds of the general formula (Ia):

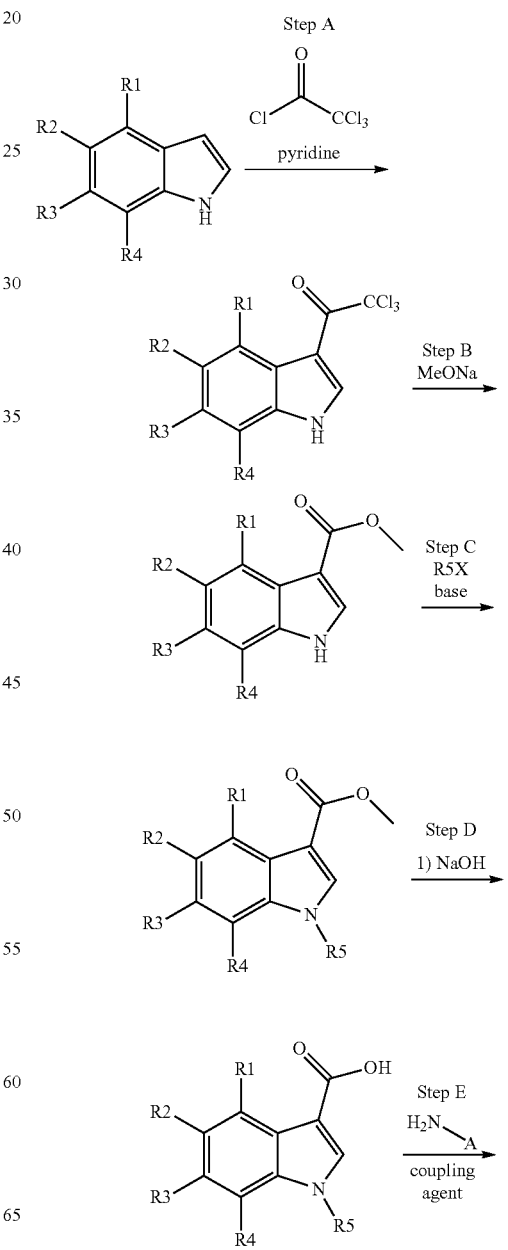

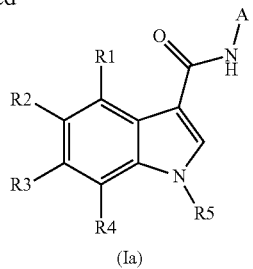

(Ia)

wherein R1, R2, R3, R4, R5 and A, are as defined for formula (I). The indole starting material can be either commercially available compounds or compounds that can be prepared following procedures described in the literature. In the general formula R5X, X represents chloride, bromide, iodide, mesylate or tosylate. The base used in step C can be NaH, K2CO3, NaOH, t-BuOK, DBU or an equivalent of these. The coupling agent in step E can be EDC, DIC, DCC, BOP, PyBroP or any equivalent of such which may be combined with HOBt or HOAt.

If a carboxylic acid is desired as a part of R1, R2, R3, R4, R5 or a substituent on A, a methylethyl-, isopropyl- or t-butyl ester can be taken through step A to step D and subsequently be hydrolysed using standard procedures for hydrolysis of esters. The procedure is illustrated in the following example.

Step A:

The indole derivative (44 mmol) was dissolved in DCM (25 mL) and pyridine (47 mmol) was added. A solution of trichloroacetyl chloride (66 mmol) in DCM (10 mL) was added over the course of 30 min. The reaction mixture was stirred at room temperature (typical over night). If HPLC showed unreacted indole starting material, an amount of trichloro acetyl chloride corresponding to the amount of unreacted indole (estimated by HPLC) was added, and the mixture was stirred for an additional 2 hours before the solvent was removed in vacuo. The crude product was stirred with ethanol-water (1:1, 40 mL) for 20 min before the product was filtered off and dried in vacuo at 40° C., and used without any further purification.

Step B:

To the 3-trichloroacetyl-indole derivative (18 mmol) from step A in methanol (50 mL) was added MeONa (2 eq) and the reaction mixture was stirred for 2 hour. The reaction mixture was concentrated in vacuo. The residue was dissolved in ethyl acetate and washed with a 10% solution of NaHSO4 (100 mL) followed by water (100 mL) and brine (100 mL). The organic phase was dried (MgSO4), filtered and concentrated in vacuo.

Step C:

To the 3-trichloroacetyl-indole derivative (5 mmol) from step B in THF (20 mL) was added NaH (60% in oil, 1.5 eq) and alkylating agent R5X (1.2 eq mmol). The reaction mixture was stirred over night at room temperature.

Step D:

To the solution from step C was added aqueous NaOH (4 eq, 1 N) and the reaction mixture was stirred at 80° C. The organic phase was evaporated in vacuo, and the residue purified by preparative HPLC (Method E). The fractions containing the desired compound were combined and the volatiles were removed in vacuo.

Step E:

The intermediate from step D (0.5 mmol) was dissolved in dry NMP (2.0 mL) and HOBt (90 mg, 0.66 mmol), EDAC (128 mg, 0.66 mmol) and DIPEA (127 mg, 0.666 mmol) was added and the reaction mixture heated to 40° C. under stirring for 30 min. NH2A (0.66 mmol) was added and the reaction mixture was heated to 120° C. for 1 hour and over night at room temperature.

The resulting mixture was applied directly on a preparative HPLC instrument (HPLC-prep. (Method E)) and fractions were collected. The fractions containing the desired compound were combined and the volatiles were removed in vacuo.

General Procedure (J)

General procedure (J) for the synthesis of compounds of the general formula (Ia):

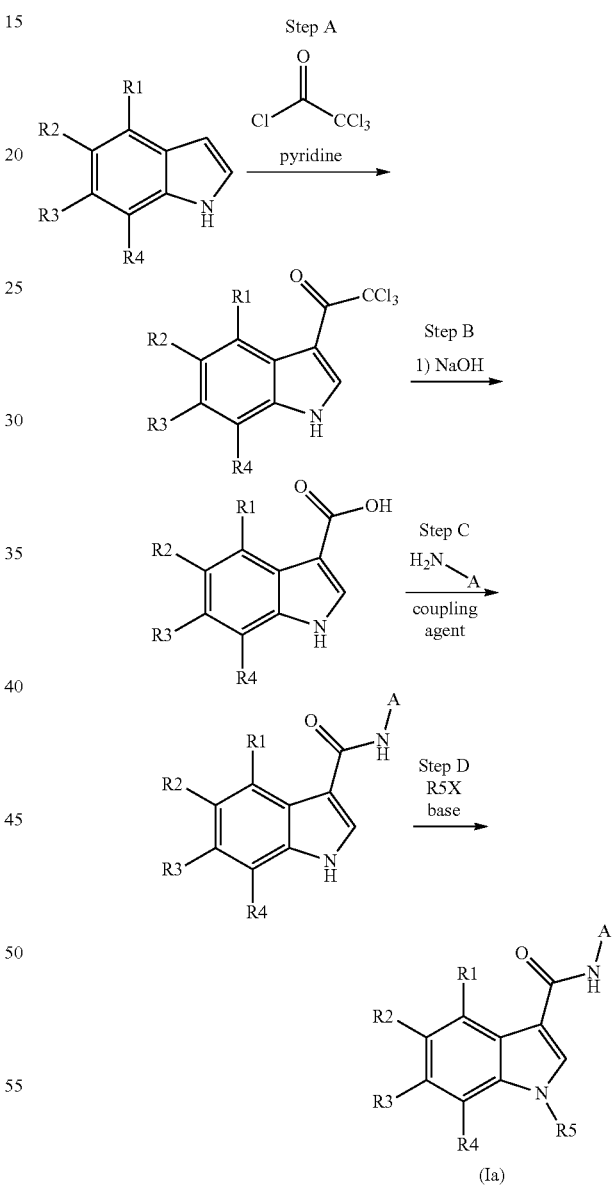

(Ia)

wherein R1, R2, R3, R4, R5 and A, are as defined for formula (I). The indole starting material can be either commercially available compounds or compounds that can be prepared following procedures described in the literature. In the general formula R5X, X represents chloride, bromide, iodide, mesylate or tosylate. The coupling agent in step C can be EDC, DIC, DCC, BOP, PyBroP or any equivalent of such which may be combined with HOBt or HOAt. The base used in step D can be NaH, K2CO3, NaOH, t-BuOK, DBU or an equivalent of these.

If a carboxylic acid is desired as a part of R1, R2, R3, R4, R5 or a substituent on A, a methylethyl-, isopropyl- or t-butyl ester can be taken through step A to step D and subsequently be hydrolysed using standard procedures for hydrolysis of esters. The procedure is illustrated in the following example.

Step A:

The indole derivative (44 mmol) was dissolved in DCM (25 mL) and pyridine (47 mmol) was added. A solution of trichloroacetyl chloride (66 mmol) in DCM (10 mL) was added over the course of 30 min. The reaction mixture was stirred at room temperature (typical over night). If HPLC showed unreacted indole starting material, an amount of trichloro acetyl chloride corresponding to the amount of unreacted indole (estimated by HPLC) was added, and the mixture was stirred for an additional 2 hours before the solvent was removed in vacuo. The crude product was stirred with ethanol-water (1:1, 40 mL) for 20 min before the product was filtered off and dried in vacuo at 40° C., and used without any further purification.

Step B:

To the 3-trichloroacetyl-indole derivative (25 mmol) from step A in THF (200 mL) was added NaOH (1N, 100 mL), and the reaction mixture was stirred at room temperature for 16 h. The reaction mixture was concentrated in vacuo to half the volume, and added 1 N HCl. The product was isolated by filtration and washed with water.

Step C:

The intermediate from step B (5 mmol) was dissolved in dry NMP (20 mL) and HOBt (770 mg, 5.7 mmol), EDAC (1.1 g, 5.7 mmol) and DIPEA (735 mg, 5.7 mmol) was added. The reaction mixture was heated under stirring at 40° C. for 30 min. NH2A (9.5 mmol) was added and the reaction mixture was heated to 120° C. for 2 hour. The resulting mixture was either poured on water and the product isolated by filtration or applied directly on a preparative HPLC instrument (HPLC-prep. (Method E)).

Step D:

The intermediate from step C (0.2 mmol) in THF (2 mL) was added NaH (60% in oil, 2 eq) followed by a mixture of the alkylating agent R5X (1 eq) and NaH (60% in oil, 1 eq) in DMSO (0.1 mL). The reaction mixture was stirred over night at room temperature. The resulting mixture was added water (0.5 mL) and applied directly on a preparative HPLC instrument (HPLC-prep. (Method E)).

General Procedure (K)

General procedure (K) for the synthesis of compounds of the general formula (Ia):

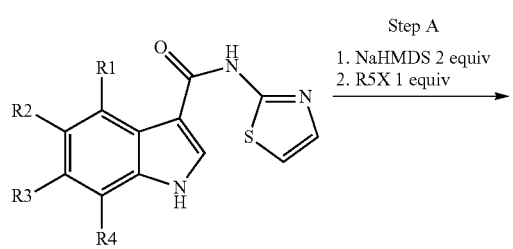

Step A
1. NaHMDS 2 equiv
2. R5X 1 equiv

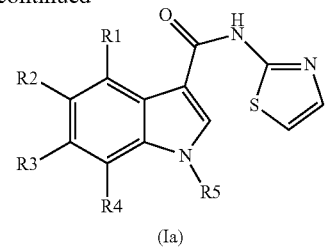

(Ia)

wherein R1, R2, R3, R4, R5 and A, are as defined for formula (I). The indole starting material was prepared using general procedure (J) Step A to C. In the general formula R5X, X represents chloride, bromide, iodide, mesylate or tosylate. The procedure is illustrated in the following example.

Step A:

The indole prepared as described in general procedure (J) step A to C (1 mmol) was suspended in dry in THF (4 mL) and cooled to 0° C. NaHMDS (2.2 mmol, 1M in THF) was added and the mixture was stirred for 1 h at room temperature. Then the appropriate alkyl halide/tosylate R5X (1.1 mmol) was added and the mixture was stirred at room temperature over night. Addition of MeOH (5 mL) and 2M aqueous LiOH (2 mL) followed by stirring for 4 h. The mixture was evaporated to ¼ of the volume and acidified with 1N HCl. If the product precipitated it was collected by filtration and washed with water otherwise the mixture was extracted with EtOAc. The organic phase was dried and concentrated in vacuo and purified by preparative HPLC (HPLC-prep. (Method E)).

Example 1

1-Cyclopentyl-1H-indole-3-carboxylic acid thiazol-2-ylamide

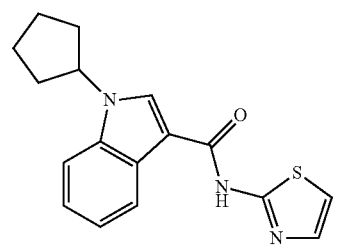

Methyl indole-3-carboxylate (1 g, 5.7 mmol) was dissolved in dry NMP (5 mL) under nitrogen, Bromocyclopentane (11.4 mmol) was added followed by NaH (60%) (274 mg, 11.4 mmol). The mixture was heated to 70° C. for 2 hours. After cooling to room temperature the reaction mixture was quenched with acetic acid (1 mL). and the mixture was separated between diethyl ether (50 mL) and water (50 mL). The organic phase was isolated, dried ($Na_2SO_4$) and solvent removed in vacuo.

The crude material was dissolved in ethanol (10 mL) and NaOH (400 mg, 10 mmol) dissolved in water (2 mL) was added and the mixture was heated to reflux for 3 hours. After cooling to room temperature, water (50 mL) was added and the pH adjusted to pH=2 by the addition of 1N HCl. The mixture was washed with diethyl ether (2×50 mL). The organic phase was isolated, dried ($Na_2SO_4$) and solvent removed in vacuo. To give the crude derivative of indole-3-carboxylic acid that was subsequently used in the next step without any further purification.

The crude derivative of indole-3-carboxylic acid was dissolved in NMP (5 mL). EDAC (1.09 g, 5.7 mmol) and HOBt (0.92 g, 6.84 mmol) were added. The mixture was stirred at room temperature for 1 hour before 2-aminothiazole (5.7 mmol) was added. The mixture was heated to 120° C. for 2 hours. After cooling to room temperature the reaction mixture was separated between diethyl ether (50 mL) and water (50 mL). The organic phase was washed with saturated aqueous $Na_2CO_3$ (50 mL), dried ($Na_2SO_4$) and the solvent removed in vacuo. The crude material was recrystallized from acetonitrile to give the title compound.

HPLC-MS (Method A): m/z=230 (M+1); $R_t$=3.36 min.

Example 2

Prepared in Accordance with the Procedure Described in Example 1

1-CycloHexylmethyl-1H-indole-3-carboxylic acid thiazol-2-ylamide

R5Br=Cyclohexylmethylbromide; $NH_2A$=2-aminothiazole; Indole starting material=methyl indole 3-carboxylate

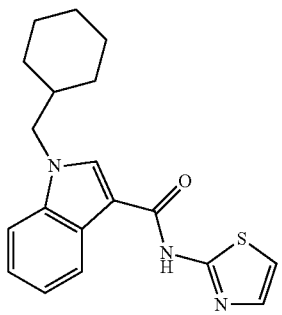

$^1$H NMR (DMSO-$d_6$): δ12.12 (s, 1H), 8.55 (s, 1H), 8.25 (d, 1H), 7.61 (d, 1H), 7.51 (d, 1H); 7.30-7.20 (m, 2H), 7.18 (d, 1H), 4.10 (d, 2H), 1.83 (m, 1H), 1.75-1.55 (m, 5H), 1.36-0.93 (m, 5H).

Example 3

General Procedure (B)

1-Benzyl-1H-indole-3-carboxylic acid thiazol-2-ylamide

R5Br=Bromomethylbenzene; $NH_2A$=2-aminothiazole; Indole starting material=methyl indole 3-carboxylate

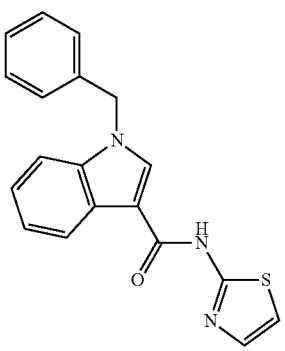

HPLC-MS (Method A): m/z=334 (M+1); $R_t$=3.90 min.

Example 4

General Procedure (B)

1-Benzyl-1H-indole-3-carboxylic acid pyridine-2-ylamide

R5Br=Bromomethylbenzene; $NH_2A$=2-aminopyridine; Indole starting material=methyl indole 3-carboxylate

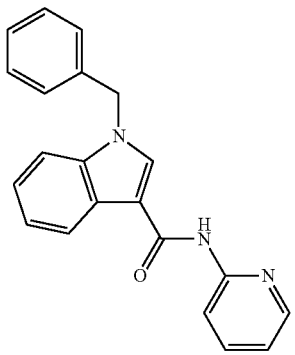

HPLC-MS (Method B): m/z=328 (M+1); $R_t$=2.66 min.

Example 5

General Procedure (B)

2-[(1-Benzyl-1-indole-3-carbonyl)-amino]-thiazol-4-yl}-acetic acid

R5X=bromomethylbenzene; $NH_2A$=ethyl-2-(2-amino-1,3-thiazol-4-yl)acetate; Indole starting material=methyl indole 3-carboxylate

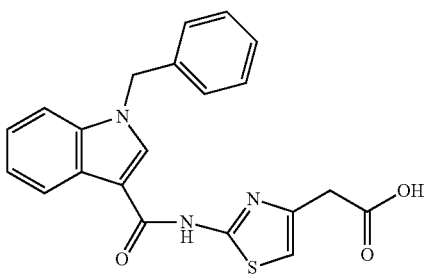

Ethyl 2-[(1-benzyl-1-indole-3-carbonyl)-amino]-thiazol-4-yl}-acetate obtained after step C was dissolved in EtOH (1.0 mL) and NaOH (256 μL, 4 N in water) was introduced. The reaction mixture was stirred 30 min at room temperature before HCl (1.3 mL, 1N in water) was added whereupon a precipitate was formed. The solid material was filtered off, washed with water (5 mL) and dried in vacuo at 50° C. for 16 hours.

HPLC-MS (Method A): m/z=414 (M+23); $R_t$=3.8 min.

Example 6

General Procedure (A)

1-(3-Fluoro-benzyl)-6-fluoro-1H-indole-3-carboxylic acid thiazol-2-ylamide

Indole starting material=6-fluoroindole; R5X=3-fluoro-bromomethylbenzene; NH₂A=2-aminothiazole

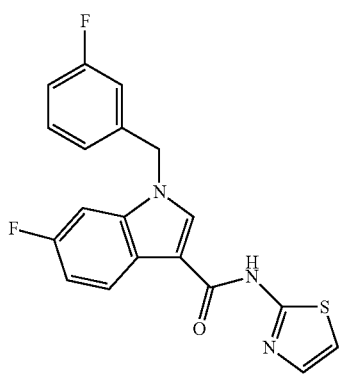

HPLC-MS (Method C): m/z=370 (M+1); $R_t$=4.60 min.

Example 7

General Procedure (A)

1-(2-Fluoro-benzyl)-6-fluoro-1H-indole-3-carboxylic acid thiazol-2-ylamide

Indole starting material=6-fluoroindole; R5X=2-fluoro-bromomethylbenzene, NH₂A=2-aminothiazole

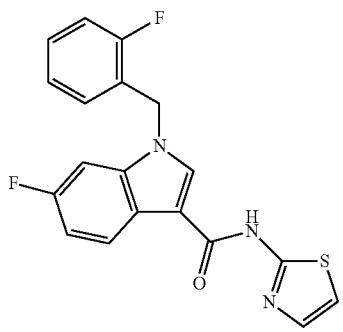

HPLC-MS (Method C): m/z=370 (M+1); $R_t$=4.60 min.

Example 8

General Procedure (A)

1-(4-Trifluoromethyl-benzyl)-6-fluoro-1H-indole-3-carboxylic acid thiazol-2-ylamide Indole starting material=6-fluoroindole; R5X=4-trifluoromethyl-bromomethylbenzene; NH₂A=2-aminothiazole

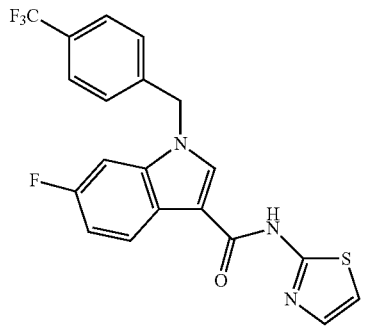

HPLC-MS (Method C): m/z=420 (M+1); $R_t$=5.10 min.

Example 9

General Procedure (A)

6-Fluoro-1-(4-methanesulfonyl-benzyl)-1H-indole-3-carboxylic acid thiazol-2-ylamide Indole starting material=6-fluoroindole; R5X=4-methylsulfonyl benzylchloride; NH₂A=2-aminothiazole

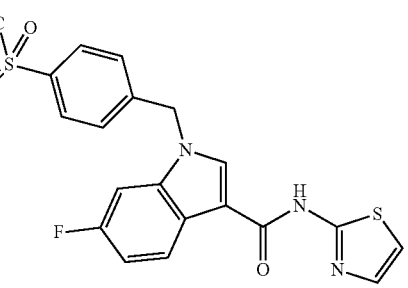

HPLC-MS (Method C): m/z=430 (M+1); $R_t$=3.9 min.

Example 10

General Procedure (A)

5-Methyl-1-(benzyl)-1H-indole-3-carboxylic acid thiazol-2-ylamide

Indole starting material=5-methyl-indole; R5X=1-bromomethylbenzene; NH₂A=2-aminothiazole

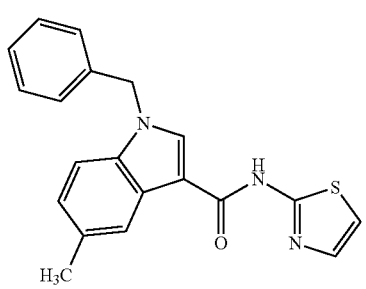

HPLC-MS (Method C): m/z=348 (M+1); $R_t$=4.7 min.

Example 11

General Procedure (A)

1-(Phenylethyl)-1H-indole-3-carboxylic acid thiazol-2-ylamide

Indole starting material=Indole; R5X=2-bromoethylbenzene; NH$_2$A=2-aminothiazole

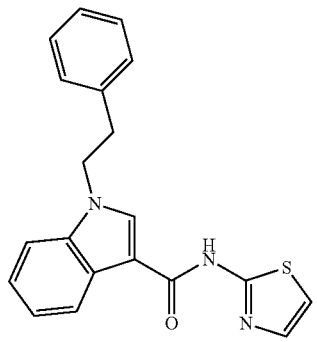

HPLC-MS (Method C): m/z=348 (M+1); R$_t$=4.5 min.

Example 12

General Procedure (A)

1-Cyanomethyl-1H-indole-3-carboxylic acid thiazol-2-ylamide

Indole starting material=indole; R5X=bromoacetonitrile, NH$_2$A=2-aminothiazole

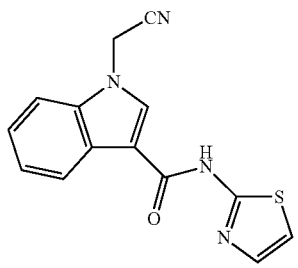

HPLC-MS (Method C): m/z=283 (M+1); R$_t$=3.20 min.

Example 13

1-Benzyl-6-(morpholine-4-carbonyl)-1H-indole-3-carboxylic acid thiazol-2-ylamide Indole-6-carboxylic acid (0.60 g, 3.7 mmol) was dissolved in DCM (15 mL) and carbonyl diimidazole (0.63 g, 3.9 mmol) was added and the reaction mixture was refluxed under N$_2$ for 30 min. The mixture was allowed to cool to room temperature before morpholine (0.39 g, 4.5 mmol) was added and the reaction mixture was refluxed for 16 hours. The mixture was allowed to cool to room temperature before it was washed in sequence with HCl (50 mL, 1 N in water), NaOH (50 mL, 1 N in water) and brine (50 mL). The organic phase was dried with MgSO$_4$, and the solvent was removed in vacuo to give 0.74 g of (1H-indol-6-yl)-morpholin-4-yl-methanone.

This compound was transformed to the title compound according to General procedure (A), using R5X=bromomethylbenzene; NH$_2$A=2-aminothiazole.

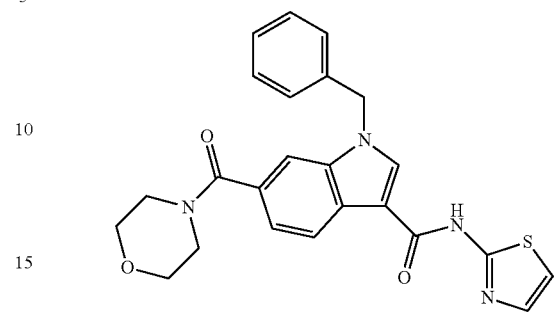

HPLC-MS (Method C): m/z=477 (M+1); R$_t$=3.40 min.

Example 14

1-Methyl-1H-indole-3-carboxylic acid thiazol-2-ylamide

1-Methyl-1H-indole-3-carboxylic acid and 2-aminothiazole was coupled and purified according to the conditions described in General Procedure (B), Step C).

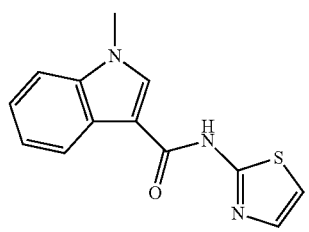

HPLC-MS (Method B): m/z=258 (M+1); R$_t$=3.16 min.

Example 15

General Procedure (A)

1-Cyclopropylmethyl-6-fluoro-1H-indole-3-carboxylic acid thiazol-2-ylamide

Indole starting material=6-fluoroindole; R5X=Cyclopropylmethylbromide; NH$_2$A=2-aminothiazole

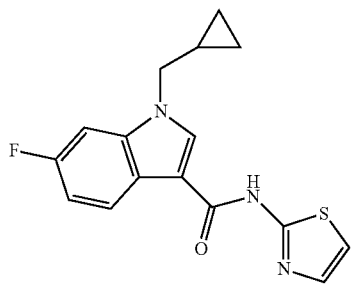

HPLC-MS (Method B): m/z=316 (M+1); R$_t$=4.06 min.

Example 16

General Procedure (B)

6-Fluoro-1-prop-2-ynyl-1H-indole-3-carboxylic acid thiazol-2-ylamide

Indole starting material=6-fluoroindole; R5X=propargylbromide; NH₂A=2-aminothiazole

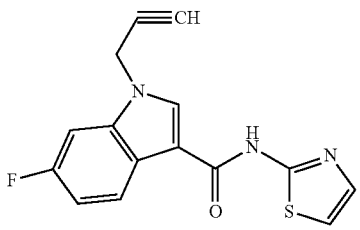

HPLC-MS (Method B): m/z=300 (M+1); $R_t$=4.0 min.

Example 17

General Procedure (A)

1-But-2-enyl-6-fluoro-1H-indole-3-carboxylic acid thiazol-2-ylamide

Indole starting material=6-fluoroindole; R5X=crotylbromide; NH₂A=2-aminothiazole

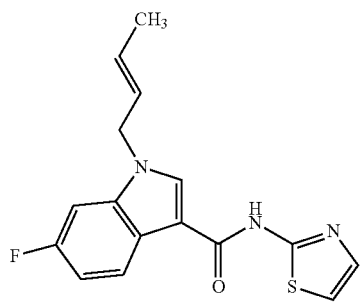

HPLC-MS (Method B): m/z=316 (M+1); $R_t$=4.6 min.

Example 18

General Procedure (A)

6-Fluoro-1-(3-methyl-but-2-enyl)-1H-indole-3-carboxylic acid thiazol-2-ylamide

Indole starting material=6-fluoroindole; R5X=3,3-dimethylallylbromide; NH₂A=2-aminothiazole

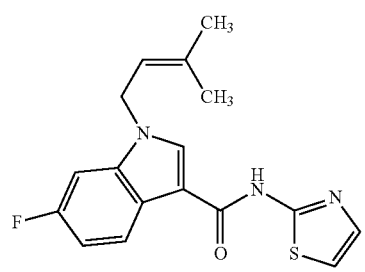

HPLC-MS (Method B): m/z=330 (M+1); $R_t$=4.8 min.

Example 19

General Procedure (A)

1-Cyclopropylmethyl-6-fluoro-1H-indole-3-carboxylic acid [1,2,4]thiadiazol-5-ylamide Indole starting material=6-fluoroindole; R5X=bromomethylcyclopropane; NH₂A=[1,2,4]-thiadiazole-5-ylamine

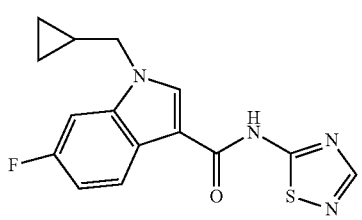

HPLC-MS (Method A): m/z=317 (M+1); $R_t$=3.9 min.

Example 20

General Procedure (A)

6-Bromo-1-cyclopropylmethyl-1H-indole-3-carboxylic acid thiazol-2-ylamide

Indole starting material=6-bromoindole; R5X=bromomethylcyclopropane; NH₂A=2-aminothiazole

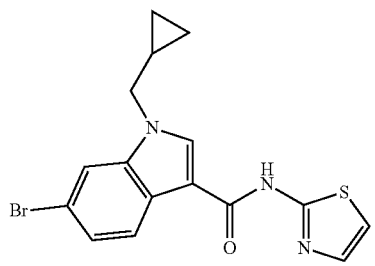

HPLC-MS (Method A): m/z=378 (M+1); $R_t$=4.31 min.

Example 21

General procedure (A)

6-Chloro-1-cyclopropylmethyl-1H-indole-3-carboxylic acid thiazol-2-ylamide

Indole starting material=6-chloroindole; R5X=bromomethylcyclopropane; NH₂A=2-aminothiazole

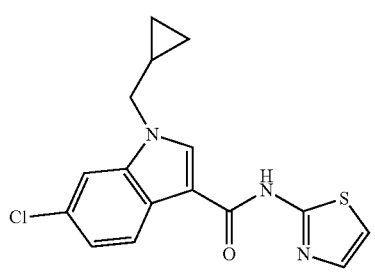

HPLC-MS (Method A): m/z=332 (M+1); $R_t$=4.2 min.

Example 22

General procedure (A)

1-Cyclopropylmethyl-6-methoxy-1H-indole-3-carboxylic acid thiazol-2-ylamide

Indole starting material=6-methoxyindole; R5X=bromomethylcyclopropane; NH$_2$A=2-aminothiazole

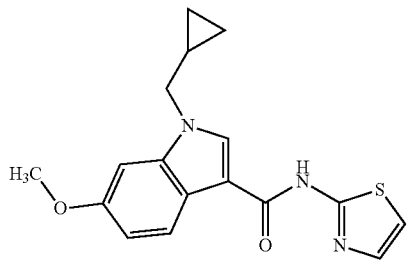

HPLC-MS (Method A): m/z=328 (M+1); R$_t$=3.6 min.

Example 23

General Procedure (A)

1-Cyclopropylmethyl-6-methyl-1H-indole-3-carboxylic acid thiazol-2-ylamide

Indole starting material=6-methylindole; R5X=bromomethylcyclopropane; NH$_2$A=2-aminothiazole

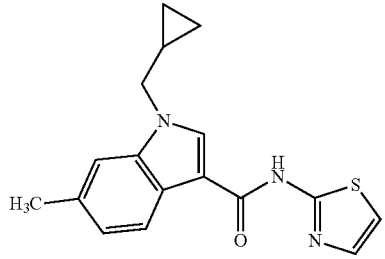

HPLC-MS (Method A): m/z=312 (M+1); R$_t$=3.9 min.

Example 24

General Procedure (A)

1-Cyclopropylmethyl-6-trifluoromethyl-1H-indole-3-carboxylic acid thiazol-2-ylamide
Indole starting material=6-trifluoromethylindole; R5X=bromomethylcyclopropane; NH$_2$A=2-aminothiazole

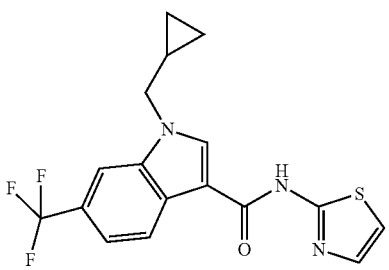

HPLC-MS (Method A): m/z=366 (M+1); R$_t$=4.4 min.

Example 25

General procedure (A)

1-Cyclopropylmethyl-6-nitro-1H-indole-3-carboxylic acid thiazol-2-ylamide

Indole starting material=6-nitroindole; R5X=bromomethylcyclopropane; NH$_2$A=2-aminothiazole

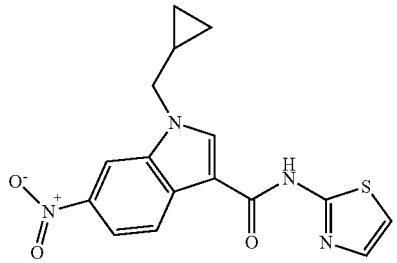

HPLC-MS (Method A): m/z=343 (M+1); R$_t$=4.0 min.

Example 26

General Procedure (B)

1-(3-Fluoro-benzyl)-1H-indole-3-carboxylic acid thiazol-2-ylamide

R5X=1-Bromomethyl-3-fluoro-benzene; NH$_2$A=2-aminothiazole; Indole starting material=methyl indole 3-carboxylate

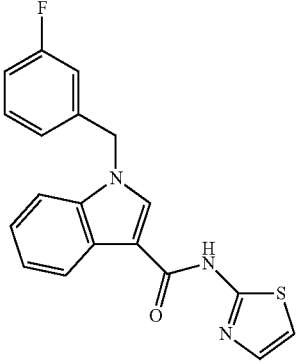

HPLC-MS (Method A): m/z=352 (M+1); R$_t$=4.04 min.

Example 27

General procedure (B)

1-(2-Trifluoro-benzyl)-1H-indole-3-carboxylic acid thiazol-2-ylamide

R5X=1-Bromomethyl-2-trifluoromethyl-benzene; NH$_2$A=2-aminothiazole; Indole starting material=methyl indole 3-carboxylate

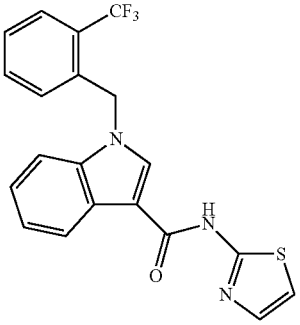

HPLC-MS (Method A): m/z=402 (M+1); R$_t$=4.47 min.

Example 28

General Procedure (B)

1-(2-Fluoro-benzyl)-1H-indole-3-carboxylic acid thiazol-2-ylamide

R5X=1-Bromomethyl-2-fluoro-benzene, NH$_2$A=2-aminothiazole; Indole starting material=methyl indole 3-carboxylate

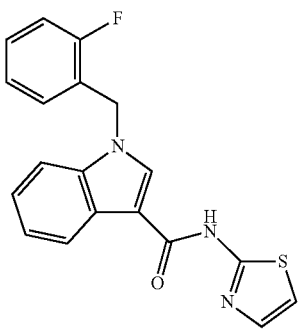

HPLC-MS (Method A): m/z=352 (M+1); R$_t$=4.03 min.

Example 29

General Procedure (B)

1-(4-Methanesulfonyl-benzyl)-1H-indole-3-carboxylic acid thiazol-2-ylamide

R5X=1-Bromomethyl-4-methanesulfonyl-benzene, NH$_2$A=2-aminothiazole; Indole starting material=methyl indole 3-carboxylate

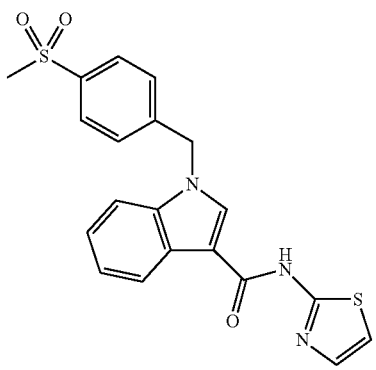

HPLC-MS (Method C): m/z=412 (M+1); R$_t$=3.39 min.

Example 30

General Procedure (B)

1-(3-Trifluoro-benzyl)-1H-indole-3-carboxylic acid thiazol-2-ylamide

R5X=1-Bromomethyl-3-trifluoromethyl-benzene; NH$_2$A=2-aminothiazole; Indole starting material=methyl indole 3-carboxylate

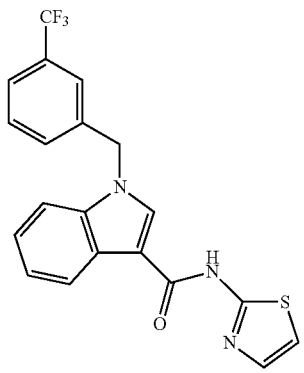

HPLC-MS (Method C): m/z=402 (M+1); R$_t$=4.39 min.

Example 31

General Procedure (B)

1-(3-Chloro-benzyl)-1H-indole-3-carboxylic acid thiazol-2-ylamide

R5X=1-Bromomethyl-3-chloro-benzene; NH$_2$A=2-aminothiazole; Indole starting material=methyl indole 3-carboxylate

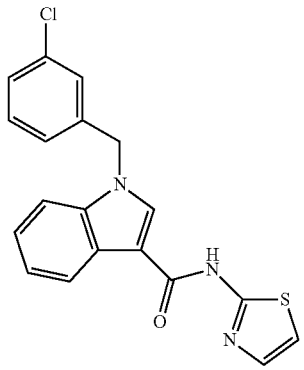

HPLC-MS (Method A): m/z=368 (M+1); R$_t$=4.27 min.

Example 32

General Procedure (B)

1-(4-Fluoro-benzyl)-1H-indole-3-carboxylic acid thiazol-2-ylamide

R5X=1-Bromomethyl-4-fluoro-benzene; NH$_2$A=2-aminothiazole; Indole starting material=methyl indole 3-carboxylate

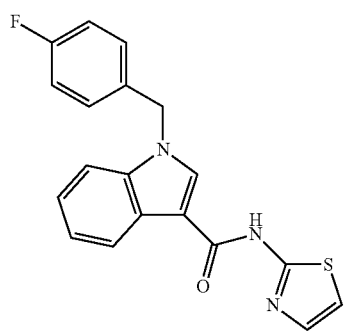

HPLC-MS (Method A): m/z=352 (M+1); $R_t$=4.05 min.

Example 33

General Procedure (B)

1-(3-Methoxy-benzyl)-1H-indole-3-carboxylic acid thiazol-2-ylamide

R5X=1-Bromomethyl-3-methoxy-benzene; NH$_2$A=2-aminothiazole; Indole starting material=methyl indole 3-carboxylate

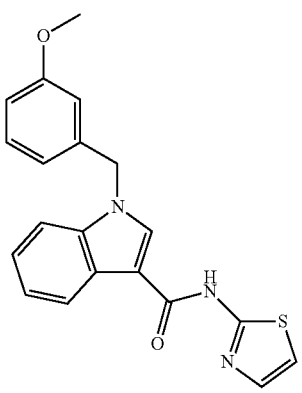

HPLC-MS (Method A): m/z=364 (M+1); $R_t$=4.00 min.

Example 34

General Procedure C 1-(4-Acetylamino-benzyl)-1H-indole-3-carboxylic acid thiazol-2-ylamide R5X=N-(4-chloromethylphenyl)-acetamide; NH$_2$A=2-aminothiazole; Indole starting material=methyl indole 3-carboxylate

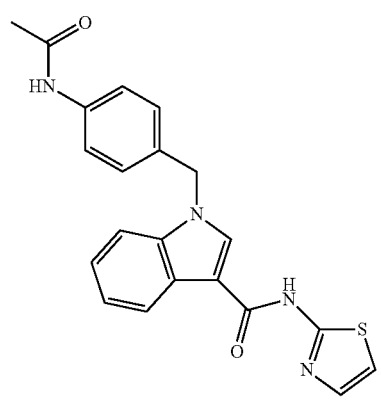

HPLC-MS (Method A): m/z=391 (M+1); $R_t$=3.27 min.

Example 35

General Procedure (B)

1-Phenylcarbamoylmethyl-1H-indole-3-carboxylic acid thiazol-2-ylamide

R5X=2-chloro-N-phenylacetamide; NH$_2$A=2-aminothiazole; Indole starting material=methyl indole 3-carboxylate

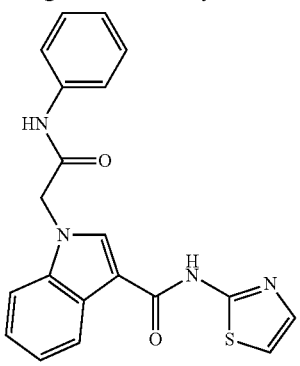

HPLC-MS (Method A): m/z=377 (M+1); $R_t$=3.5 min.

Example 36

General Procedure (A)

1-Benzyl-5-fluoro-1H-indole-3-carboxylic acid thiazol-2-ylamide

Indole starting material=5-fluoroindole; R5X=Bromomethylbenzene; NH$_2$A=2-aminothiazole

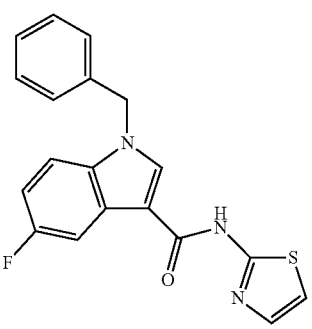

HPLC-MS (Method A): m/z=352 (M+1); R=4.14 min.

Example 37

General Procedure (A)

1-Benzyl-5-chloro-1H-indole-3-carboxylic acid thiazol-2-ylamide

Indole starting material=5-chloroindole; R5X=bromomethylbenzene; NH$_2$A=2-aminothiazole

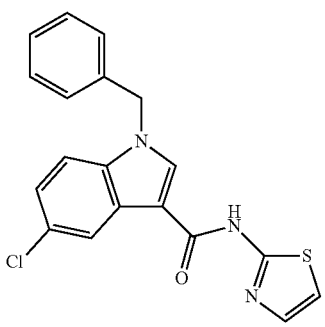

HPLC-MS (Method B): m/z=368 (M+1); R$_t$=4.46 min.

Example 38

General Procedure (A)

1-Benzyl-5-benzyloxy-1H-indole-3-carboxylic acid thiazol-2-ylamide

Indole starting material=5-benzyloxyindole; R5X=bromomethylbenzene; NH$_2$A=2-aminothiazole

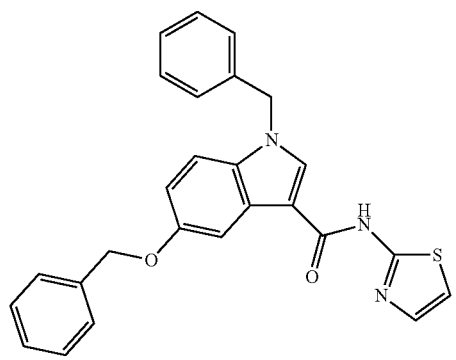

HPLC-MS (Method B): m/z=440 (M+1); R$_t$=4.72 min.

Example 39

General Procedure (A)

1-Benzyl-5-methyl-1H-indole-3-carboxylic acid thiazol-2-ylamide

Indole starting material=5-methylindole; R5X=bromomethylbenzene; NH$_2$A=2-aminothiazole

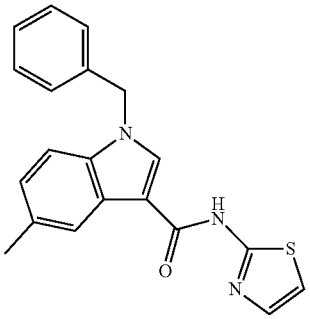

HPLC-MS (Method A): m/z=348 (M+1); R$_t$=4.24 min.

Example 40

General Procedure (A)

1-Benzyl-4-methoxy-1H-indole-3-carboxylic acid thiazol-2-ylamide

Indole starting material=4-methoxyindole; R5X=Bromomethylbenzene, NH$_2$A=2-aminothiazole

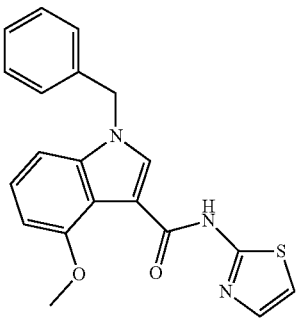

HPLC-MS (Method A): m/z=364 (M+1); R$_t$=3.92 min.

Example 41

General Procedure (A)

5-Benzyl-5H-[1,3]-dioxolo[4,5-f]indole-7-carboxylic acid thiazol-2-ylamide

Indole starting material=5,6-methylenedioxyindole; R5X=bromomethylbenzene, NH$_2$A=2-aminothiazole

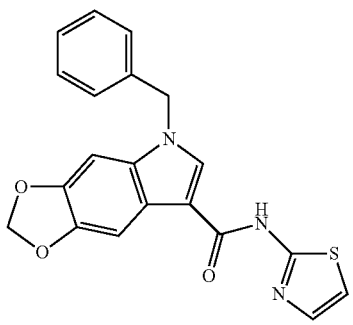

HPLC-MS (Method B): m/z=378 (M+1); R$_t$=3.90 min.

Example 42

General Procedure (A)

1-Benzyl-6-fluoro-1H-indole-3-carboxylic acid thiazol-2-ylamide

Indole starting material=6-fluoroindole; R5X=bromomethylbenzene; NH$_2$A=2-aminothiazole

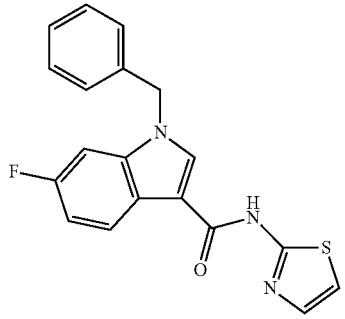

HPLC-MS (Method A): m/z=352 (M+1); R$_t$=4.16 min.

Example 43

General Procedure (B)

1-Carbamoylmethyl-1H-indole-3-carboxylic acid thiazol-2-ylamide

Indole starting material=indole; R5X=2-bromo-acetamide; NH$_2$A=2-aminothiazole

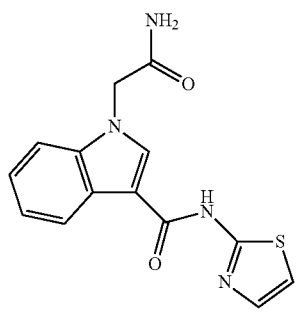

HPLC-MS (Method C): m/z=301 (M+1); R$_t$=2.40 min.

Example 44

General Procedure (B)

1-(2-Methyl-allyl)-1H-indole-3-carboxylic acid thiazol-2-ylamide

Indole starting material=indole; R5X=3-bromo-2-methyl-propene; NH$_2$A=2-aminothiazole

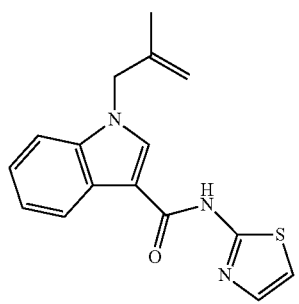

HPLC-MS (Method C): m/z=298 (M+1); R$_t$=4.00 min.

Example 45

General Procedure (A)

1-Cyclopropyl-methyl-1H-indole-3-carboxylic acid thiazol-2-ylamide

Indole starting material=indole; R5X=cyclopropyl-methylbromide; NH$_2$A=2-aminothiazole

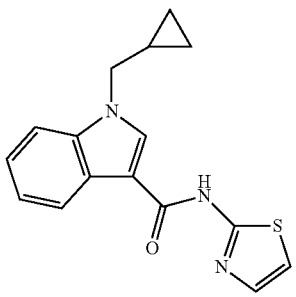

HPLC-MS (Method C): m/z=298 (M+1); R$_t$=4.00 min.

Example 46

General Procedure (B)

1-Benzyl-1H-indole-3-carboxylic acid pyrimidin-4-ylamide

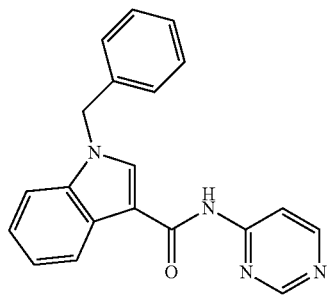

1-Benzylindole-3-carboxylic acid (25.9 mg, 96 mmol) was dissolved in SOCl$_2$ (1 mL) and the mixture was stirred for 30 min before the volatiles were removed in vacuo. The residue was dissolved in MeCN (200 µL) and added to a solution of pyrimidin-4-yl-amine (10 mg, 105 mmol) in NMP (200 µL). The reaction mixture was stirred 16 hours at room temperature before the MeCN was removed in vacuo. The residue was purified using HPLC method D to give title compound. HPLC-MS (Method A): m/z=329 (M+1); R$_t$=3.3 min.

Example 47

General Procedure (A)

1-(4-Carbamoyl-benzyl)-6-fluoro-1H-indole-3-carboxylic acid thiazol-2-ylamide

Indole starting material=6-fluoroindole; R5X=4-chlormethylbenzamide; NH$_2$A=2-aminothiazole

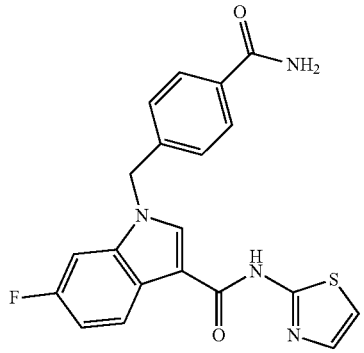

HPLC-MS (Method A): m/z=395 (M+1); R$_t$=3.1 min.

Example 48

General procedure (B)

1-Cyclopropylmethyl-1H-pyrrolo[2,3-b]pyridine-3-carboxylic acid thiazol-2-ylamide Azaindole starting material=1H-pyrrolo[2,3-b]pyridine-3-carboxylic acid methyl ester; R5X=cyclopropyl-methylbromide; NH$_2$A=2-aminothiazole

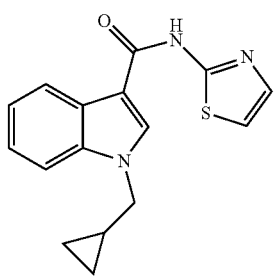

HPLC-MS (Method A): m/z=299 (M+1); R$_t$=2.1 min.

Example 49

General Procedure (K)

1-(5-Hydroxy-pentyl)-1H-indole-3-carboxylic acid thiazol-2-ylamide

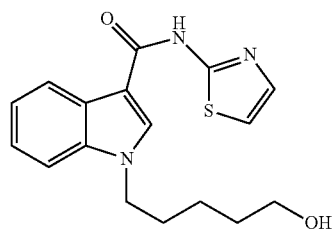

The title compound was prepared using 1H-indole-3-carboxylic acid thiazol-2-ylamide and 5-bromopentyl acetate as R5X.

HPLC-MS (Method A): m/z=330.1 (M+1); R$_t$=3.05 min

Example 50

General Procedure (K)

1-(4-Hydroxy-butyl)-1H-indole-3-carboxylic acid thiazol-2-ylamide

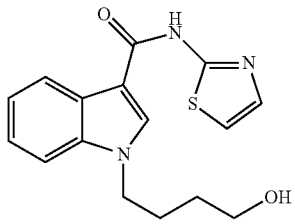

The title compound was prepared using 1H-indole-3-carboxylic acid thiazol-2-ylamide and 4-bromobutyl acetate as R5X.

HPLC-MS (Method A): m/z=316.0 (M+1); R$_t$=2.84 min

Example 51

1-Cyclopropylmethyl-1H-indole-3,6-dicarboxylic acid 6-amide 3-thiazol-2-ylamide

The compound was prepared according to the procedure for the synthesis of 1-Benzyl-6-(morpholine-4-carbonyl)-1H-indole-3-carboxylic acid thiazol-2-ylamide. Instead of morpholine ammonia (0.5 M) in dioxane was used and instead of benzyl bromide cyclopropyl-methylbromide was used.

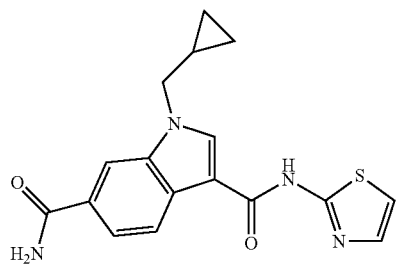

HPLC-MS (Method A): m/z=341 (M+1); R$_t$=2.6 min

Example 52

General Procedure (A)

1-Cyclopropylmethyl-6-fluoro-1H-indole-3-carboxylic acid benzothiazol-2-ylamide

Indole starting material=6-fluoroindole; R5X=cyclopropyl-methylbromide; NH$_2$A=2-aminobenzothiazole

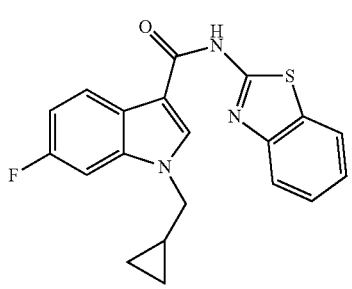

HPLC-MS (Method A): m/z=366 (M+1); R$_t$=4.8 min.

Example 53

General Procedure (K)

1-(2,2,2-Trifluoro-ethyl)-1H-indole-3-carboxylic acid thiazol-2-ylamide

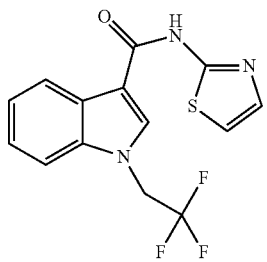

The title compound was prepared using 1H-indole-3-carboxylic acid thiazol-2-ylamide and 2,2,2-trifluoroethyl triflate as R5X.

HPLC-MS (Method A): m/z=325.9 (M+1); $R_t$=3.61 min

Example 54

General Procedure (I)

6-Fluoro-1-pyridin-4-ylmethyl-1H-indole-3-carboxylic acid thiazol-2-ylamide

Indole starting material=6-fluoroindole; R5X=4-chloromethylpyridine; $NH_2A$=2-aminothiazole

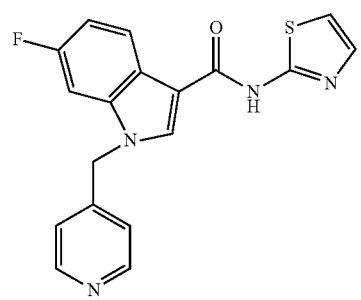

HPLC-MS (Method A): m/z=353 (M+1); $R_t$=2.8 min. $^1$H NMR (400 MHz, CDCl$_3$) δ 7.15 (dt, 1H), 7.23 (d, 1H), 7.50-7.57 (m, 2H), 7.60 (d, 1H), 8.22-8.29 (m, 1H), 8.63 (s, 1H), 8.77 (d, 2H) ppm.

Example 55

General Procedure (J)

6-Fluoro-1-pyridin-3-ylmethyl-1H-indole-3-carboxylic acid thiazol-2-ylamide

Indole starting material=6-fluoroindole; R5X=3-chloromethylpyridine; $NH_2A$=2-aminothiazole

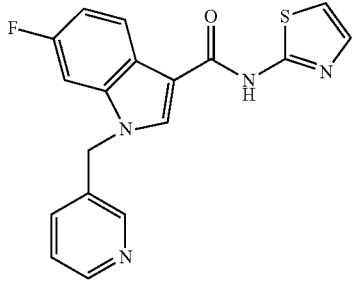

HPLC-MS (Method A): m/z=353 (M+1); $R_t$=2.57 min. $^1$H NMR (400 MHz, CDCl$_3$) δ 7.12 (dt, 1H), 7.20 (d, 1H), 7.50 (d, 1H), 7.62-7.73 (m, 2H), 8.05 (d, 1H), 8.17-8.28 (dd, 1H), 8.64 (s, 1H), 8.72 (d, 1H), 8.82 (s, 1H) ppm.

Example 56

General Procedure (J)

6-Fluoro-1-quinolin-2-ylmethyl-1H-indole-3-carboxylic acid thiazol-2-ylamide

Indole starting material=6-fluoroindole; R5X=3-chloromethyl-quinolin; $NH_2A$=2-aminothiazole

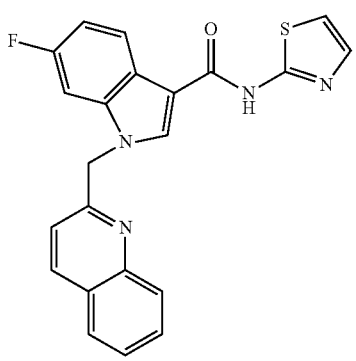

HPLC-MS (Method A): m/z=403 (M+1); $R_t$=3.7 min.

Example 57

General Procedure (I)

6-Fluoro-1-pyridin-2-ylmethyl-1H-indole-3-carboxylic acid thiazol-2-ylamide

Indole starting material=6-fluoroindole; R5X=2-chloromethylpyridine; NH₂A=2-aminothiazole

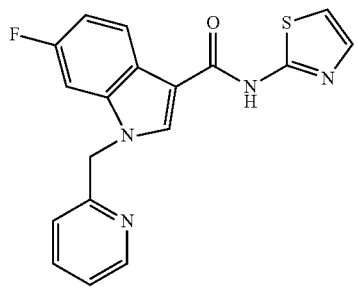

HPLC-MS (Method A): m/z=353 (M+1); R$_t$=3.69 min

Example 58

General Procedure (K)

1-(2-Methanesulfonyl-ethyl)-1H-indole-3-carboxylic acid thiazol-2-ylamide

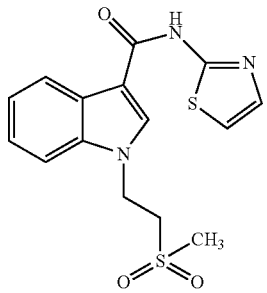

The title compound was prepared using 1H-indole-3-carboxylic acid thiazol-2-ylamide and toluene-4-sulfonic acid 2-methanesulfonyl-ethyl ester as R5X.

HPLC-MS (Method A): m/z=350.1 (M+1); R$_t$=2.68 min

Example 59

General Procedure (A)

6-Acetylamino-1-cyclopropylmethyl-1H-indole-3-carboxylic acid thiazol-2-ylamide

Indole starting material=indole-6-yl-acetamide; R5X=cyclopropyl-methylbromide; NH₂A=2-aminothiazole

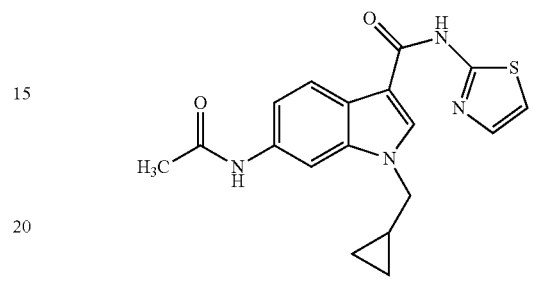

HPLC-MS (Method A): m/z=355 (M+1); R$_t$=2.8 min.

Example 60

[1-Cyclopropylmethyl-3-(thiazol-2-ylcarbamoyl)-1H-indol-6-yloxy]-acetic acid

6-Hydroxyindole (1.0 g, 7.51 mmol) in degassed MeCN (10 mL) was added K₂CO₃ (1.14 g, 8.26 mmol) followed by tert-butyl bromoacetate (1.16 g, 8.26 mmol) and the reaction mixture was stirred for 20 hours under N₂. The precipitate was filtered off and the solvent was removed in vacuo to give (1-H-indole-6-yloxy)-acetic acid. This was converted to [1-Cyclopropylmethyl-3-(thiazol-2-ylcarbamoyl)-1H-indol-6-yloxy]-acetic acid tert-butyl ester following general procedure (A). [1-Cyclopropylmethyl-3-(thiazol-2-ylcarbamoyl)-1H-indol-6-yloxy]-acetic acid was obtained by treating the intermediate with TFA-DCM (1:1) (2 mL) for 90 min before the solvent was removed in vacuo.

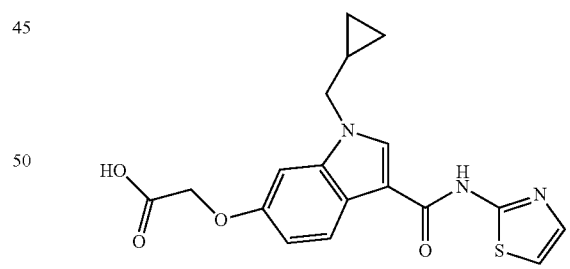

HPLC-MS (Method A): m/z=372 (M+1); R$_t$=3.0 min

Example 61

General Procedure (A)

1-Cyclopropylmethyl-6-methanesulfonylamino-1H-indole-3-carboxylic acid thiazol-2-ylamide Indole starting material: N-(1H-indole-6-yl)-methanesulfonamide, R5X=cyclopropyl-methylbromide; NH₂A=2-aminothiazole

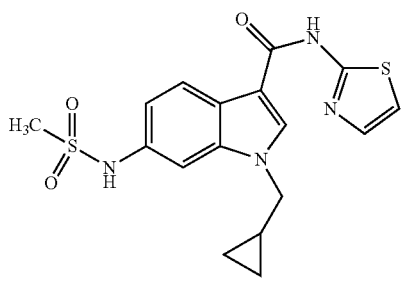

HPLC-MS (Method A): m/z=391 (M+1); R=3.0 min

Example 62

General Procedure (J, Step D)

6-Fluoro-1-(2-pyridin-2-yl-ethyl)-1H-indole-3-carboxylic acid thiazol-2-ylamide

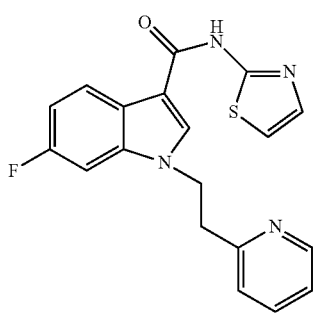

The title compound was prepared using 6-Fluoro-1H-indole-3-carboxylic acid thiazol-2-ylamide and toluene-4-sulfonic acid 2-pyridin-2-yl-ethyl ester as R5X.

HPLC-MS (Method A): m/z=367.2 (M+1); $R_t$=2.78 min

Example 63

1-Cyclopropylmethyl-6-hydroxymethyl-1H-indole-3-carboxylic acid thiazol-2-ylamide 1 g (1H-indole-6-yl)-methanol (1.0 g, 6.79 mmol) in DCM (25 mL) was added DBU (1.24 g, 8.15 mmol) and tert-butyldimethylsilylchloride (1.14 g, 7.54 mmol). The reaction mixture was stirred 16 hours before water (25 mL) was added. The phases were separated and the organic phase was washed with HCl (0.1 N, 25 mL) and sodium bicarbonate (sat., 25 mL) and dried MgSO₄. The solvent was removed in vacuo to give 1.6 g (90%) 6-(tert-butyldimethylsilanyloxymethyl)-indole. This was converted to 1-cyclopropylmethyl-6-hydroxymethyl-1H-indole-3-carboxylic acid thiazol-2-ylamide using general procedure A where R5X=cyclopropyl-methylbromide; NH₂A=2-aminothiazole.

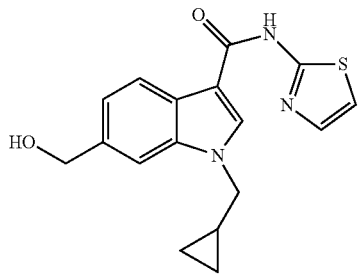

HPLC-MS (Method A): m/z=328 (M+1); $R_t$=2.8

Example 64

General Procedure (K)

6-Fluoro-1-(2-hydroxy-ethyl)-1H-indole-3-carboxylic acid thiazol-2-ylamide

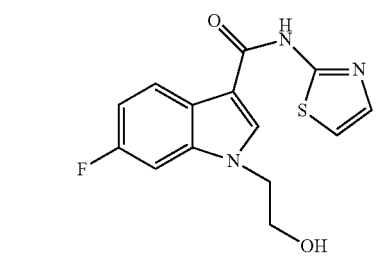

The title compound was prepared using 1H-indole-3-carboxylic acid thiazol-2-ylamide and 2-bromoethyl acetate as R5X.

HPLC-MS (Method A): m/z=306.1 (M+1); $R_t$=2.85 min

Example 65

{2-[(1-Cyclopropylmethyl-6-fluoro-1H-indole-3-carbonyl)-amino]-thiazol-4-ylsulfanyl}-acetic acid Indole starting material=6-fluoroindole; R5X=cyclopropyl-methylbromide; NH₂A=(2-amino-thiazol-5-ylsulfany)-acetic acid ethyl ester Preparation of (2-amino-thiazol-5-ylsulfany)-acetic acid ethyl ester: 5-bromoaminothiazole (25 g, 96.2 mmol) was dissolved in dry degassed DMF (50 mL) and the mixture was cooled on an ice bath before K₂CO₃ (26.5 g, 192.3 mmol) was added. Mercaptoacetic acid ethyl ester (11.6 g, 96.2 mmol) was added dropwise to the mixture at 0° C. The reaction mixture was stirred for 16 hours before brine-water (1:1) (500 mL) was added and extracted with Et₂O. The aqueous phase was extracted with additional 2×200 mL Et₂0, and the combined organic phases were washed with 2×200 mL brine and dried with MgSO4. The solvent was removed in vacuo to give an oil. The residue was dissolved in EtOAc, applied on a 10 cm silicagel column and eluded with EtOAc-heptane (1:1). The pure fractions were collected and the solvent was removed in vacuo to give 8.7 g (2-amino-thiazol-5-ylsulfany)-acetic acid ethyl ester.

Following general procedure A using 6-fluoroindole and R5X=cyclopropyl-methylbromide {2-[(1-Cyclopropylmethyl-6-fluoro-1H-indole-3-carbonyl)-amino]-thiazol-4-ylsulfanyl}-acetic acid ethyl ester was obtained. Ester hydrolysis: 110 mg (0.25 mmol) {2-[(1-cyclopropylmethyl-6-fluoro-1H-indole-3-carbonyl)-amino]-thiazol-4-ylsulfanyl}-acetic acid ethyl ester was dissolved in EtOH (3 mL) and NaOH (254 µL, 4N) was introduced. The mixture was heated to 80° C. for 1 hour before it was cooled to room temperature and pH was adjusted to 2 using 1 N HCl, whereupon a white precipitate was formed. The product was filtered off and dried to give 85 mg {2-[(1-Cyclopropylmethyl-6-fluoro-1H-indole-3-carbonyl)-amino]-thiazol-4-ylsulfanyl}-acetic acid.

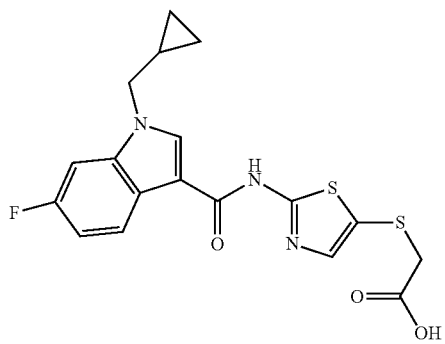

HPLC-MS (Method A): m/z=406 (M+1); $R_t$=3.6 min

Example 66

1-Cyclopropylmethyl-6-hydroxymethyl-1H-indole-3-carboxylic acid (4-methyl-thiazol-2-yl)amide The compound was prepared according to the procedure given for 1-Cyclopropylmethyl-6-hydroxymethyl-1H-indole-3-carboxylic acid thiazol-2-ylamide using 2-amino-4-methyl-thiazole.

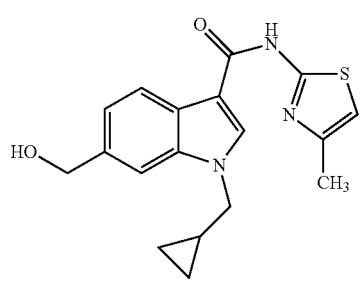

HPLC-MS (Method A): m/z=342 (M+1); $R_t$=3.1 min

Example 67

General

1-Cyclopropylmethyl-6-hydroxymethyl-1H-indole-3-carboxylic acid (5-methyl-thiazol-2-yl)amide The compound was prepared according to the procedure given for 1-Cyclopropylmethyl-6-hydroxymethyl-1H-indole-3-carboxylic acid thiazol-2-ylamide using 2-amino-5-methyl-thiazole.

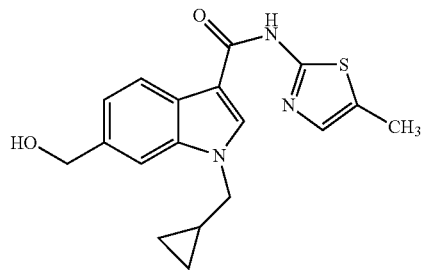

HPLC-MS (Method A): m/z=342 (M+1); $R_t$=3.1 min

Example 68

General procedure (I)

6-Fluoro-1-(2,2,2-trifluoro-ethyl)-indole-3-carboxylic acid thiazol-2-ylamide

Indole starting material=6-fluoroindole; R5X=Trifluoromethane-sulfonic acid 2,2,2-trifluoroethyl ester; NH$_2$A=2-aminothiazole

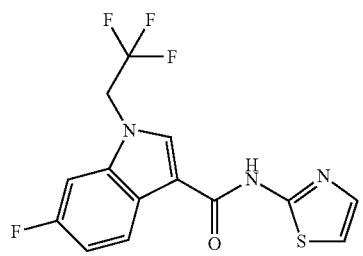

HPLC-MS (Method A): m/z=344 (M+1); $R_t$=4.0 min

Example 69

General Procedure (I)

6-Fluoro-1-(2,2,2-trifluoro-ethyl)-indole-3-carboxylic acid (5-methyl-thiazol-2-yl)-amide Indole starting material=6-fluoroindole; R5X=Trifluoromethane-sulfonic acid 2,2,2-trifluoroethyl ester; NH$_2$A=2-amino-5 methylthiazole

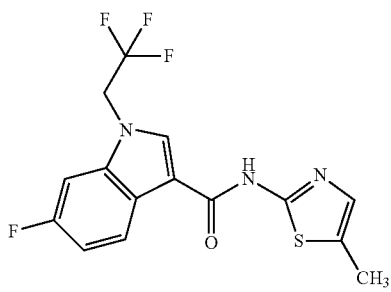

HPLC-MS (Method A): m/z=358 (M+1); $R_t$=4.1 min

Example 70

General Procedure (A)

5-Chloro-1-cyclopropylmethyl-6-fluoro-1H-indole-3-carboxylic acid thiazol-2-ylamide Indole starting material: 6-fluoro-5-chloroindole, R5X=cyclopropyl-methylbromide; NH₂A=2-aminothiazole

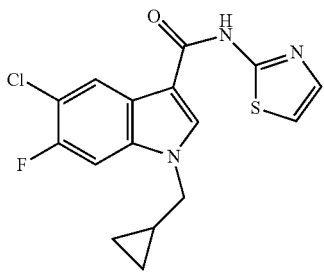

HPLC-MS (Method A): m/z=350 (M+1); R$_t$=4.1 min

Example 71

General Procedure (A)

1-Cyclopropylmethyl-5,6-difluoro-1H-indole-3-carboxylic acid thiazol-2-ylamide

Indole starting material: 5,6-difluoroindole, R5X=cyclopropyl-methylbromide; NH₂A=2-aminothiazole

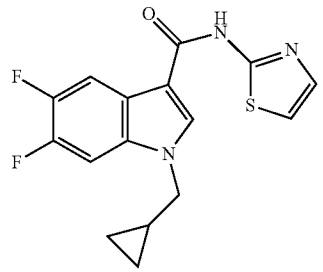

HPLC-MS (Method A): m/z=334 (M+1); R$_t$=3.8 min

Example 72

General Procedure (A)

1-Cyclopropylmethyl-6-methanesulfonyl-1H-indole-3-carboxylic acid thiazol-2-ylamide Indole starting material: 6-methanesulfonylindole, R5X=cyclopropyl-methylbromide; NH₂A=2-aminothiazole

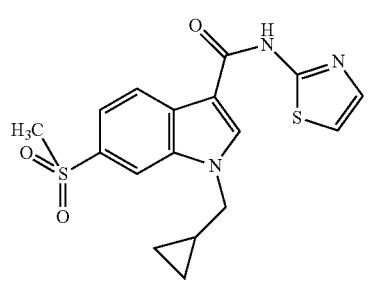

HPLC-MS (Method A): m/z=376 (M+1); R$_t$=2.9 min

Example 73

General Procedure (K)

6-Fluoro-1-(tetrahydro-furan-2-ylmethyl)-1H-indole-3-carboxylic acid thiazol-2-ylamide

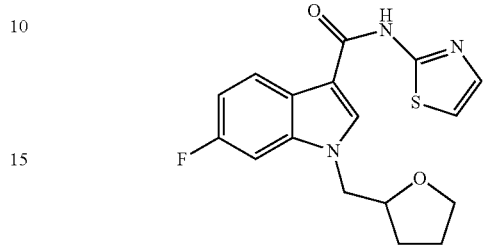

HPLC-MS (Method A): m/z=346 (M+1); R$_t$=3.5 min

Example 74

General Procedure (A)

1-Cyclopropylmethyl-6-fluoro-1H-indole-3-carboxylic acid [5-(pyridin-2-ylsulfanyl)-thiazol-2-yl]-amide Indole starting material: 6-fluoroindole, R5X=cyclopropyl-methylbromide; NH₂A=5-(pyridin-2-ylsulfanyl)-thiazole-2-ylamine

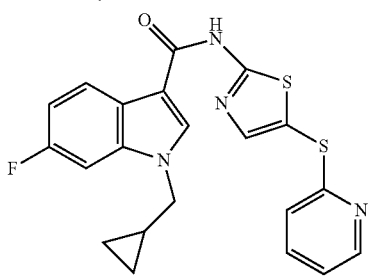

HPLC-MS (Method A): m/z=425 (M+1); R=4.7 min

Example 75

General Procedure (A)

1-Cyclopropylmethyl-6-fluoro-1H-indole-3-carboxylic acid [5-(pyrimidin-2-ylsulfanyl)thiazol-2-yl]-amide Indole starting material: 6-fluoroindole, R5X=cyclopropyl-methylbromide; NH₂A=5-(pyrimidin-2-ylsulfanyl)-thiazole-2-ylamine

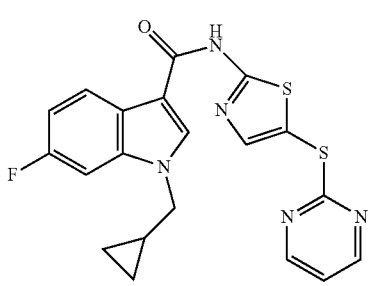

HPLC-MS (Method A): m/z=426 (M+1); R$_t$=4.6 min

Example 76

General Procedure (A)

1-Cyclopropylmethyl-6-fluoro-1H-indole-3-carboxylic acid [5-(1-methyl-1H-tetrazol-5-ylsulfanyl)-thiazol-2-yl]-amide Indole starting material: 6-fluoroindole, R5X=cyclopropyl-methylbromide; NH$_2$A=5-(1-methyl-1-H-tetrazol-5-ylsulfanyl)-thiazole-2-ylamine

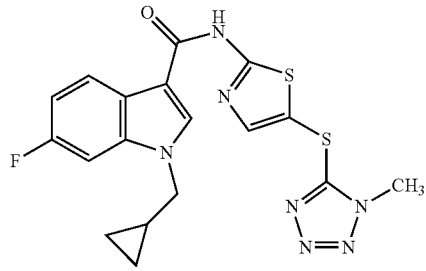

HPLC-MS (Method A): m/z=430 (M+1); R$_t$=4.3 min

Example 77

General Procedure (A)

2-{2-[(1-Cyclopropylmethyl-6-fluoro-1H-indole-3-carbonyl)-amino]-thiazol-5-ylsulfanyl}-3H-imidazole-4-carboxylic acid Indole starting material: 6-fluoroindole, R5X=cyclopropyl-methylbromide; NH$_2$A=2-(2-aminothiazole-5-ylsulfanyl)-3H-imidazole-4-carboxylic acid ethyl ester After step D the ester was hydrolyzed according to the procedure given for {2-[(1-cyclopropylmethyl-6-fluoro-1H-indole-3-carbonyl)-amino]-thiazol-4-ylsulfanyl}-acetic acid

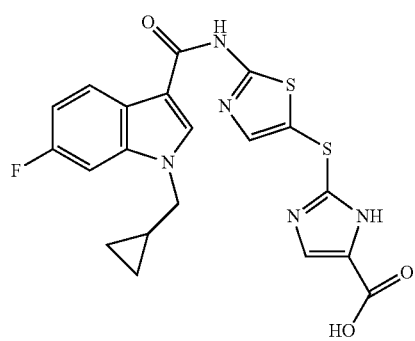

HPLC-MS (Method A): m/z=458 (M+1); R$_t$=3.1 min

Example 78

General Procedure (A)

{2-[(1-Cyclopropylmethyl-6-trifluoromethyl-1H-indole-3-carbonyl)-amino]-thiazol-5-ylsulfanyl}-acetic acid ethyl ester Indole starting material: 6-trifluoromethylindole, R5X=cyclopropyl-methylbromide; NH$_2$A=(2-amino-thiazole-5-ylsulfanyl)-acetic acid ethyl ester

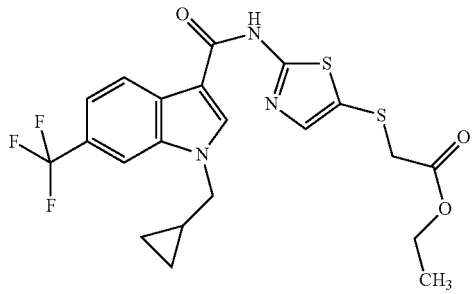

HPLC-MS (Method A): m/z=484 (M+1); R$_t$=5.0 min

Example 79

General Procedure (K)

6-Fluoro-1-(tetrahydro-furan-3-ylmethyl)-1H-indole-3-carboxylic acid thiazol-2-ylamide

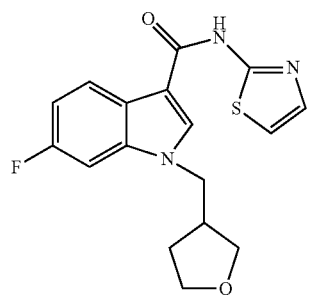

HPLC-MS (Method A): m/z=346 (M+1); R$_t$=3.4 min

Example 80

1-Cyclopropylmethyl-6-fluoro-1-indole-3-carboxylic acid (5-p-tolyloxy-thiazol-2-yl)-amide

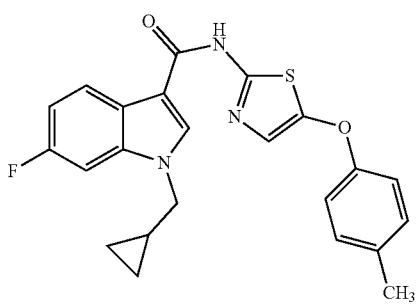

1-Cyclopropylmethyl-6-fluoro-1H-indole-3-carboxylic acid thiazol-2-ylamide (2.5 mmol), N-bromosuccinimide (6 mmol) was stirred in HOAc (25 mL) over night at room temperature. The reaction mixture was evaporated to dryness and the crude product was purified by flash chromatography (Horizon, EtOAc-heptane) to give 1-cyclopropylmethyl-6-fluoro-1H-indole-3-carboxylic acid (5-bromo-thiazol-2-yl)-amide in 32% yield. A solution of 1-cyclopropylmethyl-6-fluoro-1H-indole-3-carboxylic acid (5-bromo-thiazol-2-yl)- amide (0.2 mmol), p-cresol (0.2 mmol) and potassium-t-butoxide (0.44 mmol) in DME (3 mL) was heated in a closed vessel in a Smith Creator microwave oven for 300 s at 120° C. Addition of water followed by extraction with DCM, drying of the organic phase followed by purification by preparative HPLC (Method E) gave the title compound.

HPLC-MS (Method A): m/z=422.3 (M+1); $R_t$=5.18 min

Example 81

General Procedure (A)

{2-[(1-Cyclopropylmethyl-6-trifluoromethyl-1H-indole-3-carbonyl)-amino]-thiazol-5-ylsulfanyl}-acetic acid {2-[(1-Cyclopropylmethyl-6-trifluoromethyl-1H-indole-3-carbonyl)-amino]-thiazol-5-ylsulfanyl}-acetic acid ethyl ester was hydrolysed according to the procedure given in the procedure for the synthesis of {2-[(1-cyclopropylmethyl-6-fluoro-1H-indole-3-carbonyl)-amino]-thiazol-4-ylsulfanyl}-acetic acid

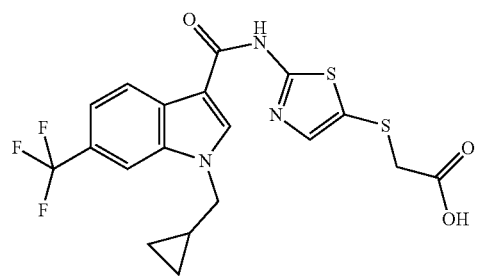

HPLC-MS (Method A): m/z=456 (M+1); $R_t$=4.1 min

Example 82

General Procedure (K)

1-(2-Cyano-ethyl)-indole-3-carboxylic acid thiazol-2-ylamide

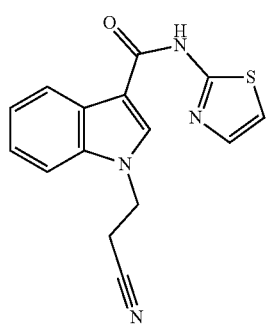

The title compound was prepared using 1H-indole-3-carboxylic acid thiazol-2-ylamide and 3-bromo propionitrile as R5X.

HPLC-MS (Method A): m/z=297.4 (M+1); $R_t$=2.84 min

Example 83

1-[2-(1H-Tetrazol-5-yl)-ethyl]-1-indole-3-carboxylic acid thiazol-2-ylamide

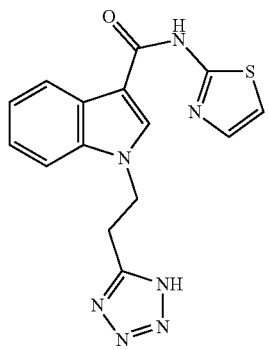

A mixture of 1-(2-cyano-ethyl)-indole-3-carboxylic acid thiazol-2-ylamide was heated in a closed vessel at 120° C. over night. The crude reaction mixture was purified by preparative HPLC (Method E) to give the title compound.

HPLC-MS (Method A): m/z=340.0 (M+1); $R_t$=2.55 min

Example 84

General Procedure (A)

3-{2-[(1-Cyclopropylmethyl-6-trifluoromethyl-1H-indole-3-carbonyl)-amino]-thiazol-5-ylsulfanyl}-propionic acid ethyl ester Indole starting material: 6-trifluoromethylindole, R5X=cyclopropyl-methylbromide; NH$_2$A=(2-amino-thiazole-5-ylsulfanyl)-propionic acid ethyl ester (prepared according to the procedure for the synthesis of (2-amino-thiazole-5-ylsulfanyl)-acetic acid ethyl ester described under the procedure for the synthesis of {2-[(1-Cyclopropylmethyl-6-fluoro-1H-indole-3-carbonyl)-amino]-thiazol-4-ylsulfanyl}-acetic acid.

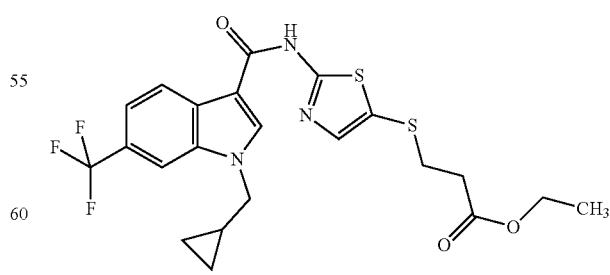

HPLC-MS (Method A): m/z=498 (M+1); $R_t$=4.9 min

Example 85

General Procedure (A)

3-{2-[(1-Cyclopropylmethyl-6-methyl-1H-indole-3-carbonyl)-amino]-thiazol-5-ylsulfanyl}-propionic acid ethyl ester Indole starting material: 6-methylindole, R5X=cyclopropyl-methylbromide; NH$_2$A=(2-aminothiazole-5-ylsulfanyl)-propionic acid ethyl ester

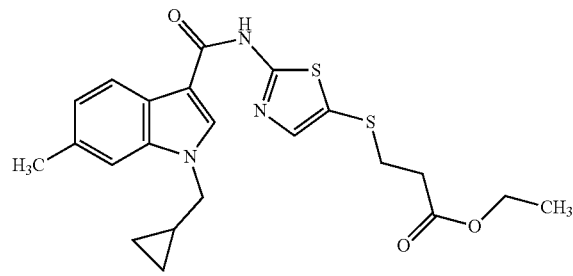

HPLC-MS (Method A): m/z=444 (M+1); R$_t$=4.7 min

Example 86

General Procedure (A)

3-{2-[(1-Cyclopropylmethyl-6-trifluoromethyl-1H-indole-3-carbonyl)-amino]-thiazol-5-ylsulfanyl}-propionic acid 3-{2-[(1-Cyclopropylmethyl-6-trifluoromethyl-1H-indole-3-carbonyl)-amino]-thiazol-5-ylsulfanyl}-propionic acid ethyl ester was hydrolysed according to the procedure given in the procedure for the synthesis of {2-[(1-cyclopropylmethyl-6-fluoro-1H-indole-3-carbonyl)-amino]-thiazol-4-ylsulfanyl}-acetic acid

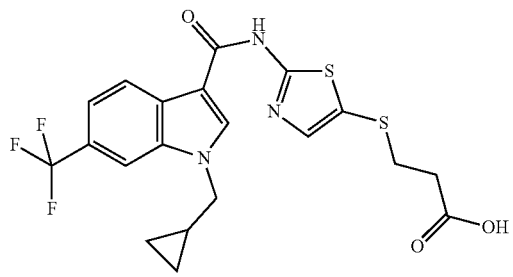

HPLC-MS (Method A): m/z=470 (M+1); R$_t$=4.5 min

Example 87

General Procedure (A)

3-{2-[(1-Cyclopropylmethyl-6-fluoro-1H-indole-3-carbonyl)-amino]-thiazol-5-ylsulfanyl}-propionic acid 3-{2-[(1-Cyclopropylmethyl-6-fluoro-1H-indole-3-carbonyl)-amino]-thiazol-5-ylsulfanyl}-propionic acid ethyl ester was hydrolysed according to the procedure given in the procedure for the synthesis of {2-[(1-cyclopropylmethyl-6-fluoro-1H-indole-3-carbonyl)-amino]-thiazol-4-ylsulfanyl}-acetic acid

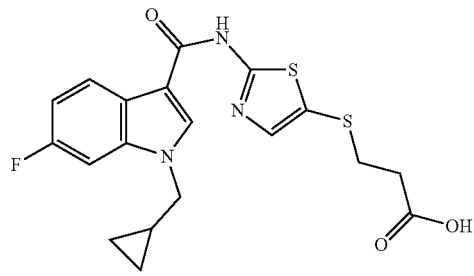

HPLC-MS (Method A): m/z=420 (M+1); R$_t$=4.1 min

Example 88

General Procedure (A)

3-{2-[(1-Cyclopropylmethyl-6-methyl-1H-indole-3-carbonyl)-amino]-thiazol-5-ylsulfanyl}-propionic acid Indole starting material: 6-methylindole, R5X=cyclopropyl-methylbromide; NH$_2$A=(2-aminothiazole-5-ylsulfanyl)-propionic acid ethyl ester 3-{2-[(1-Cyclopropylmethyl-6-methyl-1H-indole-3-carbonyl)-amino]-thiazol-5-ylsulfanyl}-propionic acid ethyl ester was hydrolysed according to the procedure given in the procedure for the synthesis of {2-[(1-cyclopropylmethyl-6-fluoro-1H-indole-3-carbonyl)-amino]-thiazol-4-ylsulfanyl}-acetic acid

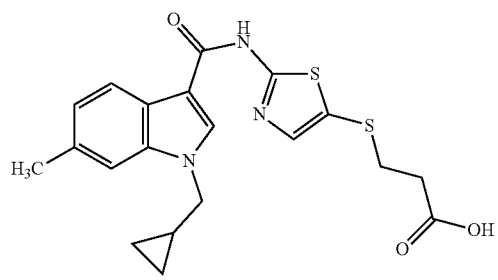

HPLC-MS (Method A): m/z=416 (M+1); R$_t$=4.1 min

Example 89

General Procedure (A)

1-Cyclopropylmethyl-6-methoxymethyl-1H-indole-3-carboxylic acid thiazol-2-ylamide Indole starting material: 6-methoxymethylindole, R5X=cyclopropyl-methylbromide; NH$_2$A=(2-amino-thiazole-5-ylsulfanyl)-propionic acid ethyl ester

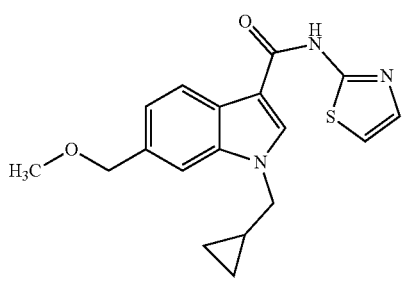

HPLC-MS (Method A): m/z=342 (M+1); $R_t$=3.3 min

Example 90

1-Cyclopropylmethyl-1H-pyrrolo[2,3-c]pyridine-3-carboxylic acid thiazol-2-ylamide Starting material: 1H-Pyrrolo[2,3-c]pyridine-3-carboxylic acid methyl ester, R5X=cyclopropyl-methylbromide; $NH_2A$=2-aminothiazole

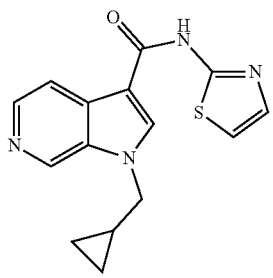

HPLC-MS (Method A): m/z=299 (M+1); $R_t$=1.1 min

Example 91

General Procedure (B)

{2-[(1-Cyclopropylmethyl-1H-pyrrolo[2,3-c]pyridine-3-carbonyl)-amino]-thiazol-5-ylsulfanyl}-acetic acid Starting material: 1H-Pyrrolo[2,3-c]pyridine-3-carboxylic acid methyl ester, R5X=cyclopropyl-methylbromide; $NH_2A$=(2-amino-thiazole-5-ylsulfanyl)-acetic acid ethyl ester
After step C the ester was hydrolysed according to the procedure given in the procedure for the synthesis of {2-[(1-cyclopropylmethyl-6-fluoro-1H-indole-3-carbonyl)-amino]-thiazol-4-ylsulfanyl}-acetic acid.

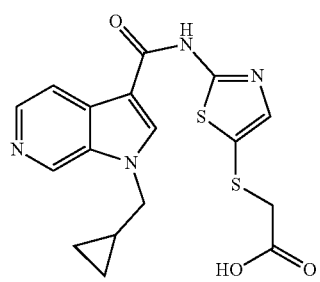

HPLC-MS (Method A): m/z=389 (M+1); $R_t$=1.2 min

Example 92

General Procedure (B)

3-{2-[(1-Benzyl-1H-indole-3-carbonyl)-amino]-thiazol-4-yl}-propionic acid ethyl ester Indole starting material: Indole-3-carboxylic acid ethyl ester, R5X=benzyl bromide, $NH_2A$=3-(2-amino-thiazol-4-yl)-propionic acid ethyl ester

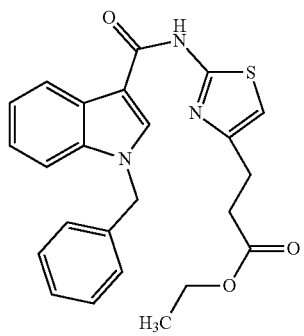

HPLC-MS (Method A): m/z=434 (M+1); $R_t$=2.2 min

Example 93

1-Benzyl-pyrrole-2-carboxylic acid thiazol-2-ylamide

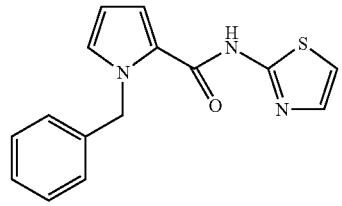

1-Benzyl-pyrrole-2-carboxylic acid (1.12 g) was prepared from ethyl pyrrole-2-carboxylate (1.39 g, 10.0 mmol) and benzyl bromide (1.26 mL, 11.0 mmol) following general procedures A and B. 1-Benzyl-pyrrole-2-carboxylic acid thiazol-2-ylamide (45 mg) was prepared from 1-benzyl-pyrrole-2-carboxylic acid (50 mg, 0.25 mmol) and 2-aminothiazole (25 mg, 0.25 mmol) following the general procedure F.
LCMS: 284 (M+1)$^+$, $^1$H NMR (400 MHz, CDCl$_3$) δ 5.70 (s, 2H), 6.18 (m, 1H), 6.92 (m, 2H), 7.04 (m, 1H), 7.15 (m, 2H), 7.28 (m, 3H), 7.40 (d, 1H) ppm.

Example 94

1-(4-Fluorobenzyl)-1H-pyrrole-2-carboxylic acid thiazol-2-ylamide

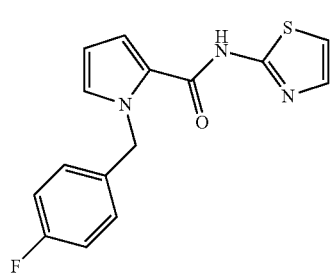

1-(4-Fluorobenzyl)-pyrrole-2-carboxylic acid (1.18 g) was prepared from ethyl-pyrrole-2-carboxylate (1.39 g, 10.0 mmol) and 4-fluorobenzyl bromide (1.38 mL, 11.0 mmol) following the general procedures A and B. 1-(4-Fluorobenzyl)-pyrrole-2-carboxylic acid thiazol-2-ylamide (45 mg) was prepared from 1-(4-fluorobenzyl)-pyrrole-2-carboxylic acid (55 mg, 0.25 mmol) and 2-aminothiazole (25 mg, 0.25 mmol) following the general procedure F.

LCMS: 302 (M+1)$^+$, $^1$H NMR (400 MHz, CDCl$_3$) δ 5.63 (s, 2H), 6.24 (m, 1H), 6.92 (m, 4H), 6.99 (d, 1H), 7.16 (dd, 2H), 7.26 (d, 1H), 10.85 (s, 1H) ppm.

Example 95

(2-{[1-Ethylpyrrole-2-carbonyl]amino}-thiazol-4-yl) acetic acid ethyl ester

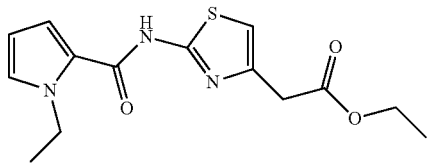

1-Ethylpyrrole-2-carboxylic acid (90 mg) was prepared from ethyl-pyrrole-2-carboxylate (140 mg, 1.0 mmol) and ethyl iodide (0.12 mL, 1.5 mmol) following the general procedures A and B. (2-{[1-Ethylpyrrole-2-carbonyl]-amino}-thiazol-4-yl)acetic acid ethyl ester (46 mg) was prepared from 1-ethylpyrrole-2-carboxylic acid (90 mg, 0.53 mmol) and 2-aminothiazol-4-yl acetic acid ethyl ester (95 mg, 0.53 mmol) following the general procedure F.

LCMS: 308 (M+1)$^+$, $^1$H NMR (400 MHz, CDCl$_3$) δ 1.59 (t, 3H), 1.76 (t, 3H), 4.00 (s, 2H), 4.54 (q, 2H), 4.76 (q, 2H), 6.5 (dd, 1H), 7.10 (s, 1H), 7.12 (d, 1H), 7.25 (d, 1H), 9.70 (br s, 1H) ppm.

Example 96

(2-{[1-(4-Fluorobenzyl)-1H-pyrrole-2-carbonyl]-amino}-thiazol-4-yl)acetic acid ethyl ester

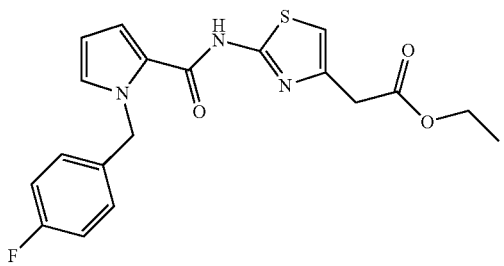

(2-{[1-(4-Fluorobenzyl)-1H-pyrrole-2-carbonyl]-amino}-thiazol-4-yl)acetic acid ethyl ester (60 mg) was prepared from 1-(4-fluorobenzyl)-pyrrole-2-carboxylic acid (55 mg, 0.25 mmol) and 2-aminothiazol-4-yl acetic acid ethyl ester (47 mg, 0.25 mmol) following the general procedure F.

LCMS: 388 (M+1)$^+$, $^1$H NMR (400 MHz, CDCl$_3$) δ 1.57 (t, 3H), 3.97 (s, 2H), 4.50 (q, 2H), 5.94 (s, 2H), 6.55 (m, 1H), 7.11 (d, 1H), 7.24 (m, 2H), 7.30 (t, 1H), 7.42 (m, 2H), 7.60 (d, 1H) ppm.

Example 97

4-Cyclopentanecarbonyl-1-ethylpyrrole-2-carboxylic acid thiazol-2-ylamide

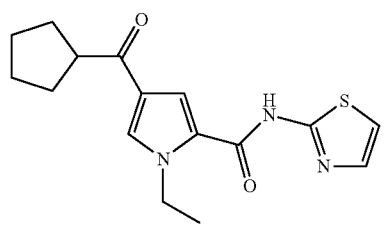

Ethyl-(1-ethylpyrrole)-2-carboxylic acid ester was prepared from ethyl pyrrole-2-carboxylate (834 mg, 6.0 mmol) and iodoethane (0.48 mL, 6.0 mmol) following the general procedure A. Anhydrous aluminum trichloride (800 mg, 6.0 mmol) was added to a solution of ethyl-(1-ethylpyrrole)-2-carboxylic acid ester in DCE (20 mL) at 0° C. After stirring for 10 min, cyclopentylcarbonyl chloride (1.45 mL, 15.0 mmol) was added and the reaction mixture was stirred for 24 h at room temperature. The reaction mixture was carefully poured into an ice-cold solution of 1.0 M HCl. The mixture was extracted with DCM (3×50 mL) and the combined organic extracts was washed with 1 M aqueous NaOH solution (50 mL) and then water. The organic layer was dried (sodium sulfate), filtered and concentrated. The crude acylated intermediate was used directly.

4-Cyclopentanecarbonyl-1-ethylpyrrole2-carboxylic acid (540 mg) was obtained after hydrolysis of the crude acyl ester intermediate using general procedure E. 4-Cyclopentanecarbonyl-1-ethylpyrrole-2-carboxylic acid thiazol-2-ylamide (50 mg) was prepared from 4-cyclopentanecarbonyl-1-ethyl-pyrrole-2-carboxylic acid (93 mg, 0.39 mmol) and 2-aminothizaole (40 mg, 0.4 mmol) following general procedure F.

LCMS: 318 (M+1)$^+$ $^1$H NMR (400 MHz, CDCl$_3$) δ 1.5 (t, 3H), 1.6-1.9 (m, 8H), 3.28 (quintet, 1H), 4.49 (q, 2H), 6.97 (d, 1H), 7.34 (m, 2H), 7.56 (d, 1H) ppm.

Example 98

4-Cyclopentanecarbonyl-1-butylpyrrole-2-carboxylic acid thiazol-2-ylamide

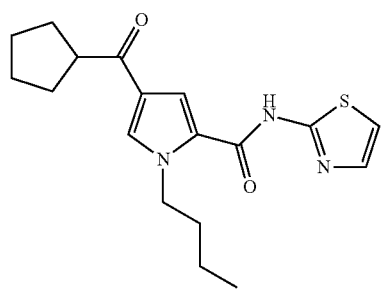

Ethyl-(1-butylpyrrole)-2-carboxylic acid ester was prepared from ethyl pyrrole-2-carboxylate (139 mg, 1.0 mmol) and iodobutane (0.11 mL, 1.0 mmol) following general procedure A.

Anhydrous aluminum trichloride (467 mg, 3.5 mmol) was added to a solution of ethyl-(1-butylpyrrole)-2-carboxylic acid ester in DCE (20 mL) at 0° C. After stirring for 10 min, cyclopentylcarbonyl chloride (0.15 mL, 1.0 mmol) was added and the reaction mixture was stirred for 24 h at room temperature. The reaction mixture was carefully poured into an ice-cold solution of 1.0 M HCl. The mixture was extracted with DCM (3×20 mL) and the combined organic extracts was washed with 1 M aqueous NaOH solution (20 mL) and then water. The organic layer was dried (sodium sulfate), filtered and concentrated. The crude acylated intermediate was used directly.

4-Cyclopentanecarbonyl-1-butyl-pyrrole-2-carboxylic acid (132 mg) was obtained following the hydrolysis of the ester intermediate via the general procedure E. 4-Cyclopentanecarbonyl-1-butyl-pyrrole-2-carboxylic acid thiazol-2-ylamide (40 mg) was prepared from 4-cyclopentanecarbonyl-1-butyl-pyrrole-2-carboxylic acid (132 mg, 0.5 mmol) and 2-aminothiazole (51 mg, 0.5 mmol) following the general procedure F.

LCMS: 346 (M+1)$^+$ $^1$H NMR (400 MHz, CDCl$_3$) δ 0.84 (m, 2H), 0.90 (t, 2H), 1.16 (t, 3H), 1.5-1.8 (m, 8H), 3.60 (quintet, 1H), 4.5 (t, 2H), 6.92 (d, 1H), 7.27 (d, 1H), 7.31 (s, 1), 7.28 (d, 1H) ppm.

Example 99

1-(Toluene-4-sulfonyl)-1H-pyrrole-3-carboxylic acid thiazol-2-ylamide

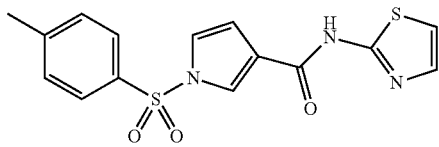

1-(Toluene-4-sulfonyl)-1H-pyrrole-3-carboxylic acid thiazol-2-ylamide (68 mg) was prepared from 1-(toluene-4-sulfonyl)-1H-pyrrole-3-carboxylic acid (66 mg, 0.25 mmol) and 2-aminothiazole (25 mg, 0.25 mmol) following the general procedure F.

LCMS: 348 (M+1)$^+$, $^1$H NMR (400 MHz, DMSO-d$_6$+CDCl$_3$) δ 2.30 (t, 3H), 6.99 (m, 2H), 7.18 (m, 1H), 7.33 (d, 2H), 7.41 (dd, 1H), 7.77 (d, 2H), 7.24 (dd, 2H), 8.22 (dd, 1H), 12.09 (br, 1H) ppm.

Example 100

2-(4-Fluoro-benzyl)-5-propyl-2H-pyrazole-3-carboxylic acid thiazol-2-ylamide

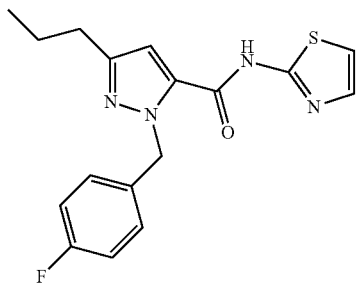

2-(4-Fluorobenzyl)-5-propyl-2H-pyrazole-3-carboxylic acid (0.78 g) was prepared from 5-propyl-2H-pyrazole-3-carboxylic acid ethyl ester (0.91 g, 5.0 mmol) and 4-fluorobenzyl bromide (1.05 g, 5.5 mmol) following the general procedures D and E. 2-(4-Fluorobenzyl)-5-propyl-2H-pyrazole-3-carboxylic acid thiazol-2-ylamide (50 mg) was prepared from 2-(4-fluoro-benzyl)-5-propyl-2H-pyrazole-3-carboxylic acid (65 mg, 0.25 mmol) and 2-aminothiazole (25 mg, 0.25 mmol) following the general procedure F.

LCMS: 345 (M+1)$^+$, $^1$H NMR (400 MHz, CDCl$_3$) δ 0.95 (t, 3H), 1.64 (m, 2H), 2.54 (m, 2H), 5.27 (s, 2H), 6.54 (d, 1H), 6.73 (s, 1H), 6.98-7.13 (m, 4H), 7.48 (d, 1H), 10.20 (br, 1H) ppm.

Example 101

1-Isobutyl-indazole-3-carboxylic acid thiazol-2-ylamide

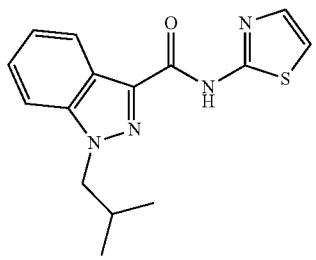

1-(Isobutyl)-indazole-3-carboxylic acid (340 mg) was obtained from methyl indazole-3-carboxylate (0.5 g, 2.84 mmol) and 1-iodo-2-methylpropane (0.33 mL, 2.84 mmol) following general procedures G and E. 1-(Isobutyl)-indazole-3-carboxylic acid thiazol-2-ylamide (66 mg) was prepared from 1-(isobutyl)-indazole-3-carboxylic acid (130 mg, 0.60 mmol) and 2-aminothiazole (150 mg, 1.5 mmol) following the general procedure H.

LCMS: 301 (M+1)$^+$, $^1$H NMR (400 MHz, CDCl$_3$) δ 1.00 (d, 6H), 2.42 (m, 1H), 4.60 (d, 2H), 7.02 (d, 1H), 7.35 (m, 1H), 7.548 (m, 2H), 7.51 (d, 1H), 8.42 (d, 1H), 10.29 (s, 1H) ppm.

Example 102

1-(2-Methylallyl)-indazole-3-carboxylic acid thiazol-2-ylamide

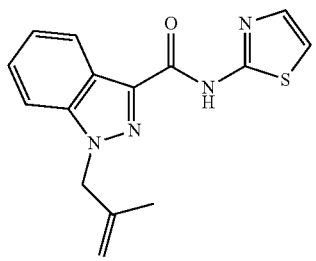

1-(2-Methylallyl)-indazole-3-carboxylic acid (440 mg) was obtained from methyl indazole-3-carboxylate (0.5 g, 2.84 mmol) and 1-chloro-2-methylpropene (0.28 mL, 2.84 mmol, with a catalytic amount of sodium iodide) following the general procedures G and E. 1-(2-Methylallyl)indazole- 3-carboxylic acid thiazol-2-ylamide (45 mg) was prepared from 1-(2-methylallyl)indazole-3-carboxylic acid (140 mg, 0.65 mmol) and 2-aminothiazole (65 mg, 0.65 mmol) following the general procedure H.

LCMS: 299 (M+1)+, 1H NMR (400 MHz, CDCl3) δ 1.68 (s, 3H), 4.85 (s, 1H), 5.00 (s, 3H), 7.02 (d, 1H), 7.36 (m, 1H), 7.46 (d, 2H), 7.55 (d, 1H), 8.46 (d, 1H), 10.45 (br s, 1H) ppm.

Example 103

(2-{[1-(Benzyl)-1H-pyrrole-2-carbonyl]-amino}-thiazol-4-yl)acetic acid ethyl ester

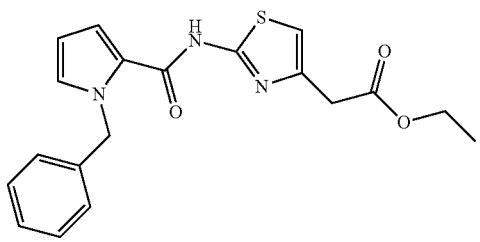

(2-{[1-(Benzyl)-1H-pyrrole-2-carbonyl]-amino}-thiazol-4-yl)acetic acid ethyl ester (60 mg) was prepared from 1-benzyl-pyrrole-2-carboxylic acid (50 mg, 0.25 mmol) and 2-aminothiazol-4-yl acetic acid ethyl ester (47 mg, 0.25 mmol) following general procedure F.

LCMS: 370 (M+1)+

Example 104

(2-{[1-(4-Fluorobenzyl)-1H-pyrrole-2-carbonyl]-amino}-thiazol-4-yl)acetic acid

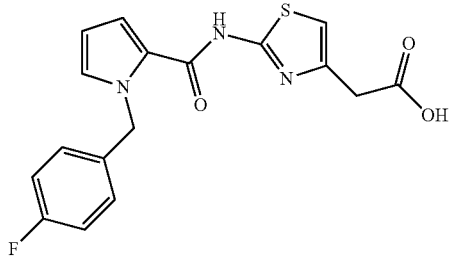

(2-{[1-(4-Fluorobenzyl)-1H-pyrrole-2-carbonyl]-amino}-thiazol-4-yl)acetic acid ethyl ester (60 mg) was hydrolyzed to give (2-{[1-(4-fluorobenzyl)-1H-pyrrole-2-carbonyl]-amino}-thiazol-4-yl)acetic acid (50 mg) following general procedure E.

LCMS: 360 (M+1)+, 1H NMR (400 MHz, CD3OD) δ 3.64 (s, 2H), 5.62 (s, 2H), 6.23 (m, 1H), 6.82 (s, 1H), 6.99 (m, 2H), 7.12 (m, 2H), 7.18 (m, 2H) ppm.

Example 105

1-Butyl-pyrrole-2-carboxylic acid thiazol-2-ylamide

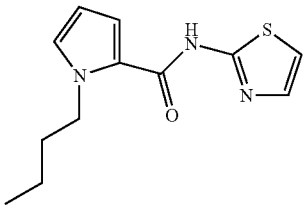

1-Butyl-pyrrole-2-carboxylic acid (130 mg) was prepared from ethyl pyrrole-2-carboxylate (139 mg, 1.0 mmol) and butyl iodide (0.12 mL, 1.0 mmol) following general procedures D and E. 1-Butyl-pyrrole-2-carboxylic acid thiazol-2-ylamide (100 mg) was prepared from 1-butyl-pyrrole-2-carboxylic acid (130 mg, 0.77 mmol) and 2-aminothiazole (80 mg, 0.80 mmol) following general procedure F.

LCMS: 250 (M+1)+, 1H NMR (400 MHz, CDCl3) δ 0.92 (t, 3H), 1.34 (q, 2H), 1.80 (m, 2H), 4.40 (t, 2H), 6.50 (m, 1H), 7.24 (m, 2H), 7.27 (m, 1H), 7.64 (d, 1H) ppm.

Example 106

2-(3,4-Dichloro-benzyl)-5-propyl-2H-pyrazole-3-carboxylic acid thiazol-2-ylamide

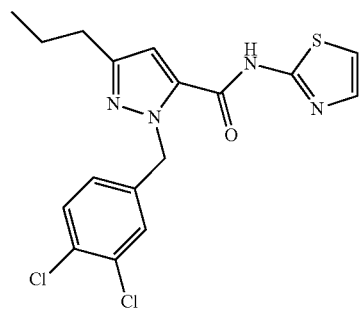

2-(3,4-Dichlorobenzyl)-5-propyl-2H-pyrazole-3-carboxylic acid (0.84 g) was prepared from 5-propyl-2H-pyrazole-3-carboxylic acid ethyl ester (0.91 g, 5.0 mmol) and 3,4-dichlorobenzyl bromide (1.32 g, 5.5 mmol) following the general procedures D and E. 2-(3,4-Dichlorobenzyl)-5-propyl-2H-pyrazole-3-carboxylic acid thiazol-2-ylamide (63 mg) was prepared from 2-(3,4-dichlorobenzyl)-5-propyl-2H-pyrazole-3-carboxylic acid (78 mg, 0.25 mmol) and 2-aminothiazole (25 mg, 0.25 mmol) following the general procedure F.

LCMS: 395 (M+1)+ 1H NMR (400 MHz, CDCl3) δ 0.96 (t, 3H), 1.64 (m, 2H), 2.51 (m, 2H), 5.25 (s, 2H), 6.75 (d, 1H), 6.94 (dd, 1H), 6.98 (dd, 1H), 7.20 (d, 1H), 7.41 (d, 1H), 7.46 (d, 1H), 10.20 (br, 1H) ppm.

Pharmacological Methods
Biological Assay
Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM MgCl$_2$, 2 mM dithiothreitol, 0.6 mM NADP, 1 mM ATP, 0.195 µM G-6-P dehydrogenase (from Roche, 127 671), 15 nM recombinant human glucokinase. The glucokinase is human liver glucokinase N-terminally truncated with an N-terminal His-tag ((His)$_8$-VEQILA . . . Q466) and is expressed in E. coli as a soluble protein with enzymatic activity comparable to liver extracted GK.

The purification of His-tagged human glucokinase (hGK) was performed as follows: The cell pellet from 50 ml E. coli culture was resuspended in 5 ml extraction buffer A (25 mM HEPES, pH 8.0, 1 mM MgCl$_2$, 150 mM NaCl, 2 mM mercaptoethanol) with addition of 0.25 mg/ml lysozyme and 50 µg/ml sodium azide. After 5 minutes at room temperature 5 ml of extraction buffer B (1.5 M NaCl, 100 mM CaCl$_2$, 100 mM MgCl$_2$, 0.02 mg/ml DNase 1, protease inhibitor tablet (Complete® 1697498): 1 tablet pr. 20 ml buffer) was added. The extract was then centrifugated at 15.000 g for 30 minutes. The resulting supernatant was loaded on a 1 ml Metal Chelate Affinity Chromatography (MCAC) Column charged with Ni$^{2+}$. The column is washed with 2 volumes buffer A containing 20 mM imidazole and the bound his-tagged hGK is subsequently eluted using a 20 minute gradient of 20 to 500 mM imidazol in buffer A. Fractions are examined using SDS-gel-electrophoresis, and fractions containing hGK (MW: 52 KDa) are pooled. Finally a gelfiltration step is used for final polishing and buffer exchange. hGK containing fractions are loaded onto a Superdex 75 (16/60) gelfiltration column and eluted with Buffer B (25 mM HEPES, pH 8.0, 1 mM MgCl$_2$, 150 mM NaCl, 1 mM Dithiothreitol). The purified hGK is examined by SDS-gel electrophoresis and MALDI mass spectrometry and finally 20% glycerol is added before freezing. The yield from 50 ml E. coli culture is generally approximately 2-3 mg hGK with a purity >90%.

The compound to be tested is added into the well in final 2.5% DMSO concentration in an amount sufficient to give a desired concentration of compound, for instance 1, 5, 10, 25 or 50 µM. The reaction starts after glucose is added to a final concentration of 2, 5, 10 or 15 mM. The assay uses a 96-well UV plate and the final assay volume used is 200 µl/well. The plate is incubated at 25° C. for 5 min and kinetics is measured at 340 nm in SpectraMax every 30 seconds for 5 minutes. Results for each compound are expressed as the fold activation of the glucokinase activity compared to the activation of the glucokinase enzyme in an assay without compound after having been subtracted from a "blank", which is without glucokinase enzyme and without compound. The compounds in each of the Examples exhibits activation of glucokinase in this assay. A compound, which at a concentration of at or below 30 µM gives 1.5-fold higher glucokinase activity than the result from the assay without compound, is deemed to be an activator of glucokinase.

The glucose sensitivity of the compounds are measured at a compound concentration of 10 µM and at glucose concentrations of 5 and 15 mM.

Glucokinase Activity Assay (II)
Determination of Glycogen Deposition in Isolated Rat Hepatocytes:

Hepatocytes are isolated from rats fed ad libitum by a two-step perfusion technique. Cell viability, assessed by trypan blue exclusion, is consistently greater than 80%. Cells are plated onto collagen-coated 96-well plates in basal medium (Medium 199 (5.5 mM glucose) supplemented with 0.1 µM dexamethasone, 100 units/ml penicillin, 100 mg/ml streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM Mg$_2$SO$_4$, 1.5 mM KH$_2$PO$_4$, 20 mM HEPES, 9 mM NaHCO$_3$, 0.1% w/v HSA, and 2.25 mM CaCl$_2$, pH 7.4 at 37° C.) and incubated in 100 µl buffer A containing 15 mM glucose and increasing concentrations of the test compound, such as for instance 1, 5, 10, 25, 50 or 100 µM, for 180 minutes. Glycogen content is measured using standard procedures (Agius, L. et al, Biochem J. 266, 91-102 (1990). A compound, which when used in this assay gives an significant increase in glycogen content compared to the result from the assay without compound, is deemed to have activity in this assay.

Glucokinase Activity Assay (III)
Stimulation of Insulin Secretion by Glucokinase Activators in INS-1E Cells The glucose responsive β-cell line INS-1E is cultivated as described by Asfari M et al., Endocrinology, 130, 167-178 (1992). The cells are then seeded into 96 well cell culture plates and grown to a density of approximately 5×10$^4$ per well. Stimulation of glucose dependent insulin secretion is tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 µM, and the supernatants collected for measurements of insulin concentrations by ELISA (n=4). A compound, which when used in this assay gives an significant increase in insulin secretion in response to glucose compared to the result from the assay without compound, is deemed to have activity in this assay.

While the invention has been described and illustrated with reference to certain preferred embodiments thereof, those skilled in the art will appreciate that various changes, modifications and substitutions can be made therein without departing from the spirit and scope of the present invention. For example, effective dosages other than the preferred dosages as set forth herein may be applicable as a consequence of variations in the responsiveness of the mammal being treated for glucokinase-deficiency mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

The invention claimed is:
1. A compound of the formula:

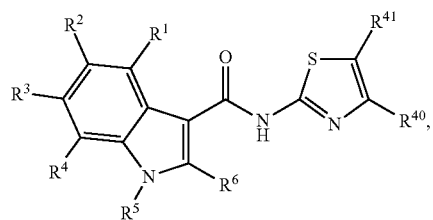

wherein:
R$^1$, R$^2$, R$^3$ and R$^4$ are independently selected from the group consisting of hydrogen, F, Cl, Br, hydroxy, carboxy, —CF$_3$, methyl, ethyl, propyl, —CH$_2$—C(O)

OH, —(CH$_2$)$_2$—C(O)OH, —CH$_2$—OH, —(CH$_2$)$_2$—OH, —O—CH$_2$—C(O)OH, —(CH$_2$)$_2$—N(CH$_3$)$_2$, —O—(CH$_2$)$_2$—C(O)OH and —CO—NR$^{13}$R$^{14}$;

R$^{13}$ and R$^{14}$ together with the nitrogen to which they are attached form a morpholine ring;

R$^5$ is benzyl, wherein the phenyl part may be substituted with one or more substituents independently selected from R$^{20}$;

R$^6$ is hydrogen;

R$^{20}$ is selected from the group consisting of halogen, cyano, CF$_3$, hydroxy, carboxy, —C(O)—O—C$_{1-6}$-alkyl, C$_{1-6}$-alkoxy, C$_{1-6}$-alkyl, carboxy-C$_{1-6}$-alkyl, amino-C$_{1-6}$-alkyl, hydroxy-C$_{1-6}$-alkyl, —NR$^{22}$R$^{23}$ and —CONR$^{24}$R$^{25}$;

R$^{22}$ and R$^{23}$ are independently selected from the group consisting of hydrogen, —C(O)—CH$_3$, methyl, ethyl and propyl;

R$^{24}$ and R$^{25}$ are independently selected from the group consisting of hydrogen, methyl, ethyl and propyl;

R$^{40}$ is hydrogen;

R$^{41}$ is —CH$_2$CO$_2$H;

or a salt thereof with any pharmaceutically acceptable acid or base.

2. The compound of claim 1, wherein
R$^1$ and R$^2$ are each hydrogen; and
R$^3$ and R$^4$ are independently selected from the group consisting of hydrogen, F, Cl, Br, hydroxy, carboxy, —CF$_3$, methyl, ethyl, propyl, —CH$_2$—C(O)OH, —(CH$_2$)$_2$—C(O)OH, —CH$_2$—OH, —(CH$_2$)$_2$—OH, —O—CH$_2$—C(O)OH, —(CH$_2$)$_2$—N(CH$_3$)$_2$, —O—(CH$_2$)$_2$—C(O)OH and —CO—NR$^{13}$R$^{14}$.

3. The compound of claim 1, wherein
R$^1$ and R$^2$ are each hydrogen; and
R$^3$ and R$^4$ are independently selected from the group consisting of hydrogen, F, Cl, Br, —CF$_3$, methyl, ethyl, propyl, and —CO—NR$^{13}$R$^{14}$.

4. The compound of claim 1, wherein
R$^1$ and R$^2$ are each hydrogen; and
R$^3$ and R$^4$ are independently selected from the group consisting of hydrogen, F, methyl, and —CO—NR$^{13}$R$^{14}$.

5. The compound of claim 1, wherein
R$^{20}$ is selected from the group consisting of halogen, CF$_3$, C$_{1-6}$-alkoxy, C$_{1-6}$-alkyl, —NR$^{22}$R$^{23}$ and —CONR$^{24}$R$^{25}$;

R$^{22}$ and R$^{23}$ are independently selected from the group consisting of hydrogen and —C(O)—CH$_3$; and R$^{24}$ and R$^{25}$ are hydrogen.

6. The compound of claim 1, selected from {2-[(1-Benzyl-1H-indole-3-carbonyl)-amino]-thiazol-4-yl}-acetic acid, and a salt thereof with any pharmaceutically acceptable acid or base.

7. A pharmaceutical composition comprising one or more compounds according to claim 1, or a pharmaceutically acceptable salt thereof, and one or more pharmaceutically acceptable carriers or diluents.

8. A method of treating type 2 diabetes, comprising administering to a subject in need of such treatment a therapeutically effective amount of a pharmaceutical composition according to claim 7.

* * * * *